United States Patent
Rabbitts et al.

(10) Patent No.: US 11,724,999 B2
(45) Date of Patent: Aug. 15, 2023

(54) INHIBITORS OF RAS-EFFECTOR PROTEIN INTERACTIONS

(71) Applicant: Oxford University Innovation Limited, Oxford (GB)

(72) Inventors: Terrence Rabbitts, Oxford (GB); Camilo Quevedo, Oxford (GB); Abimael Cruz, Oxford (GB); Simon Phillips, Oxford (GB); Philip Spencer Fallon, Saffron Walden (GB); Anna Hopkins, Saffron Walden (GB); Lydia Yuen-Wah Lee, Saffron Walden (GB); Tenin Traore, Saffron Walden (GB); Sophie Caroline Williams, Saffron Walden (GB); Natalie Louise Winfield, Saffron Walden (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 16/963,540

(22) PCT Filed: Jan. 23, 2019

(86) PCT No.: PCT/GB2019/050200
§ 371 (c)(1),
(2) Date: Jul. 21, 2020

(87) PCT Pub. No.: WO2019/145719
PCT Pub. Date: Aug. 1, 2019

(65) Prior Publication Data
US 2021/0047305 A1 Feb. 18, 2021

(30) Foreign Application Priority Data

Jan. 24, 2018 (GB) .................................. 1801130

(51) Int. Cl.
| | | |
|---|---|---|
| *C07D 405/12* | (2006.01) | |
| *C07D 319/20* | (2006.01) | |
| *C07D 405/14* | (2006.01) | |
| *C07D 407/12* | (2006.01) | |
| *C07D 413/12* | (2006.01) | |
| *C07D 413/14* | (2006.01) | |
| *A61K 45/06* | (2006.01) | |

(52) U.S. Cl.
CPC ......... *C07D 405/12* (2013.01); *C07D 319/20* (2013.01); *C07D 405/14* (2013.01); *C07D 407/12* (2013.01); *C07D 413/12* (2013.01); *C07D 413/14* (2013.01); *A61K 45/06* (2013.01)

(58) Field of Classification Search
CPC .. C07D 405/12; C07D 319/20; C07D 405/14; C07D 407/12; C07D 413/12; C07D 413/14; A61K 45/06
See application file for complete search history.

(56) References Cited

U.S. PATENT DOCUMENTS

| | | | |
|---|---|---|---|
| 5,120,758 A | 6/1992 | Satoh | |
| 5,126,366 A * | 6/1992 | Stack ................... | C07D 319/20 514/452 |
| 5,166,367 A | 11/1992 | Stack et al. | |
| 8,809,536 B2 * | 8/2014 | Din Belle ............... | A61P 25/08 546/148 |

FOREIGN PATENT DOCUMENTS

| | | |
|---|---|---|
| EP | 0 565 732 A1 | 10/1993 |
| JP | S61254576 A | 11/1986 |
| WO | 2002/072567 A2 | 9/2002 |
| WO | 2003/029239 A1 | 4/2003 |
| WO | 2009/013390 A1 | 1/2009 |
| WO | 2009/079008 A1 | 6/2009 |
| WO | 2013/121209 A1 | 8/2013 |
| WO | 2014/106660 A1 | 7/2014 |
| WO | 2016/044772 A1 | 3/2016 |

OTHER PUBLICATIONS

Ito et al. in Cancer Science 94(1), 3-8 (2003) (Year: 2003).*
Choi et al. in Yakhak Hoeji 54(3), 200-204 (2010) (Year: 2010).*
Liu et al. in Experimental and Therapeutic Medicine 4:716-722 (2012) (Year: 2012).*
International Search Report & Written Opinion for WO2019/145719 (PCT/GB2019/050200 ), dated Mar. 21, 2019, pp. 1-14.
UK Search Report for GB1801130.4, dated Sep. 20, 2018, pp. 1-5.
Chem.MedChem, 12, 2017, pp. 1303-1318 [available https://onlinelibrary.wiley.com/doi/epdf/10.1002/cmdc.201700201] Strniero et al., "2,6-difluorobenzamide inhibitors of bacterial cell division protein FtsZ: design, synthesis and structure-activity relationships". Yakhak Hoechi, vol. 54, No. 3,2010, pp. 200-204, Choi et al., "Synthesis of 7-aryloxy-chroman-2-carboxamides and their evaluation of NF-KB inhibitory activities".

(Continued)

*Primary Examiner* — Jared Barsky
(74) *Attorney, Agent, or Firm* — Thomas | Horstemeyer, LLP

(57) ABSTRACT

The present invention relates to compounds of Formula I as defined herein, and salts and solvates thereof. (I) The present invention also relates to pharmaceutical compositions comprising compounds of Formula (I), and to compounds of Formula (I) for use in the treatment of proliferative disorders, such as cancer, as well as other diseases or conditions in which inhibition of a RAS-effector protein-protein interaction is implicated.

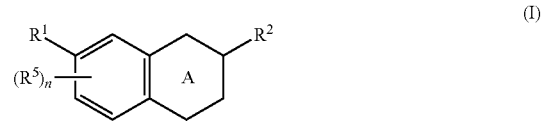

20 Claims, No Drawings

(56) References Cited

OTHER PUBLICATIONS

Camilo E. Quevedo et al: "Small molecule inhibitors of RAS-effector protein interactions derived using an intracellular antibody fragment", Nature Communications, vol. 9, No. 1, Aug. 9, 2018 (Aug. 9, 2018).

* cited by examiner

INHIBITORS OF RAS-EFFECTOR PROTEIN INTERACTIONS

CROSS-REFERENCE TO RELATED APPLICATIONS

This application is the National Stage of International Application No. PCT/GB2019/050200, filed Jan. 23, 2019, which claims priority to GB 1801130.4, filed Jan. 24, 2018, which are entirely incorporated herein by reference.

INTRODUCTION

This application relates to compounds of Formula I, as defined herein, and salts or solvates thereof.

The compounds described herein have the capability to inhibit protein-protein interactions, in particular interactions between RAS and effector proteins (such as RAF and PI3K) and may be used to treat diseases or conditions mediated, at least in part, by mutant RAS, such as cancer.

The present application further provides pharmaceutical compositions comprising a compound of Formula I, or a pharmaceutically acceptable salt or solvate thereof, and an pharmaceutically acceptable excipient.

The present application also provides methods of treating a proliferative disorder, such as cancer, in a subject in need thereof comprising administering to the subject a compound of Formula I or a pharmaceutically acceptable salt or solvate thereof.

BACKGROUND OF THE INVENTION

The aetiology of many human diseases such as cancer, neural degeneration and inflammation involves abnormal proteins participating in macromolecular complexes to elicit a biologically relevant effect. As such, protein-protein interactions represent a major potential drug target for manifold human disease indications.

The RAS proteins are guanine nucleotide binding molecules that play key roles in signal transduction as molecular switches, mediated through two switch regions displaying conformational differences between active (GTP bound) and inactive (GDP bound) states (Vetter and Wittinghofer, 2001). Most of the RAS effectors bind to these RAS switch regions (Downward, 2003). RAS is the most important target in cell transformation, being involved in cell proliferation and differentiation through the RAF-MEK-ERK cascade (Marshall, 1995; Kolch, 2005) and cell survival through activation of PI3K (Downward, 2003). The RAS effector, RAL-GDS, is also involved in RAS-dependent tumorigenesis in vivo (Gonzalez-Garcia et al, 2005) and cell transformation in human cells (Rangarajan et al, 2004).

Activating RAS gene mutations are found in as many as 30% of humans, with the highest frequencies in pancreas, colon and lung adenocarcinoma. Mutations of the RAS proteins (K, H or NRAS) create constitutively activated GTP-bound forms that promote cell transformation in a signal-independent manner (Adjei, 2001). In addition, secondary RAS-associated aberrations such as mutation or overexpression of receptor tyrosine kinases (e.g. EGFR, ERBB2) have been indicated in many cancers that lack RAS mutation (Mendelsohn and Baselga, 2000).

Thus, inhibiting aberrant RAS function has been an exciting possible mode of human cancer therapy. This notion has been supported by observations in mouse models in which oncogenic RAS has been shown to be essential for early onset of tumours and necessary for maintenance of tumour viability (Johnson et al, 2001), as tumours harbouring mutant RAS can regress when mutant RAS expression is stopped (Chin et al, 1999; Fisher et al, 2001).

These facts highlight activated RAS proteins as attractive targets for cancer therapy. Despite this, anti-RAS therapies have not yet been particularly effective (Friday and Adjei, 2005). Farnesyltransferase inhibitors (FTIs) can inhibit membrane localisation of RAS proteins by preventing post-translational modification, and thus blocking downstream RAS signalling. However, the antitumour activity of FTIs may only partly be due to targeting RAS and may also affect farnesylation of other proteins (Friday and Adjei, 2005).

An ideal RAS-based anticancer therapy would involve reagents that can specifically inhibit oncogenic RAS. Antibodies have such qualities of specificity and affinity that can easily be manipulated. However, most oncogenic proteins, including RAS, are located inside cells and not available for antibody-mediated targeting.

Over the last decade, antibody engineering has led to development of fragments that can be expressed intracellularly (intrabodies) (Cattaneo and Biocca, 1997), but there are still few intrabodies that work efficiently in the reducing environment of cells due to the usual need for disulphide bonds for correct folding. To overcome this limitation, intracellular antibody capture (IAC) has been developed, based on in vivo yeast two-hybrid screening (Visintin et al, 1999; Tse et al, 2002; Tanaka and Rabbitts, 2003), and it has been shown that single variable region (V) domains (iDabs) are highly efficient as intrabodies (Tanaka et al, 2003).

A single domain VH intrabody binding specifically to activated GTP-bound RAS with high affinity has been shown to neutralise oncogenicity in cancerous cells harbouring a RAS mutation (Tanaka et al., 2007). The crystal structure of the intrabody bound to mutant RAS, solved to 2 Å, shows that the intrabody specifically recognises the conformational structure of oncogenic RAS and inhibits RAS-effector protein interactions with RAS.

Nonetheless, there are currently few small-molecule drugs in clinical trials that are capable of impeding protein interactions, since these generally require clefts in a protein into which a small molecule can fit (Blundell et al, 2006).

There is a need in the art for the development of novel approaches to target protein-protein interactions. In particular, there is a need in the art for the provision of molecules capable of penetrating cells and which can bind to RAS and inhibit protein-protein interactions, in particular aberrant RAS-effector interactions, with high affinity and/or specificity. Such molecules represent promising treatments for proliferative disorders such as cancer.

SUMMARY OF THE INVENTION

In one aspect, the present invention provides a compound as defined herein, and/or a salt or solvate thereof.

In another aspect, the present invention provides a pharmaceutical composition which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer.

In another aspect, the present invention provides a compound as defined herein, or a pharmaceutically acceptable salt or solvate thereof, or a pharmaceutical composition as defined herein, for use in inhibiting a RAS-effector protein-protein interaction.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer.

In another aspect, the present invention provides the use of a compound as defined herein, or a pharmaceutically acceptable salt or solvate thereof, in the manufacture of a medicament for use in inhibiting a RAS-effector protein-protein interaction.

In another aspect, the present invention provides a method of inhibiting a RAS-effector protein-protein interaction in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a combination comprising a compound, or a pharmaceutically acceptable salt or solvate thereof, as defined herein, with one or more additional therapeutic agents.

Preferred, suitable, and optional features of any one particular aspect of the present invention are also preferred, suitable, and optional features of any other aspect.

DETAILED DESCRIPTION OF THE INVENTION

Definitions

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I" and the more general term "compounds" refer to and include any and all compounds described by and/or with reference to Formula I. It should also be understood that these terms encompasses all stereoisomers, i.e. cis and trans isomers, as well as optical isomers, i.e. R and S enantiomers, of such compounds and all salts thereof, in substantially pure form and/or any mixtures of the foregoing in any ratio. This understanding extends to pharmaceutical compositions and methods of treatment that employ or comprise one or more compounds of the Formula I, either by themselves or in combination with additional agents.

The various hydrocarbon-containing moieties provided herein may be described using a prefix designating the minimum and maximum number of carbon atoms in the moiety, e.g. "$(C_{a-b})$" or "$C_a$–$C_b$" or "(a–b)C". For example, $(C_{a-b})$alkyl indicates an alkyl moiety having the integer "a" to the integer "b" number of carbon atoms, inclusive. Certain moieties may also be described according to the minimum and maximum number of members with or without specific reference to a particular atom or overall structure. For example, the terms "a to b membered ring" or "having between a to b members" refer to a moiety having the integer "a" to the integer "b" number of atoms, inclusive.

"About" when used herein in conjunction with a measurable value such as, for example, an amount or a period of time and the like, is meant to encompass reasonable variations of the value, for instance, to allow for experimental error in the measurement of said value.

As used herein by themselves or in conjunction with another term or terms, "alkyl" and "alkyl group" refer to a branched or unbranched saturated hydrocarbon chain. Unless specified otherwise, alkyl groups typically contain 1-10 carbon atoms, such as 1-6 carbon atoms or 1-4 carbon atoms or 1-3 carbon atoms, and can be substituted or unsubstituted. Representative examples include, but are not limited to, methyl, ethyl, n-propyl, i-propyl, n-butyl, i-butyl, s-butyl, t-butyl, n-pentyl, n-hexyl, n-heptyl, n-octyl, n-nonyl, n-decyl, isopropyl, tert-butyl, isobutyl, etc.

As used herein by themselves or in conjunction with another term or terms, "alkylene" and "alkylene group" refer to a branched or unbranched saturated hydrocarbon chain. Unless specified otherwise, alkylene groups typically contain 1-10 carbon atoms, such as 1-6 carbon atoms or 1-3 carbon atoms, and can be substituted or unsubstituted. Representative examples include, but are not limited to, methylene (—$CH_2$—), the ethylene isomers (—$CH(CH_3)$— and —$CH_2CH_2$—), the propylene isomers (—$CH(CH_3)CH_2$—, —$CH(CH_2CH_3)$—, —$C(CH_3)_3$—, and —$CH_2CH_2CH_2$—), etc.

As used herein by themselves or in conjunction with another term or terms, "alkenyl" and "alkenyl group" refer to a branched or unbranched hydrocarbon chain containing at least one double bond. Unless specified otherwise, alkenyl groups typically contain 2-10 carbon atoms, such as 2-6 carbon atoms or 2-4 carbon atoms, and can be substituted or unsubstituted. Representative examples include, but are not limited to, ethenyl, 3-buten-1-yl, 2-ethenylbutyl, and 3-hexen-1-yl.

As used herein by themselves or in conjunction with another term or terms, "alkynyl" and "alkynyl group" refer to a branched or unbranched hydrocarbon chain containing at least one triple bond. Unless specified otherwise, alkynyl groups typically contain 2-10 carbon atoms, such as 2-6 carbon atoms or 2-4 carbon atoms, and can be substituted or unsubstituted. Representative examples include, but are not limited to, ethynyl, 3-butyn-1-yl, propynyl, 2-butyn-1-yl, and 3-pentyn-1-yl.

As used herein by itself or in conjunction with another term or terms, "aromatic" refers to monocyclic and polycyclic ring systems containing 4n+2 pi electrons, where n is an integer. Aromatic should be understood as referring to and including ring systems that contain only carbon atoms (i.e. "aryl") as well as ring systems that contain at least one heteroatom selected from N, O or S (i.e. "heteroaromatic" or "heteroaryl"). An aromatic ring system can be substituted or unsubstituted.

As used herein by itself or in conjunction with another term or terms, "non-aromatic" refers to a monocyclic or polycyclic ring system having at least one double bond that is not part of an extended conjugated pi system. As used herein, non-aromatic refers to and includes ring systems that contain only carbon atoms as well as ring systems that contain at least one heteroatom selected from N, O or S. A non-aromatic ring system can be substituted or unsubstituted.

As used herein by themselves or in conjunction with another term or terms, "aryl" and "aryl group" refer to phenyl and 7-15 membered bicyclic or tricyclic hydrocarbon ring systems, including bridged, spiro, and/or fused ring systems, in which at least one of the rings is aromatic. In fused systems in which at least one ring is aromatic the point of attachment to the remainder of the molecule can be at any suitable part on the fused ring system including aromatic or non-aromatic parts. Aryl groups can be substituted or unsubstituted. Unless specified otherwise, an aryl group may contain 6 ring atoms (i.e., phenyl) or a ring system containing 9 to 15 atoms, such as 9 to 11 ring atoms, or 9 or 10 ring atoms. Representative examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Suitably an aryl group is phenyl and naphthyl, suitably phenyl.

As used herein by themselves or in conjunction with another term or terms, "arylene" and "arylene group" refer to a phenylene (—$C_6H4$-) or to 7 to 15 membered bicyclic or tricyclic hydrocarbon ring systems, including bridged, spiro, and/or fused ring systems, in which at least one of the rings is aromatic. Arylene groups can be substituted or unsubstituted. In some embodiments, an arylene group may contain 6 (i.e., phenylene) ring atoms or be a ring system containing 9 to 15 atoms; such as 9 to 11 ring atoms; or 9 or 10 ring atoms. Arylene groups can be substituted or unsubstituted.

As used herein by themselves or in conjunction with another term or terms, "alkylaryl" and "alkylaryl group" refer to an alkyl group in which a hydrogen atom is replaced by an aryl group, wherein alkyl group and aryl group are as previously defined, such as, for example, benzyl ($C_6H_5CH_2$—). Alkylaryl groups can be substituted or unsubstituted. Suitably, the alkylaryl group is a $C_6$ alkylphenyl group.

As used herein by themselves or in conjunction with another term or terms, "carbocyclic group" and "carbocycle" refer to monocyclic and polycyclic ring systems that contain only carbon atoms in the ring(s), i.e., hydrocarbon ring systems, without regard or reference to aromaticity or degree of unsaturation. Thus, carbocyclic group should be understood as referring to and including ring systems that are fully saturated (such as, for example, a cyclohexyl group), ring systems that are aromatic (such as, for example, a phenyl group), as well as ring systems having fully saturated, aromatic and/or unsaturated portions (such as, for example, cyclohexenyl, 2,3-dihydro-indenyl, and 1,2,3,4-tetrahydro-naphthalenyl). The terms carbocyclic and carbocycle further include bridged, fused, and spirocyclic ring systems.

As used herein by themselves or in conjunction with another term or terms, "cycloalkyl" and "cycloalkyl group" refer to a non-aromatic carbocyclic ring system, that may be monocyclic, bicyclic, or tricyclic, saturated or unsaturated, and may be bridged, spiro, and/or fused. A cycloalkyl group may be substituted or unsubstituted. Unless specified otherwise, a cycloalkyl group typically contains from 3 to 12 ring atoms. In some instances a cycloalkyl group may contain 4 to 10 ring atoms (e.g., 4 ring atoms, 5 ring atoms, 6 ring atoms, 7 ring atoms, etc.). Representative examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane. Suitably, cycloalkyl groups are selected from cyclopropyl, cyclobutyl, cyclopentyl and cyclohexyl groups.

As used herein by themselves or in conjunction with another term or terms, "alkylcycloalkyl" and "alkylcycloalkyl group" refer to an alkyl group in which a hydrogen atom is replaced by a cycloalkyl group, wherein alkyl group and cycloalkyl group are as previously defined, such as, for example, cyclohexylmethyl ($C_6H_{11}CH_2$—). Alkylcycloalkyl groups can be substituted or unsubstituted. Suitably, the alkylcycloalkyl group is a $C_{1-6}$ alkyl-$C_{3-6}$ cycloalkyl group.

As used herein by themselves or in conjunction with another term or terms, "haloalkyl" and "haloalkyl group" refer to alkyl groups in which one or more hydrogen atoms are replaced by halogen atoms. Haloalkyl includes both saturated alkyl groups as well as unsaturated alkenyl and alkynyl groups. Representative examples include, but are not limited to, —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CI=$CH_2$, —C≡C—$CF_3$, —$CHFCH_2CH_3$ and —$CHFCH_2CF_3$. Haloalkyl groups can be substituted or unsubstituted. Suitably, a haloalkyl group is selected from $CHF_2$ and $CF_3$, suitably $CF_3$.

As used herein by themselves or in conjunction with another term or terms, "haloalkoxy" and "haloalkoxy group" refer to alkoxy groups (i.e. O-alkyl groups) in which one or more hydrogen atoms are replaced by halogen atoms. Haloalkoxy includes both saturated alkoxy groups as well as unsaturated alkenyl and alkynyl groups. Representative examples include, but are not limited to, —$OCF_3$, —$OCHF_2$, —$OCH_2F$, —$OCF_2CF_3$, —$OCHFCF_3$, —$OCH_2CF_3$, —$OCF_2CH_3$, —$OCHFCH_3$, —$OCF_2CF_2CF_3$, —$OCF_2CH_2CH_3$, —OCF=$CF_2$, —OCCl=$CH_2$, —OCBr=$CH_2$, —$OCHFCH_2CH_3$ and —$OCHFCH_2CF_3$. Haloalkoxy groups can be substituted or unsubstituted. Suitably, a haloalkyoxy group is selected from —$OCHF_2$ and —$OCF_3$, suitably —$OCF_3$.

As used herein by themselves or in conjunction with another term or terms, "halo" and "halogen" include fluorine, chlorine, bromine and iodine atoms and substituents. Suitably, the halogen is selected from fluorine, chlorine and bromine, more suitably fluorine and chlorine.

As used herein by themselves or in conjunction with another term or terms, "heteroaryl" and "heteroaryl group" refer to (a) 5 and 6 membered monocyclic aromatic rings, which contain, in addition to carbon atom(s), at least one heteroatom, such as nitrogen, oxygen or sulfur, and (b) 7 to 15 membered bicyclic and tricyclic rings, which contain, in addition to carbon atom(s), at least one heteroatom, such as nitrogen, oxygen or sulfur, and in which at least one of the rings is aromatic. In some instances, a heteroaryl group can contain two or more heteroatoms, which may be the same or different. Heteroaryl groups can be substituted or unsubstituted, and may be bridged, spiro, and/or fused. In some instances, a heteroaryl group may contain 5, 6, or 8 to 15 ring atoms. In other instances, a heteroaryl group may contain 5 to 10 ring atoms, such as 5, 6, 9, or 10 ring atoms. Representative examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.0$^{2,7}$]dodeca-2(7),3,5-trienyl, 12-oxa-10-aza-tricyclo[6.3.1.0$^{2,7}$]dodeca-2(7),3,5-trienyl, 12-aza-tricyclo[7.2.1.0$^{2,7}$]dodeca-2(7),3,5-trienyl, 10-aza-tricyclo[6.3.2.0$^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Suitably, a heteroaryl is a 5- or 6-membered heteroaryl ring comprising one, two or three heteroatoms selected from N, O or S.

As used herein by themselves or in conjunction with another term or terms, "alkylheteroaryl" and "alkylheteroaryl group" refer to an alkyl group in which a hydrogen atom is replaced by a heteroaryl group, wherein alkyl group and heteroaryl group are as previously defined. Alkylheteroaryl groups can be substituted or unsubstituted. Where carbon numbers and number of members are provided, e.g. X-Y membered (C$_{n-m}$)alkylheteroaryl, the carbon range refers to the alkyl group only and the number of members refers to the heteroaryl group. Suitably, the constituent alkyl group has 1-6 carbons, suitable 1-3 carbons. Suitably, the heteroaryl group is 5-6 membered.

As used herein by themselves or in conjunction with another term or terms, "heterocyclic group" and "heterocycle" refer to monocyclic and polycyclic ring systems that contain carbon atoms and at least one heteroatom selected from nitrogen, oxygen, sulfur or phosphorus in the ring(s), without regard or reference to aromaticity or degree of unsaturation. Thus, a heterocyclic group should be understood as referring to and including ring systems that are fully saturated (such as, for example, a piperidinyl group), ring systems that are aromatic (such as, for example, a pyridinyl group), as well as ring systems having fully saturated, aromatic and/or unsaturated portions (such as, for example, 1,2,3,6-tetrahydropyridinyl and 6,8-dihydro-5H-[1,2,4]triazolo[4,3-a]pyrizinyl). The terms heterocyclic and heterocycle further include bridged, fused, and spirocyclic ring systems.

As used herein by themselves or in conjunction with another term or terms, "heterocycloalkyl" and "heterocycloalkyl group" refer to 3 to 15 membered monocyclic, bicyclic, and tricyclic non-aromatic ring systems, which contain, in addition to carbon atom(s), at least one heteroatom, such as nitrogen, oxygen, sulfur or phosphorus. Heterocycloalkyl groups may be fully saturated or contain unsaturated portions and may be bridged, spiro, and/or fused ring systems. In some instances a heterocycloalkyl group may contain at least two or heteroatoms, which may be the same or different. Heterocycloalkyl groups can be substituted or unsubstituted. In some instances a heterocycloalkyl group may contain from 3 to 10 ring atoms or from 3 to 7 ring atoms or from 5 to 7 ring atoms, such as 5 ring atoms, 6 ring atoms, or 7 ring atoms. Representative examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-aza-bicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2]nonanyl, [1,4]oxaphosphinanyl-4-oxide, [1,4]azaphosphinanyl-4-oxide, [1,2]oxaphospholanyl-2-oxide, phosphinanyl-1-oxide, [1,3]azaphospholidinynl-3-oxide, [1,3]oxaphospholanyl-3-oxide, 7-oxabicyclo[2.2.1]heptanyl, 6,8-dihydro-5H-[1,2,4]triazolo[4,3-a]pyrazin-7-yl, 6,8-dihydro-5H-imidazo[1,5-a]pyrazin-7-yl, 6,8-dihydro-5H-imidazo[1,2-a]pyrazin-7-yl, 5,6,8,9-tetrahydro-[1,2,4]triazolo[4,3-d][1,4]diazepin-7-yl and 6,8-dihydro-5H-[1,2,4]triazolo[4,3-a]pyrazin-7-yl. Suitably, a heterocyclylalkyl group as defined herein is a monocyclic, bicyclic or spiro heterocyclyl group comprising one, two or three heteroatoms selected from N, O or S.

As used herein by themselves or in conjunction with another term or terms, "heterocycloalkylene" and "heterocycloalkylene group" refer to 3 to 15 membered monocyclic, bicyclic, or tricyclic non-aromatic ring systems, which contain, in addition to carbon atom(s), at least one heteroatom, such as nitrogen, oxygen, sulfur or phosphorus. Heterocycloalkylene groups may be fully saturated or contain unsaturated portions and may be bridged, spiro, and/or fused. Heterocycloalkylene groups can be substituted or unsubstituted. In some instances, a heterocycloalkylene group may contain from 3 to 10 ring atoms; such as from 3 to 7 ring atoms. In other instances a heterocycloalkylene group may contain from 5 to 7 ring atoms, such as 5 ring atoms, 6 ring atoms, or 7 ring atoms.

As used herein by themselves or in conjunction with another term or terms, "alkylheterocycloalkyl" and "alkylheterocycloalkyl group" refer to an alkyl group in which a hydrogen atom is replaced by a heterocycloalkyl group, wherein alkyl group and heterocycloalkyl group are as previously defined, such as, for example, pyrrolidinylmethyl (C₄H₃NCH₂—). Alkylheteroycloalkyl groups can be substituted or unsubstituted. Where carbon numbers and number of members are provided, e.g. X-Y membered ($C_{n-m}$)alkylheterocycloalkyl, the carbon range refers to the alkyl group only and the number of members refers to the heterocycloalkyl group. Suitably, the constituent alkyl group has 1-6 carbons, suitable 1-3 carbons. Suitably, the heterocycloalkyl group is 3-7 membered, more suitably 3-6 membered, more suitably 5-6 membered.

As used herein by itself or in conjunction with another term or terms, "pharmaceutically acceptable" refers to materials that are generally chemically and/or physically compatible with other ingredients (such as, for example, with reference to a formulation), and/or is generally physiologically compatible with the recipient (such as, for example, a subject) thereof.

As used herein by itself or in conjunction with another term or terms, "pharmaceutical composition" refers to a composition that can be used to treat a disease, condition, or disorder in a subject, including a human.

As used herein by itself or in conjunction with another term or terms, "pseudohalogen" refers to —OCN, —SCN, —CF₃, and —CN.

As used herein by themselves or in conjunction with another term or terms, "stable" and "chemically stable" refer to a compound that is sufficiently robust to be isolated from a reaction mixture with a useful degree of purity. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, when considering the degree of optional substitution of a particular moiety, it should be understood that the number of substituents does not exceed the valency appropriate for that moiety. For example, if $R^1$ is a methyl group (—CH₃), it can be optionally substituted by 1 to 3 $R^5$.

As used herein by themselves or in conjunction with another term or terms, "subject(s)" and "patient(s)", suitably refer to mammals, in particular humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s).

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", refer to and include prophylactic, ameliorative, palliative, and curative uses and results. In some embodiments, the terms "treating", "treated", and "treatment" refer to curative uses and results as well as uses and results that diminish or reduce the severity of a particular condition, characteristic, symptom, disorder, or disease described herein. For example, treatment can include diminishment of several symptoms of a condition or disorder or complete eradication of said condition or disorder. It should be understood that the term "prophylactic" as used herein is not absolute but rather refers to uses and results where the administration of a compound or composition diminishes the likelihood or seriousness of a condition, symptom, or disease state, and/or delays the onset of a condition, symptom, or disease state for a period of time.

As used herein, a "therapeutically active agent", whether used alone or in conjunction with another term or terms, refers to any compound, i.e. a drug, that has been found to be useful in the treatment of a disease, disorder or condition and is not described by Formula I.

It should be understood that a therapeutically active agent may not be approved by the FDA or an equivalent foreign regulatory body.

A "therapeutically effective amount" means the amount of a compound that, when administered to a subject or patient for treating a disease, is sufficient to effect such treatment for the disease. The "therapeutically effective amount" will vary depending on the compound, the disease and its severity and the age, weight, etc., of the subject or patient to be treated.

As used herein, the term "direct bond" means that the two groups adjacent a direct bond (e.g. in the case of $J^1$ being a direct bond, $(CR^eR^f)_a$ and $(CR^gR^h)_b$) are directly linked, (i.e. $(CR^eR^f)_a$—$(CR^gR^h)_b$).

Compounds

Aspects and embodiments of the invention will now be described at least by way of the following numbered paragraphs:

1. A compound of formula I, or a salt or solvate thereof:

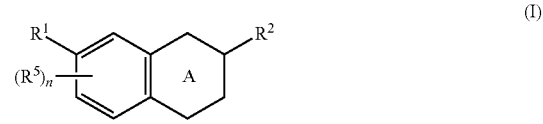

(I)

wherein,
ring A is a 6-membered fused ring selected from the group consisting of fused phenyl, fused pyridyl, fused tetrahydropyranyl, fused 1,4-dioxanyl, fused piperidinyl and fused morpholinyl;

$R^5$ is selected from hydrogen, hydroxyl, halogen, CN, $C_{1-6}$haloalkyl, $C_{1-6}$ haloalkoxy, O—$C_{1-6}$alkyl and $C_{1-3}$alkyl;
n is a number selected from 0, 1, 2, and 3;
$R^1$ is selected from a group of formula II:

(II)

wherein
R$^e$, R$^f$, R$^g$, and R$^h$ are independently selected from hydrogen and C$_{1-6}$ alkyl;

J$^1$ is selected from direct bond, O, S, CH$_2$ and NR$^s$; where R$^s$ is selected from hydrogen and C$_{1-6}$ alkyl;

$_a$ and $_b$ are independently selected from 0, 1, 2, 3 and 4;

A$^1$ is selected from C$_{3-11}$ cycloalkyl optionally substituted by one or more R$^k$, C$_{6-11}$ aryl optionally substituted by one or more R$^k$, 3-15 membered heterocycloalkyl optionally substituted by one or more R$^k$, and 5-15 membered heteroaryl optionally substituted by one or more R$^k$;

R$^k$ is selected from hydrogen, hydroxyl, =O, halogen, CN, C$_{1-6}$ haloalkyl, C$_{1-6}$ haloalkoxy, C$_{1-6}$ alkyl, O—C$_{1-6}$ alkyl, C$_{3-6}$ cycloalkyl, 3-10 membered heterocycloalkyl, phenyl, benzyl, alkylheteroaryl, —C(=O)R$^d$, —(=O)OR$^d$, —C(=O)NR$^c$R$^d$, —C(O)C(=O)R$^d$, —NR$^c$R$^d$, —NR$^c$C(=O)R$^d$, —NR$^c$C(=O)OR$^d$, —NR$^c$C(=O)NR$^c$R$^d$, —NR$^c$S(=O)$_2$R$^d$, —NR$^c$S(=O)$_2$NR$^c$R$^d$, OR$^d$, —SR$^d$, —O(=O)R$^d$, —OC(=O)NR$^c$R$^d$, —OC(=O)OR$^d$, S(=O)$_2$R$^d$, —S(=O)R$^d$, —OS(=O)R$^d$, —OS(=O)$_2$R$^d$, OS(O)$_2$OR$^d$, —S(=O)NR$^c$R$^d$, OS(=O)$_2$NR$^c$R$^d$, S(=O)$_2$NR$^c$R$^d$; where said C$_{3-6}$ cycloalkyl, C$_{1-6}$alkyl, 3-10 membered heterocycloalkyl, phenyl, benzyl, alkylheteroaryl, and O—C$_{1-6}$ alkyl are optionally substituted with one or more groups selected from hydroxyl, halogen, =O, CN, C$_{1-3}$ haloalkyl, C$_{1-6}$ haloalkoxy, C$_{3-6}$ cycloalkyl, NR$^c$R$^d$, C$_{1-6}$ alkyl, O—C$_{1-6}$ alkyl, and phenyl;

R$^2$ is selected from —C(=O)NR$^c$R$^d$, —NR$^c$C(=O)R$^d$, —NR$^c$C(=O)OR$^d$, —NR$^c$C(=O)NR$^c$R$^d$, —NR$^c$S(=O)$_2$R$^d$, —NR$^c$S(=O)$_2$NR$^c$R$^d$, C$_{1-10}$alkyl optionally substituted by one or more R$^n$, C$_{2-6}$alkenyl optionally substituted by one or more R$^n$, C$_{2-6}$alkynyl optionally substituted by one or more R$^n$, or a group of Formula III

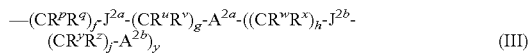

—(CR$^p$R$^q$)$_f$-J$^{2a}$-(CR$^u$R$^v$)$_g$-A$^{2a}$-((CR$^w$R$^x$)$_h$-J$^{2b}$-(CR$^y$R$^z$)$_j$-A$^{2b}$)$_y$    (III)

wherein R$^n$ is independently selected from hydroxyl, =O, halogen, CN, C$_{1-6}$ haloalkyl, C$_{1-6}$ haloalkoxy, C$_{1-6}$ alkyl, O—C$_{1-6}$ alkyl, C$_{3-6}$ cycloalkyl, 3-11 membered heterocycloalkyl, —C(=O)R$^d$, —C(=O)OR$^d$, —C(=O)NR$^c$R$^d$, —C(O)C(=O)R$^d$, —NR$^c$R$^d$, —NR$^c$C(=O)R$^d$, —NR$^c$C(=O)OR$^d$, —NR$^c$C(=O)NR$^c$R$^d$, —NR$^c$S(=O)$_2$R$^d$, —NR$^c$S(=O)$_2$NR$^c$R$^d$, —OR$^d$, —SR$^d$, —OC(=O)R$^d$, —OC(=O)NR$^c$R$^d$, —O(=O)OR$^d$, —S(=O)$_2$R$^d$, S(=O)$_2$R$^d$, OS(=O)R$^d$, —OS(=O)$_2$R$^d$, —OS(=O)$_2$OR$^d$, —S(=O)NR$^c$R$^d$, —OS(=O)$_2$NR$^c$R$^d$ and —S(=O)$_2$NR$^c$R$^d$; where said C$_{3-6}$cycloalkyl, C$_{1-6}$alkyl, 3-11 membered heterocycloalkyl, C$_{1-6}$ alkyl and O—C$_{1-6}$alkyl are optionally substituted with one or more groups selected from hydroxyl, halogen, =O, CN, C$_{1-6}$ haloalkyl, C$_{1-6}$ haloalkoxy, C$_{3-6}$ cycloalkyl, NR$^c$R$^d$, C$_{1-6}$alkyl, and O—C$_{1-6}$alkyl; and R$^p$, R$^q$, R$^u$ and R$^v$, are independently selected from hydrogen, C$_{1-6}$ alkyl, C(O)NR$^c$R$^d$, C$_{3-7}$cycloalkyl optionally substituted by one or more R$^b$, (C$_{1-6}$alkyl)phenyl optionally substituted by one or more R$^b$, phenyl optionally substituted by one or more R$^b$, (C$_{1-6}$alkyl)C$_{3-7}$cycloalkyl optionally substituted by one or more R$^b$, 3-7 membered heterocycloalkyl optionally substituted by one or more R$^b$, 3-7 membered (C$_{1-6}$alkyl)heterocycloalkyl optionally substituted by one or more R$^b$, 5-6 membered heteroaryl optionally substituted by one or more R$^b$, and 5-6 membered (C$_{1-6}$alkyl)heteroaryl optionally substituted by one or more R$^b$;

R$^w$, R$^x$, R$^y$, R$^z$ are independently selected from hydrogen and C$_{1-6}$ alkyl;

$_f$, $_g$, $_h$, and $_j$ are independently selected from 0, 1, 2, 3 and 4; and $_y$ is selected from 0 and 1;

J$^{2a}$ is selected from a direct bond, O, S, C(O), CH$_2$, C(O)NR$^{s1}$, NR$^{s1}$C(O), NR$^{s1}$C(O)NR$^{s1}$ and NR$^{s1}$; where R$^{s1}$ is selected from hydrogen, C$_{1-6}$ alkyl, C$_{3-7}$cycloalkyl optionally substituted by one or more R$^b$, (C$_{1-6}$alkyl)phenyl optionally substituted by one or more R$^b$, phenyl optionally substituted by one or more R$^b$, (C$_{1-6}$alkyl)C$_{3-7}$cycloalkyl optionally substituted by one or more R$^b$, 3-7 membered heterocycloalkyl optionally substituted by one or more R$^b$, 3-7 membered (C$_{1-6}$alkyl)heterocycloalkyl optionally substituted by one or more R$^b$, 5-6 membered heteroaryl optionally substituted by one or more R$^b$, and 5-6 membered (C$_{1-6}$alkyl)heteroaryl optionally substituted by one or more R$^b$;

J$^{2b}$ is selected from a direct bond, O, S, C(O), CH$_2$, C(O)NR$^{s2}$, NR$^{s2}$C(O) and NR$^{s2}$; where R$^{s2}$ is selected from hydrogen, C$_{1-6}$ alkyl, C$_{3-7}$cycloalkyl optionally substituted by one or more R$^b$, (C$_{1-6}$alkyl)phenyl optionally substituted by one or more R$^b$, phenyl optionally substituted by one or more R$^b$, (C$_{1-6}$alkyl)C$_{3-7}$cycloalkyl optionally substituted by one or more R$^b$, 3-7 membered heterocycloalkyl optionally substituted by one or more R$^b$, 3-7 membered (C$_{1-6}$alkyl)heterocycloalkyl optionally substituted by one or more R$^b$, 5-6 membered heteroaryl optionally substituted by one or more R$^b$, and 5-6 membered (C$_{1-6}$alkyl)heteroaryl optionally substituted by one or more R$^b$;

each R$^b$ is independently selected from hydroxyl, =O, halogen, C$_{1-6}$ alkyl, CN, C$_{1-6}$ haloalkyl, C$_{1-6}$ haloalkoxy, C$_{3-6}$ cycloalkyl, OR$^d$, 3-10 membered heterocycloalkyl, wherein said C$_{1-6}$ alkyl, C$_{3-6}$ cycloalkyl and 3-10 membered heterocycloalkyl are optionally substituted with one or more groups selected from hydroxyl, halogen, CN, NR$^c$R$^d$, C$_{1-6}$ haloalkyl, C$_{3-6}$ cycloalkyl, C$_{1-6}$ alkyl, phenyl and O—C$_{1-6}$ alkyl;

A$^{2a}$ is selected from C$_{3-11}$ cycloalkyl optionally substituted by one or more R$^t$, 3-15 membered heterocycloalkyl optionally substituted by one or more R$^t$, C$_{6-11}$ aryl optionally substituted by one or more R$^t$, 5-15 membered heteroaryl optionally substituted by one or more R$^t$;

A$^{2b}$ is selected from C$_{3-11}$ cycloalkyl optionally substituted by one or more R$^t$, 3-15 membered heterocycloalkyl optionally substituted by one or more R$^t$, C$_{6-11}$ aryl optionally substituted by one or more R$^t$, 5-15 membered heteroaryl optionally substituted by one or more R$^t$; and R$^t$ is selected from hydroxyl, =O, halogen, CN, C$_{1-6}$ haloalkyl, C$_{1-6}$ haloalkoxy, C$_{1-6}$ alkyl, O—C$_{1-6}$ alkyl, C$_{3-6}$ cycloalkyl, 5-6 membered heteroaryl, 3-7 membered heterocycloalkyl, —C(=O)R$^d$, —(=O)OR$^d$, —C(=O)NR$^c$R$^d$, (O)C(=O)R$^d$, —NR$^c$R$^d$, —NR$^c$C(=O)R$^d$, —NR$^c$C(=O)OR$^d$, —NR$^c$C(=O)NR$^c$R$^d$, —NR$^c$S(=O)$_2$R$^d$, —NR$^c$S(=O)$_2$NR$^c$R$^d$, R$^d$, SR$^d$, —OC(=O)R$^d$, —OC(=O)NR$^c$R$^d$, —OC(=O)OR$^d$, —S(=O)$_2$R$^d$, —S(=O)R$^d$, —OS(=O)R$^d$, OS(o)$_2$R$^d$, —OS(=O)$_2$OR$^d$, —S(=O)NR$^c$R$^d$, —OS(=O)$_2$NR$^c$R$^d$, —S(=O)$_2$NR$^c$R$^d$; where said C$_{3-6}$ cycloalkyl, C$_{1-6}$ alkyl, 5-6 membered heteroaryl, 3-7 membered heterocycloalkyl, C$_{1-6}$ alkyl and O—C$_{1-6}$alkyl are optionally substituted with one or more groups selected from hydroxyl, halogen, =O, CN, C$_{1-6}$ haloalkyl, C$_{1-6}$ haloalkoxy, C$_{3-6}$ cycloalkyl, C(O)NR$^c$R$^d$, NR$^c$R$^d$, C$_{1-6}$ alkyl, and O—C$_{1-6}$ alkyl; and wherein,
each R$^c$ is independently selected from hydrogen, hydroxyl, halogen, CN, C$_{1-6}$ haloalkyl, C$_{3-6}$ cycloalkyl, C$_{1-6}$ alkyl and O—C$_{1-6}$ alkyl;

each R$^d$ is independently selected from hydrogen, hydroxyl, halogen, CN, C$_{1-6}$ haloalkyl, 3-7 membered heterocycloalkyl, C$_{3-6}$ cycloalkyl, C$_{1-6}$ alkyl, O—C$_{1-6}$ alkyl, C(=O)O(C$_{1-6}$ alkyl), 5-6 membered heteroaryl and phenyl, wherein said C$_{1-6}$ alkyl, O—C$_{1-6}$ alkyl, phenyl, 3-7 membered heterocycloalkyl, 5-6 membered heteroaryl and C$_{3-6}$ cycloalkyl are optionally substituted with one or more groups selected from hydroxyl, =O, halogen, CN, NH$_2$, NHMe, NMe$_2$, C$_{1-6}$ haloalkyl, C$_{3-6}$ cycloalkyl, C$_{6-11}$ aryl, C$_{1-6}$ alkyl and O—C$_{1-6}$ alkyl; or R$^c$ and R$^d$, when attached to the same atom, together with the atom to which they are attached form a 3-10 membered ring, optionally containing one or more for heteroatoms selected from O, N and S, and wherein said ring is optionally substituted with one or more R$^m$; and R$^m$ is selected from hydrogen, hydroxyl, =O, halogen, C$_{1-6}$ alkyl, CN, C$_{1-6}$ haloalkyl, C$_{1-6}$ haloalkoxy, C$_{3-6}$ cycloalkyl, OR$^d$, 3-10 membered heterocycloalkyl, 5-6 membered (C$_{1-6}$ alkyl)heterocycloalkyl 5-6 membered (C$_{1-6}$ alkyl)heteroaryl wherein said C$_{1-6}$ alkyl, C$_{3-6}$ cycloalkyl, 3-10 membered heterocycloalkyl, 5-6 membered (C$_{1-6}$ alkyl)heterocycloalkyl, and 5-6 membered (C$_{1-6}$ alkyl)heteroaryl are optionally substituted with one or more groups selected from hydroxyl, halogen, CN, NH$_2$, NHMe, NMe$_2$, C$_{1-6}$ haloalkyl, C$_{3-6}$ cycloalkyl, C$_{1-6}$ alkyl, phenyl, and O—C$_{1-6}$ alkyl.

In one embodiment, ring A may be a fused phenyl group. Accordingly, in this embodiment, the compounds of formula I can be represented by sub-formula (I-i):

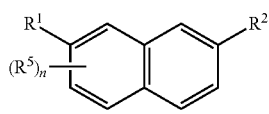

(I-i)

In one embodiment, ring A may be a fused pyridyl group. Accordingly, in this embodiment, the compounds of formula I can be represented by sub-formulae (I-ii) and (I-iii):

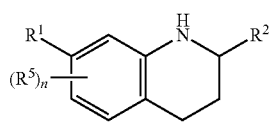

(I-ii)

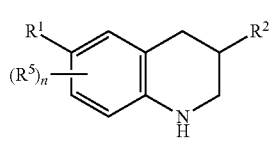

(I-iii)

In one embodiment, ring A may be a fused pyridyl group. Accordingly, in this embodiment, the compounds of formula I can be represented by sub-formulae (I-iv) and (1-v):

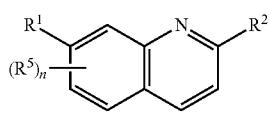

(I-iv)

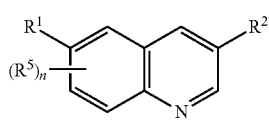

(I-v)

In one embodiment, ring A may be a fused 1,4-dioxan group. Accordingly, in this embodiment, the compounds of formula I can be represented by sub-formula (I-vi):

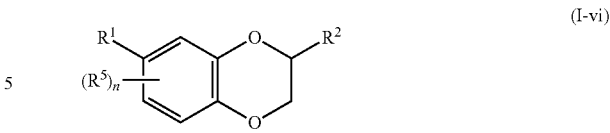

(I-vi)

In one embodiment, ring A may be a fused piperidinyl group. Accordingly, in this embodiment, the compounds of formula I can be represented by sub-formulae (I-vii) and (I-viii):

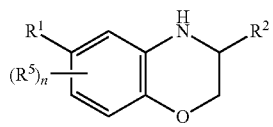

(I-vii)

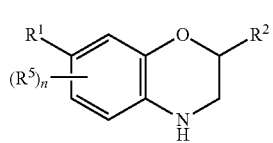

(I-viii)

In one embodiment, ring A may be a fused morpholinyl group. Accordingly, in this embodiment, the compounds of formula I can be represented by sub-formulae (I-ix) and (I-x):

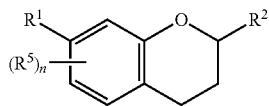

(I-ix)

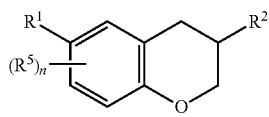

(I-x)

In one embodiment, the compound of formula (I) is selected from a compound of sub-formulae selected from the groups consisting of I-i, I-ii, I-iii, I-iv, I-v, I-vi, I-vii, I-viii, I-ix and I-x.

In another embodiment, the compound of formula (I) is selected from a compound of sub-formulae selected from the groups consisting of I-iv, I-v, I-vi, I-vii, I-viii, I-ix and I-x.

In another embodiment, the compound of formula (I) is selected from a compound of sub-formulae selected from the groups consisting of I-iv, I-v, I-vi, I-ix and I-x.

In another embodiment, the compound of formula (I) is selected from a compound of sub-formulae selected from the groups consisting of I-vi, I-ix and I-x.

In another embodiment, the compound of formula (I) is selected from a compound of sub-formula I-vi.

2. A compound, or a salt or solvate thereof, of sub-formula Ia:

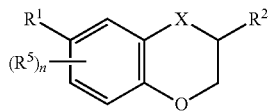

wherein,

X is selected from $NR^3$, $CR^4$ and O; where $R^3$ and $R^4$ are independently selected from hydrogen and $C_{1-6}$ alkyl;

$R^5$ is selected from hydrogen, hydroxyl, halogen, CN, $C_{1-6}$ haloalkyl, $C_{1-6}$ haloalkoxy, O—$C_{1-6}$ alkyl and $C_{1-6}$ alkyl;

n is a number selected from 0, 1, 2, and 3;

$R^1$ is selected from a group of formula II:

$$A^1\text{-}(CR^eR^f)_a\text{-}J^1\text{-}(CR^gR^h)_b\text{—} \quad (II)$$

wherein $R^e$, $R^f$, $R^g$, and $R^h$ are independently selected from hydrogen and $C_{1-6}$ alkyl;

$J^1$ is selected from direct bond, O, S, $CH_2$ and NRs; where $R^s$ is selected from hydrogen and $C_{1-6}$ alkyl;

$a$ and $b$ are independently selected from 0, 1, 2, 3 and 4;

$A^1$ is selected from $C_{3-11}$ cycloalkyl optionally substituted by one or more $R^k$, $C_{6-11}$ aryl optionally substituted by one or more $R^k$, 3-15 membered heterocycloalkyl optionally substituted by one or more $R^k$, and 5-15 membered heteroaryl optionally substituted by one or more $R^k$;

$R^k$ is selected from hydrogen, hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-10 membered heterocycloalkyl, phenyl, benzyl, alkylheteroaryl, —C(=O)$R^d$, —C(=O)O$R^d$, —C(=O)N$R^cR^d$, —C(O)C(=O)$R^d$, —N$R^cR^d$, —N$R^cC$(=O)$R^d$, —N$R^cC$(=O)O$R^d$, —N$R^cC$(=O)N$R^cR^d$, —N$R^cS$(=O)$_2R^d$, —N$R^cS$(=O)$_2NR^cR^d$, —O$R^d$, —S$R^d$, —OC(=O)$R^d$, —OC(=O)N$R^cR^d$, —O(=O)O$R^d$, S(=O)$_2R^d$, —S(=O)$R^d$, —OS(=O)$R^d$, —OS(=O)$_2R^d$, —OS(=O)$_2OR^d$, —S(=O)N$R^cR^d$, OS(=O)$_2NR^cR^d$, S(=O)$_2NR^cR^d$; where said $C_{3-6}$ cycloalkyl, $C_{1-6}$ alkyl, 3-10 membered heterocycloalkyl, phenyl, benzyl, alkylheteroaryl, and O—$C_{1-6}$ alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^cR^d$, $C_{1-6}$ alkyl, O—$C_{1-6}$ alkyl, and phenyl;

$R^2$ is selected from —C(=O)N$R^cR^d$, —N$R^cC$(=O)$R^d$, —N$R^cC$(=O)O$R^d$, —N$R^cC$(=O)N$R^cR^d$, —N$R^cS$(=O)$_2R^d$, —N$R^cS$(=O)$_2NR^cR^d$, $C_{1-10}$ alkyl optionally substituted by one or more $R^n$, $C_{2-6}$ alkenyl optionally substituted by one or more $R^n$, $C_{2-6}$ alkynyl optionally substituted by one or more $R^n$, or a group of Formula III

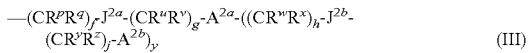

wherein $R^n$ is independently selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 3-11 membered heterocycloalkyl, —C(=O)$R^d$, —C(=O)O$R^d$, —C(=O)N$R^cR^d$, —C(O)C(=O)$R^d$, —N$R^cR^d$, —N$R^cC$(=O)$R^d$, —N$R^cC$(=O)O$R^d$, —N$R^cC$(=O)N$R^cR^d$, —N$R^cS$(=O)$_2R^d$, —N$R^cS$(=O)$_2NR^cR^d$, —O$R^d$, —S$R^d$, —OC(=O)$R^d$, —OC(=O)N$R^cR^d$, O(=O)O$R^d$, —S(=O)$_2R^d$, —S(=O) $R^d$, —OS(=O)$R^d$, OS(=O)$_2R^d$, —OS(=O)$_2OR^d$, —S(=O)N$R^cR^d$, —OS($_2NR^cR^d$ and —S(=O)$_2NR^cR^d$; where said $C_{3-6}$ cycloalkyl, $C_{1-6}$ alkyl, 3-11 membered heterocycloalkyl, $C_{1-6}$ alkyl and O—$C_{1-6}$ alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^cR^d$, $C_{1-6}$ alkyl, and O—$C_{1-6}$ alkyl; and $R^p$, $R^q$, $R^u$ and $R^v$ are independently selected from hydrogen, $C_{1-6}$ alkyl, C(O)N$R^cR^d$, $C_{3-7}$ cycloalkyl optionally substituted by one or more $R^b$, ($C_{1-6}$ alkyl)phenyl optionally substituted by one or more $R^b$, phenyl optionally substituted by one or more $R^b$, ($C_{1-6}$ alkyl)$C_{3-7}$ cycloalkyl optionally substituted by one or more $R^b$, 3-7 membered heterocycloalkyl optionally substituted by one or more $R^b$, 3-7 membered ($C_{1-6}$ alkyl)heterocycloalkyl optionally substituted by one or more $R^b$, 5-6 membered heteroaryl optionally substituted by one or more $R^b$, and 5-6 membered ($C_{1-6}$ alkyl)heteroaryl optionally substituted by one or more $R^b$;

$R^w$, $R^x$, $R^y$, $R^z$ are independently selected from hydrogen and $C_{1-6}$ alkyl;

$f$, $g$, $h$, and $j$ are independently selected from 0, 1, 2, 3 and 4; and y is selected from 0 and 1;

$J^{2a}$ is selected from a direct bond, O, S, C(O), $CH_2$, C(O)N$R^{s1}$, $NR^{s1}$C(O), $NR^{s1}$C(O)$NR^{s1}$ and $NR^{s1}$; where $R^{s1}$ is selected from hydrogen, $C_{1-6}$ alkyl, $C_{3-7}$ cycloalkyl optionally substituted by one or more $R^b$, ($C_{1-6}$ alkyl)phenyl optionally substituted by one or more $R^b$, phenyl optionally substituted by one or more $R^b$, ($C_{1-6}$ alkyl)$C_{3-7}$ cycloalkyl optionally substituted by one or more $R^b$, 3-7 membered heterocycloalkyl optionally substituted by one or more $R^b$, 3-7 membered ($C_{1-6}$ alkyl)heterocycloalkyl optionally substituted by one or more $R^b$, 5-6 membered heteroaryl optionally substituted by one or more $R^b$, and 5-6 membered ($C_{1-6}$ alkyl)heteroaryl optionally substituted by one or more $R^b$;

$J^{2b}$ is selected from a direct bond, O, S, C(O), $CH_2$, C(O)N$R^{s2}$, $NR^{s2}$C(O) and $NR^{s2}$; where $R^{s2}$ is selected from hydrogen, $C_{1-6}$ alkyl, $C_{3-7}$ cycloalkyl optionally substituted by one or more $R^b$, ($C_{1-6}$ alkyl)phenyl optionally substituted by one or more $R^b$, phenyl optionally substituted by one or more $R^b$, ($C_{1-6}$ alkyl)$C_{3-7}$ cycloalkyl optionally substituted by one or more $R^b$, 3-7 membered heterocycloalkyl optionally substituted by one or more $R^b$, 3-7 membered ($C_{1-6}$ alkyl) heterocycloalkyl optionally substituted by one or more $R^b$, 5-6 membered heteroaryl optionally substituted by one or more $R^b$, and 5-6 membered ($C_{1-6}$ alkyl)heteroaryl optionally substituted by one or more $R^b$;

each $R^b$ is independently selected from hydroxyl, =O, halogen, $C_{1-6}$ alkyl, CN, $C_{1-6}$ haloalkyl, $C_{1-6}$ haloalkoxy, $C_{3-6}$ cycloalkyl, O$R^d$, 3-10 membered heterocycloalkyl, wherein said $C_{1-6}$ alkyl, $C_{3-6}$ cycloalkyl and 3-10 membered heterocycloalkyl are optionally substituted with one or more groups selected from hydroxyl, halogen, CN, N$R^cR^d$, $C_{1-6}$ haloalkyl, $C_{3-6}$ cycloalkyl, $C_{1-6}$ alkyl, phenyl and O—$C_{1-6}$ alkyl;

$A^{2a}$ is selected from $C_{3-11}$ cycloalkyl optionally substituted by one or more $R^t$, 3-15 membered heterocycloalkyl optionally substituted by one or more $R^t$, $C_{6-11}$ aryl optionally substituted by one or more $R^t$, 5-15 membered heteroaryl optionally substituted by one or more $R^t$, $A^{2b}$ is selected from $C_{3-11}$ cycloalkyl optionally substituted by one or more $R^t$, 3-15 membered heterocycloalkyl optionally substituted by one or more $R^t$, $C_{6-11}$ aryl optionally substituted by one or more $R^t$, 5-15 membered heteroaryl optionally substituted by one or more $R^t$; and $R^t$ is selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 5-6 membered heteroaryl, 3-7 membered heterocycloalkyl, —C(=O)$R^d$, —(=O)$R^d$, —C(=O)N$R^cR^d$, —C(O)C(=O)$R^d$, —N$R^cR^d$, —N$R^cC$(=O)$R^d$, —N$R^cC$(=O)O$R^d$, —N$R^cC$(=O)N$R^cR^d$, —N$R^cS$(=O)$_2R^d$, —N$R^cS$(=O)$_2NR^cR^d$, —O$R^d$, —S$R^d$, —OC(=O)$R^d$, —OC(=O)NR$^c$R$^d$, —OC(=O)OR$^d$, —S(=O)$_2$R$^d$, —S(=O)R$^d$, —S(=O)R$^d$, OS(O)$_2$R$^d$, —OS(=O)$_2$OR$^d$, —S(=O)NR$^c$R$^d$, —OS(=O)$_2$NR$^c$R$^d$, —S(=O)$_2$NR$^c$R$^d$; where said C$_{3-6}$ cycloalkyl, C$_{1-6}$ alkyl, 5-6 membered heteroaryl, 3-7 membered heterocycloalkyl, C$_{1-6}$ alkyl and O—C$_{1-6}$alkyl are optionally substituted with one or more groups selected from hydroxyl, halogen, =O, CN, C$_{1-6}$ haloalkyl, C$_{1-6}$ haloalkoxy, C$_{3-6}$ cycloalkyl, C(O)NR$^c$R$^d$, NR$^c$R$^d$, C$_{1-6}$ alkyl, and O—C$_{1-6}$ alkyl; and wherein, each R$^c$ is independently selected from hydrogen, hydroxyl, halogen, CN, C$_{1-6}$ haloalkyl, C$_{3-6}$ cycloalkyl, C$_{1-6}$ alkyl and O—C$_{1-6}$ alkyl;

each R$^d$ is independently selected from hydrogen, hydroxyl, halogen, CN, C$_{1-6}$ haloalkyl, 3-7 membered heterocycloalkyl, C$_{3-6}$ cycloalkyl, C$_{1-6}$ alkyl, O—C$_{1-6}$ alkyl, C(=O)O(C$_{1-6}$alkyl), 5-6 membered heteroaryl and phenyl, wherein said C$_{1-6}$ alkyl, O—C$_{1-6}$ alkyl, phenyl, 3-7 membered heterocycloalkyl, 5-6 membered heteroaryl and C$_{3-6}$ cycloalkyl are optionally substituted with one or more groups selected from hydroxyl, =O, halogen, CN, NH$_2$, NHMe, NMe$_2$, C$_{1-6}$ haloalkyl, C$_{3-6}$ cycloalkyl, C$_{6-11}$ aryl, C$_{1-6}$ alkyl and O—C$_{1-6}$ alkyl; or R$^c$ and R$^d$, when attached to the same atom, together with the atom to which they are attached form a 3-10 membered ring, optionally containing one or more for heteroatoms selected from O, N and S, and wherein said ring is optionally substituted with one or more R$^m$; and R$^m$ is selected from hydrogen, hydroxyl, =O, halogen, C$_{1-6}$ alkyl, CN, C$_{1-6}$ haloalkyl, C$_{1-6}$ haloalkoxy, C$_{3-6}$ cycloalkyl, OR$^d$, 3-10 membered heterocycloalkyl, 5-6 membered (C$_{1-6}$ alkyl)heterocycloalkyl 5-6 membered (C$_{1-6}$ alkyl)heteroaryl wherein said C$_{1-6}$ alkyl, C$_{3-6}$ cycloalkyl, 3-10 membered heterocycloalkyl, 5-6 membered (C$_{1-6}$ alkyl)heterocycloalkyl, and 5-6 membered (C$_{1-6}$ alkyl)heteroaryl are optionally substituted with one or more groups selected from hydroxyl, halogen, CN, NH$_2$, NHMe, NMe$_2$, C$_{1-6}$ haloalkyl, C$_{3-6}$ cycloalkyl, C$_{1-6}$ alkyl, phenyl, and O—C$_{1-6}$alkyl.

3. A compound according to paragraph 2, or a salt or solvate thereof, wherein X is selected from NR$^3$ and 0.

4. A compound according to paragraph 2, or a salt or solvate thereof, wherein X is selected from CR$^4$ and 0.

5. A compound according to any one of paragraphs 2 to 4, or a salt or solvate thereof, wherein X is O.

6. A compound according to any one of paragraphs 2 to 5, or a salt or solvate thereof, wherein R$^3$ and R$^4$ are independently selected from hydrogen and C$_{1-3}$ alkyl; suitably hydrogen and methyl; suitably hydrogen.

7. A compound according to any one of paragraphs 2 to 6, or a salt or solvate thereof, wherein R$^5$ is selected from hydrogen, C$_{1-3}$ alkyl and halogen, suitably hydrogen.

8. A compound according to any one of the paragraphs 2 to 7, or a salt or solvate thereof, wherein n is selected from 0, 1 and 2, suitably 0 and 1, more suitably 0.

9. A compound according to any one of the preceding paragraphs, or a salt or solvate thereof, wherein R$^e$, R$^f$, R$^g$, and R$^h$ are hydrogen.

10. A compound according to any one of the preceding paragraphs, or a salt or solvate thereof, wherein a is selected from 0 and 1 and $_b$ is selected from 0 and 1.

11. A compound according to any one of the paragraphs 1 to 9, or a salt or solvate thereof, wherein $_a$ is 1 or 2 and $_b$ is 0, suitably $_a$ is 1 and $_b$ is 0.

12. A compound according to any one of the preceding paragraphs, or a salt or solvate thereof, wherein J$^1$ is selected from O and NR$^s$; where R$^s$ is selected from hydrogen and C$_{1-3}$ alkyl, suitably hydrogen.

13. A compound according to any one of the preceding paragraphs, or a salt or solvate thereof, wherein J$^1$ is O.

14. A compound according to any one of paragraphs 1 and 2, or a salt or solvate thereof, wherein said compound is of sub-Formula (Ib):

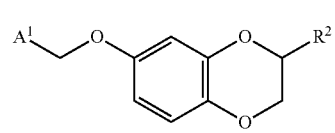

(Ib)

where A$^1$ and R$^2$ are as defined in claim 1.

15. A compound according to any one of the preceding paragraphs, or a salt or solvate thereof, wherein A$^1$ is selected from C$_{6-11}$ aryl optionally substituted by one or more R$^k$, 3-15 membered heterocycloalkyl optionally substituted by one or more R$^k$, and 5-15 membered heteroaryl optionally substituted by one or more R$^k$.

16. A compound according to any one of the preceding paragraphs, or a salt or solvate thereof, wherein A$^1$ is selected from C$_{6-11}$ aryl optionally substituted by one or more R$^k$ and 5-15 membered heteroaryl optionally substituted by one or more R$^k$.

17. A compound according to any one of the preceding paragraphs, or a salt or solvate thereof, wherein A$^1$ is selected from phenyl optionally substituted by one or more R$^k$ and 5-6 membered heteroaryl optionally substituted by one or more R$^k$.

18. A compound according to any one of the preceding paragraphs, or a salt or solvate thereof, wherein A$^1$ is selected from phenyl optionally substituted by one or more R$^k$ and 6 membered heteroaryl optionally substituted by one or more R$^k$.

19. A compound according to any one of the preceding paragraphs, or a salt or solvate thereof, wherein A$^1$ is selected from phenyl optionally substituted by one or more R$^k$ and pyridyl optionally substituted by one or more R$^k$.

20. A compound according to any one of the preceding paragraphs, or a salt or solvate thereof, wherein A$^1$ is phenyl optionally substituted by one or more R$^k$.

21. A compound according to any one of the preceding paragraphs, or a salt or solvate thereof, wherein R$^k$ is selected from hydrogen, hydroxyl, =O, halogen, CN, C$_{1-6}$haloalkyl, C$_{1-6}$ haloalkoxy, C$_{1-6}$ alkyl, and O—C$_{1-6}$ alkyl; where said C$_{1-6}$ alkyl and O—C$_{1-6}$alkyl are optionally substituted with one or more groups selected from hydroxyl, halogen, =O, CN, C$_{1-6}$ haloalkyl, C$_{1-6}$ haloalkoxy, C$_{3-6}$ cycloalkyl, NR$^c$R$^d$, C$_{1-6}$alkyl, O—C$_{1-6}$alkyl, and phenyl.

22. A compound according to any one of the preceding paragraphs, or a salt or solvate thereof, wherein R$^k$ is selected from halogen, CN, C$_{1-6}$ haloalkyl, C$_{1-6}$ haloalkoxy, C$_{1-6}$ alkyl, and O—C$_{1-6}$ alkyl.

23. A compound according to any one of the preceding paragraphs, or a salt or solvate thereof, wherein R$^k$ is selected from halogen, C$_{1-6}$ alkyl, and O—C$_{1-6}$ alkyl.

24. A compound according to any one of the preceding paragraphs, or a salt or solvate thereof, wherein R$^k$ is selected from halogen, C$_{1-3}$ alkyl, and O—C$_{1-3}$ alkyl.

25. A compound according to any one of the preceding paragraphs, or a salt or solvate thereof, wherein R$^1$ is selected from:

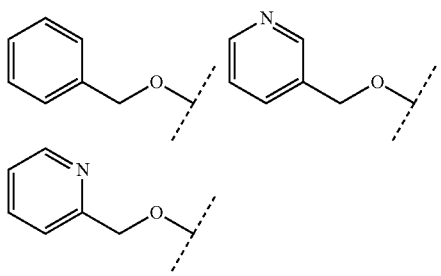

where the phenyl and pyridyl rings are optionally substituted with one or more groups selected from C$_{1-3}$ alkyl and halogen.

26. A compound according to paragraph 25, or a salt or solvate thereof, wherein R$^1$ is selected from:

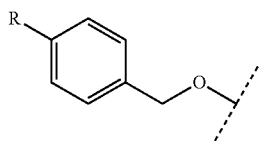

where R is selected from hydrogen, methyl, fluoro and chloro.

27. A compound according to paragraph 26, or a salt or solvate thereof, wherein R$^1$ is:

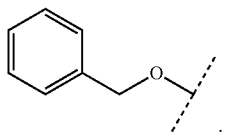

28. A compound according to any one of the preceding paragraphs, or a salt or solvate thereof, wherein R$^2$ is selected from —C(═O)NR$^c$R$^d$, —NR$^c$C(═O)R$^d$, C$_{1-10}$alkyl optionally substituted by one or more R$^n$, and a group of Formula III 29. A compound according to any one of the preceding paragraphs, or a salt or solvate thereof, wherein R$^2$ is selected from —C(═O)NR$^c$R$^d$, C$_{1-10}$alkyl optionally substituted by one or more R$^n$, and a group of Formula III.

30. A compound according to any one of the preceding paragraphs, or a salt or solvate thereof, wherein R$^2$ is selected from C$_{1-10}$alkyl optionally substituted by one or more R, and a group of Formula III.

31. A compound according to any one of paragraphs 1 to 29, or a salt or solvate thereof, wherein R$^2$ is selected —C(═O) NR$^c$R$^d$, and a group of Formula III.

32. A compound according to any one of the preceding paragraphs, or a salt or solvate thereof, wherein R$^n$ is selected from hydroxyl, ═O, halogen, CN, C$_{1-6}$ haloalkyl, C$_{1-6}$ haloalkoxy, C$_{1-6}$ alkyl, O—C$_{1-6}$ alkyl, C$_{3-6}$ cycloalkyl, 3-11 membered heterocycloalkyl, —C(═O)R$^d$, —C(═O) OR$^d$, —C(═O)NR$^c$R$^d$, —C(O)C(═O)R$^d$, —NR$^c$R$^d$, —NR$^c$C(═O)R$^d$, —NR$^c$C(═O)OR$^d$, —OR$^d$, —OC(═O) R$^d$, —OC(═O)NR$^c$R$^d$, and —OC(═O)OR$^d$; where said C$_{3-6}$ cycloalkyl, C$_{1-6}$ alkyl, 3-11 membered heterocycloalkyl, C$_{1-6}$ alkyl and O—C$_{3-6}$ alkyl are optionally substituted with one or more groups selected from hydroxyl, halogen, ═O, CN, C$_{1-6}$ haloalkyl, C$_{1-6}$ haloalkoxy, C$_{3-6}$ cycloalkyl, NR$^c$R$^d$, C$_{1-6}$ alkyl, and O—C$_6$ alkyl.

33. A compound according to any one of the preceding paragraphs, or a salt or solvate thereof, wherein R$^n$ is selected from 3-11 membered heterocycloalkyl, —C(═O) NR$^c$R$^d$, —NR$^c$R$^d$, —NR$^c$C(═O)R$^d$; where said 3-11 membered heterocycloalkyl is optionally substituted with one or more groups selected from hydroxyl, halogen, ═O, CN, C$_{1-6}$ haloalkyl, C$_{1-6}$ haloalkoxy, C$_{3-6}$ cycloalkyl, NR$^c$R$^d$, C$_{1-6}$alkyl, and O—C$_{1-6}$ alkyl.

34. A compound according to any one of the preceding paragraphs, or a salt or solvate thereof, wherein R$^n$ is selected from 3-11 membered heterocycloalkyl, —NR$^c$R$^d$, —NR$^c$C(═O)R$^d$; where said 3-11 membered heterocycloalkyl is optionally substituted with one or more groups selected from hydroxyl, halogen, ═O, CN, C$_{1-6}$haloalkyl, C$_{1-6}$haloalkoxy, C$_{3-6}$cycloalkyl, NR$^c$R$^d$, C$_{1-6}$ alkyl, and O—C$_{1-6}$ alkyl.

35. A compound according to any one of the preceding paragraphs, or a salt or solvate thereof, wherein R$^2$ is selected is a group of Formula III.

36. A compound according to any one of the preceding paragraphs, or a salt or solvate thereof, wherein $f$ is selected from 0 and 1 and g is selected from 0 and 1.

37. A compound according to any one of the preceding paragraphs, or a salt or solvate thereof, wherein $f$ is 1, and $g$ is 0, or $f$ is 0 and $g$ is 1, or $f$ is 1, and $g$ is 1.

38. A compound according to any one of the preceding paragraphs, or a salt or solvate thereof, wherein $f$ is 1, and $g$ is 0, or $f$ is 0 and $g$ is 1.

39. A compound according to any one of the preceding paragraphs, or a salt or solvate thereof, wherein J$^{2a}$ is selected from C(O), CH$_2$, C(O)NR$^{s1}$, NR$^{s1}$C(O), NR$^{s1}$C(O) NR$^{s1}$ and NR$^{s1}$.

40. A compound according to any one of the preceding paragraphs, or a salt or solvate thereof, wherein J$^{2a}$ is selected from C(O)NR$^{s1}$, NR$^{s1}$C(O) and NR$^{s1}$.

41. A compound according to any one of the preceding paragraphs, or a salt or solvate thereof, wherein R$^{s1}$ is selected from hydrogen, C$_{1-6}$ alkyl, (C$_{1-6}$alkyl)phenyl optionally substituted by one or more R$^b$, 3-7 membered heterocycloalkyl optionally substituted by one or more R$^b$, and 3-7 membered (C$_{1-6}$alkyl)heterocycloalkyl optionally substituted by one or more R$^b$.

42. A compound according to any one of the preceding paragraphs, or a salt or solvate thereof, wherein R$^b$ is selected from ═O, C$_{1-6}$ alkyl and OR$^d$, wherein said C$_{1-6}$ alkyl is optionally substituted with one or more groups selected from hydroxyl, halogen, CN, NR$^c$R$^d$, C$_{1-6}$ haloalkyl, C$_{3-6}$ cycloalkyl, C$_{1-6}$ alkyl, phenyl and O—C$_{1-6}$ alkyl.

43. A compound according to any one of the preceding paragraphs, or a salt or solvate thereof, wherein R$^{s1}$ is independently selected from hydrogen, methyl and ethyl.

44. A compound according to any one of the preceding paragraphs, or a salt or solvate thereof, wherein R$^{s1}$ is hydrogen.

45. A compound according to any one of the preceding paragraphs, or a salt or solvate thereof, wherein R$^p$, R$^q$, R$^u$, R$^v$, R$^w$, R$^x$, R$^y$, R$^z$ are independently selected from methyl, ethyl and hydrogen.

46. A compound according to any one of the preceding paragraphs, or a salt or solvate thereof, wherein R$^p$, R$^q$, R$^u$, R$^v$, R$^w$, R$^x$, R$^y$, R$^z$ are hydrogen.

47. A compound according to any one of paragraphs 1 and 2, or a salt or solvate thereof, wherein the compound is of sub-formula Ic:

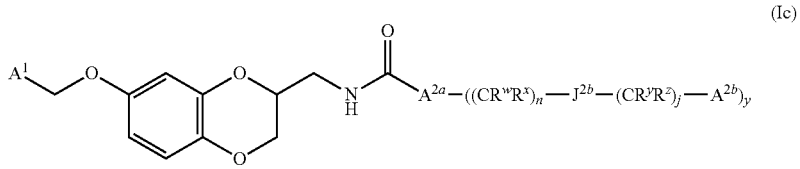

(Ic)

where $A^1$, $A^{2a}$, $R^w$, $R^x$, $J^{2b}$, $R^y$, $R^z$, $A^{2b}$, $h$, $j$ and $y$ are as defined in claim 1.

48. A compound according to any one of the preceding paragraphs, or a salt or solvate thereof, wherein $A^{2a}$ is selected from $C_{3-11}$ cycloalkyl optionally substituted by one or more $R^t$, 3-15 membered heterocycloalkyl optionally substituted by one or more $R^t$, $C_{6-11}$ aryl optionally substituted by one or more $R^t$, and 5-15 membered heteroaryl optionally substituted by one or more $R^t$.

49. A compound according to any one of the preceding paragraphs, or a salt or solvate thereof, wherein $A^{2a}$ is selected from phenyl optionally substituted by one or more $R^t$, 5-6 membered cycloalkyl optionally substituted by one or more $R^t$, 5-6 membered heterocycloalkyl optionally substituted by one or more $R^t$, and a 5-6 membered heteroaryl optionally substituted by one or more $R^t$.

50. A compound according to any one of the preceding paragraphs, or a salt or solvate thereof, wherein $A^{2a}$ is selected from phenyl optionally substituted by one or more $R^t$, 5-6 membered heterocycloalkyl optionally substituted by one or more $R^t$, and a 5-6 membered heteroaryl optionally substituted by one or more $R^t$.

51. A compound according to any one of the preceding paragraphs, or a salt or solvate thereof, wherein $A^{2a}$ is selected from phenyl optionally substituted by one or more $R^t$, tetrahydropyran optionally substituted by one or more $R^t$, piperazine optionally substituted by one or more $R^t$, piperidine optionally substituted by one or more $R^t$, pyridyl optionally substituted by one or more $R^t$, furan optionally substituted by one or more $R^t$, and oxazole optionally substituted by one or more $R^t$.

52. A compound according to any one of the preceding paragraphs, or a salt or solvate thereof, wherein $A^{2a}$ is selected from phenyl optionally substituted by one or more $R^t$, tetrahydropyran optionally substituted by one or more $R^t$, piperazine optionally substituted by one or more $R^t$, piperidine optionally substituted by one or more $R^t$, furan optionally substituted by one or more $R^t$, and oxazole optionally substituted by one or more $R^t$.

53. A compound according to any one of the preceding paragraphs, or a salt or solvate thereof, wherein y is 0.

54. A compound according to any one of the preceding paragraphs, or a salt or solvate thereof, wherein y is 1.

55. A compound according to any one of the preceding paragraphs, or a salt or solvate thereof, wherein $h$ is selected from 0 and 1 and $j$ is selected from 0 and 1.

56. A compound according to any one of the preceding paragraphs, or a salt or solvate thereof, wherein $h$ is 1, and $j$ is 0, or is 0, and is 0.

57. A compound according to any one of the preceding paragraphs, or a salt or solvate thereof, wherein $J^{2b}$ is a direct bond, $CH_2$ or $C(O)$.

58. A compound according to any one of the preceding paragraphs, or a salt or solvate thereof, wherein $J^{2b}$ is a direct bond or $CH_2$.

59. A compound according to any one of the preceding paragraphs, or a salt or solvate thereof, wherein $A^{2b}$ is selected from phenyl optionally substituted by one or more $R^t$, 5-6 membered heterocycloalkyl optionally substituted by one or more $R^t$, and a 5-6 membered heteroaryl optionally substituted by one or more $R^t$.

60. A compound according to any one of the preceding paragraphs, or a salt or solvate thereof, wherein $A^{2b}$ is selected from piperazinyl optionally substituted by one or more $R^t$, piperidinyl optionally substituted by one or more $R^t$, morpholinyl optionally substituted by one or more $R^t$, tetrahydropyranyl optionally substituted by one or more $R^t$ and furanyl optionally substituted by one or more $R^t$.

61. A compound according to any one of the preceding paragraphs, or a salt or solvate thereof, wherein $R^t$ is selected from hydroxyl, =O, halogen, $C_{1-6}$ alkyl, O—$C_{1-6}$ alkyl, $C_{3-6}$ cycloalkyl, 5-6 membered heteroaryl, 3-7 membered heterocycloalkyl, —C(=O)$R^d$, —C(=O)O$R^d$, —C(=O)N$R^cR^d$, —N$R^cR^d$, —N$R^cC$(=O)$R^d$, —N$R^cC$(=O)O$R^d$, and —N$R^cC$(=O)N$R^cR^d$; where said $C_{3-6}$ cycloalkyl, $C_{1-6}$ alkyl, 5-6 membered heteroaryl, 3-7 membered heterocycloalkyl, $C_{1-6}$ alkyl and O—$C_{1-6}$alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, C(O)N$R^cR^d$, N$R^cR^d$, $C_{1-6}$ alkyl, and O—$C_{1-6}$ alkyl.

62. A compound according to any one of the preceding paragraphs, or a salt or solvate thereof, wherein $R^t$ is selected from hydroxyl, =O, halogen, $C_{1-6}$ alkyl, 5-6 membered heteroaryl, 3-7 membered heterocycloalkyl, —C(=O)$R^d$, —C(=O)O$R^d$, —N$R^cR^d$, and —N$R^cC$(=O)$R^d$; where said $C_{1-6}$alkyl, 5-6 membered heteroaryl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$ cycloalkyl, C(O)N$R^cR^d$, N$R^cR^d$, $C_{1-6}$ alkyl, and O—$C_{1-6}$ alkyl.

63. A compound according to any one of the preceding paragraphs, or a salt or solvate thereof, wherein $R^t$ is selected from $C_{1-6}$ alkyl, 5-6 membered heteroaryl, 3-7 membered heterocycloalkyl, —C(=O)$R^d$, —C(=O)O$R^d$, —N$R^cR^d$, and —N$R^cC$(=O)$R^d$; where said $C_{1-6}$ alkyl, 5-6 membered heteroaryl, and 3-7 membered heterocycloalkyl are optionally substituted with one or more groups selected from hydroxyl, halogen, =O, CN, $C_{1-6}$ haloalkyl, $C_{1-6}$ haloalkoxy, $C_{3-6}$cycloalkyl, C(O)N$R^cR^d$, N$R^cR^d$, $C_{1-6}$alkyl, and O—$C_{1-6}$ alkyl.

64. A compound according to any one of the preceding paragraphs, or a salt or solvate thereof, wherein $R^t$ is selected from $C_{1-6}$ alkyl, —C(=O)$R^d$, —C(=O)O$R^d$, —N$R^cR^d$, and —N$R^cC$(=O)$R^d$; where said $C_{1-6}$alkyl is optionally substituted with one or more groups selected from hydroxyl, halogen, =O, CN, $C_{1-6}$ haloalkyl, $C_{1-6}$ haloalkoxy, $C_{3-6}$ cycloalkyl, C(O)N$R^cR^d$, N$R^cR^d$, $C_{1-6}$ alkyl, and O—$C_{1-6}$ alkyl.

65. A compound according to any one of the preceding paragraphs, or a salt or solvate thereof, wherein $R^t$ is selected from $C_{1-6}$ alkyl, —C(=O)O$R^d$, —N$R^cR^d$, and —N$R^cC$(=O)$R^d$; where said $C_{1-6}$ alkyl is optionally substituted with one or more groups selected from hydroxyl, halogen, =O, CN, $C_{1-6}$ haloalkyl, $C_{1-6}$ haloalkoxy, $C_{3-6}$ cycloalkyl, C(O)NR$^c$R$^d$, NR$^c$R$^d$, $C_{1-6}$ alkyl, and O—$C_{1-6}$ alkyl.

66. A compound according to any one of the preceding paragraphs, or a salt or solvate thereof, wherein R$^t$ is selected from $C_{1-6}$ alkyl, —NR$^c$R$^d$, and —NR$^c$C(=O)R$^d$; where said $C_{1-6}$ alkyl is optionally substituted with one or more groups selected from hydroxyl, halogen, =O, CN, $C_{1-6}$ haloalkyl, $C_{1-6}$ haloalkoxy, $C_{3-6}$ cycloalkyl, C(O)NR$^c$R$^d$, NR$^c$R$^d$, $C_{1-6}$ alkyl, and O—$C_{1-6}$ alkyl.

67. A compound according to any one of the preceding paragraphs, or a salt or solvate thereof, wherein R$^t$ is selected from $C_{1-3}$ alkyl optionally substituted with one or more groups selected from hydroxyl, halogen, =O, CN, $C_{1-6}$ haloalkyl, $C_{1-6}$ haloalkoxy, $C_{3-6}$ cycloalkyl, C(O)NR$^c$R$^d$, NR$^c$R$^d$, $C_{1-6}$ alkyl, and O—$C_{1-6}$ alkyl.

68. A compound according to any one of the preceding paragraphs, or a salt or solvate thereof, wherein R$^c$ is independently selected from hydrogen and $C_{1-6}$ alkyl, suitably hydrogen and $C_{1-3}$ alkyl.

69. A compound according to any one of the preceding paragraphs, or a salt or solvate thereof, wherein R$^d$ is selected from hydrogen, $C_{3-6}$ cycloalkyl, $C_{1-6}$ alkyl, O—$C_{1-6}$ alkyl, C(=O)O($C_{1-6}$ alkyl), 5-6 membered heteroaryl and phenyl, wherein said $C_{1-6}$ alkyl, O—$C_{1-6}$ alkyl, phenyl, 5-6 membered heteroaryl and $C_{3-6}$ cycloalkyl are optionally substituted with one or more groups selected from hydroxyl, =O, halogen, CN, $NH_2$, NHMe, $NMe_2$, $C_{1-6}$ haloalkyl, $C_{3-6}$ cycloalkyl, $C_{6-11}$ aryl, $C_{1-6}$ alkyl and O—$C_{1-6}$ alkyl.

70. A compound according to any one of the preceding paragraphs, or a salt or solvate thereof, wherein R$^d$ is selected from hydrogen, $C_{3-6}$ cycloalkyl, $C_{1-6}$ alkyl, C(=O)O($C_{1-6}$ alkyl), and 5-6 membered heteroaryl, wherein said $C_{1-6}$ alkyl, 5-6 membered heteroaryl and $C_{3-6}$ cycloalkyl are optionally substituted with one or more groups selected from hydroxyl, =O, halogen, CN, $NH_2$, NHMe, $NMe_2$, $C_{1-6}$ haloalkyl, $C_{3-6}$ cycloalkyl, $C_{6-11}$ aryl, $C_{1-6}$ alkyl and O—$C_{1-6}$ alkyl.

71. A compound according to any one of paragraphs 1 to 67, or a salt or solvate thereof, wherein R$^c$ and R$^d$, when attached to the same atom, together with the atom to which they are attached form a 5-6 membered ring, optionally containing one or more for heteroatoms selected from O, NH and S, and wherein said ring is optionally substituted with one or more R$^m$.

72. A compound according to any one of the preceding paragraphs, or a salt or solvate thereof, wherein R$^m$ is selected from $C_{1-6}$ alkyl, 5-6 membered ($C_{1-6}$ alkyl)heterocycloalkyl and 5-6 membered ($C_{1-6}$ alkyl)heteroaryl wherein said $C_{1-6}$ alkyl, 5-6 membered ($C_{1-6}$ alkyl)heterocycloalkyl, and 5-6 membered ($C_{1-6}$ alkyl)heteroaryl are optionally substituted with one or more groups selected from hydroxyl, halogen, CN, $NH_2$, NHMe, $NMe_2$, $C_{1-6}$ haloalkyl, $C_{3-6}$ cycloalkyl, $C_{1-6}$ alkyl, phenyl, and O—$C_{1-6}$ alkyl.

73. A compound according to any one of the preceding paragraphs, or a salt or solvate thereof, wherein R$^2$ is selected from

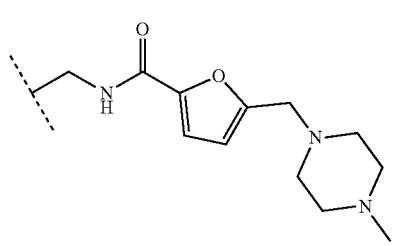

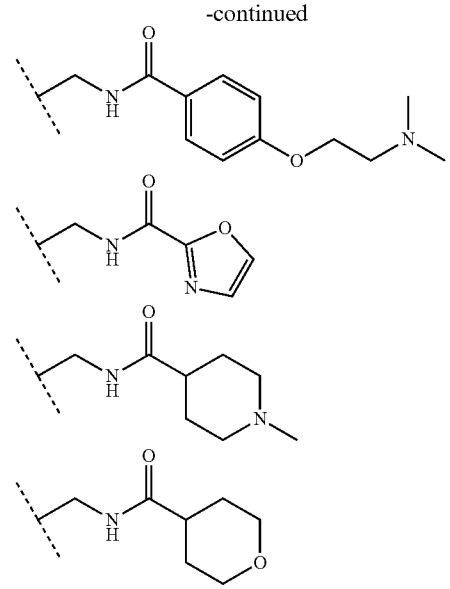

74. A compound according to any one of the preceding paragraphs, or a salt or solvate thereof, wherein R$^2$ is selected from

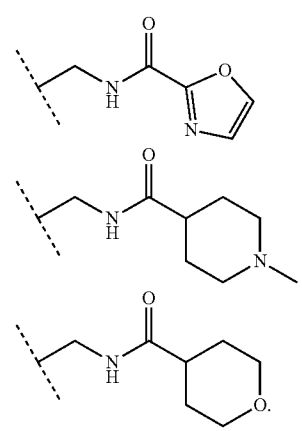

75. A compound according to any one of the preceding paragraphs, or a salt or solvate thereof, wherein R$^2$ is selected from

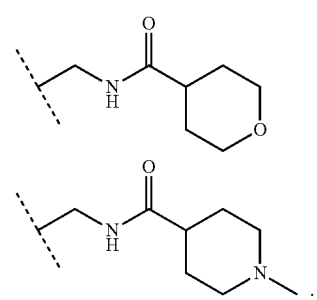

76. A compound according to any one of the paragraphs 47 to 75, or a salt or solvate thereof, wherein A$^1$ is selected from $C_{6-11}$ aryl optionally substituted by one or more R, 3-15

77. A compound according to any one of paragraphs 47 to 76, or a salt or solvate thereof, wherein $A^1$ is selected from $C_{6-11}$ aryl optionally substituted by one or more $R^k$ and 5-15 membered heteroaryl optionally substituted by one or more $R^k$.

78. A compound according to any one of paragraphs 47 to 77, or a salt or solvate thereof, wherein $A^1$ is selected from phenyl optionally substituted by one or more $R^k$ and 5-6 membered heteroaryl optionally substituted by one or more $R^k$.

79. A compound according to any one of paragraphs 47 to 78, or a salt or solvate thereof, wherein $A^1$ is selected from phenyl optionally substituted by one or more $R^k$ and 6 membered heteroaryl optionally substituted by one or more $R^k$.

80. A compound according to any one of paragraphs 47 to 79, or a salt or solvate thereof, wherein $A^1$ is selected from phenyl optionally substituted by one or more $R^k$ and pyridyl optionally substituted by one or more $R^k$.

81. A compound according to any one of paragraphs 47 to 80, or a salt or solvate thereof, wherein $A^1$ is phenyl optionally substituted by one or more $R^k$.

82. A compound according to any one of paragraphs 47 to 81, or a salt or solvate thereof, wherein $R^k$ is selected from hydrogen, hydroxyl, =O, halogen, CN, $C_{1-6}$ haloalkyl, $C_{1-6}$ haloalkoxy, $C_{1-6}$ alkyl, and O—$C_{1-6}$ alkyl; where said $C_{1-6}$ alkyl and O—$C_{1-6}$alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^cR^d$, $C_{1-6}$alkyl, O—$C_{1-6}$alkyl, and phenyl.

83. A compound according to any one of paragraphs 47 to 82, or a salt or solvate thereof, wherein $R^k$ is selected from halogen, CN, $C_{1-6}$ haloalkyl, $C_{1-6}$ haloalkoxy, $C_{1-6}$ alkyl, and O—$C_{1-6}$ alkyl.

84. A compound according to any one of paragraphs 47 to 83, or a salt or solvate thereof, wherein $R^k$ is selected from halogen, $C_{1-6}$alkyl, and O—$C_{1-6}$ alkyl.

85. A compound according to any one of paragraphs 47 to 84, or a salt or solvate thereof, wherein $R^k$ is selected from halogen, $C_{1-3}$alkyl, and O—$C_{1-3}$ alkyl.

86. A compound according to any one of the preceding paragraphs, or a salt or solvate thereof, wherein the compound is the R-enantiomer, suitably wherein the compound is the R-enantiomer at the chiral centre bonded to group $R^2$.

87. A compound according to any one of the preceding paragraphs, or a salt or solvate thereof, wherein $R^{s2}$ is selected from hydrogen, methyl and ethyl, suitably $R^{s2}$ is hydrogen.

88. A compound, or a salt or solvate thereof, selected from:
5-(4-Methyl-piperazin-1-ylmethyl)-furan-2-carboxylic acid ((R)-7-benzyloxy-2,3-dihydro-benzo[1,4]dioxin-2-ylmethyl)-amide;
Oxazole-2-carboxylic acid ((R)-7-benzyloxy-2,3-dihydro-benzo[1,4]dioxin-2-ylmethyl)-amide;
Oxazole-2-carboxylic acid [(R)-7-(pyridin-3-ylmethoxy)-2,3-dihydro-benzo[1,4]dioxin-2-ylmethyl]-amide;
Oxazole-2-carboxylic acid [(R)-7-(1H-pyrazol-4-ylmethoxy)-2,3-dihydro-benzo[1,4]dioxin-2-ylmethyl]-amide;
Oxazole-2-carboxylic acid [(R)-7-(1-methyl-piperidin-4-ylmethoxy)-2,3-dihydro-benzo[1,4]dioxin-2-ylmethyl]-amide;
5-(4-Methyl-piperazin-1-ylmethyl)-furan-2-carboxylic acid [(R)-7-(4-methoxy-benzyloxy)-2,3-dihydro-benzo[1,4]dioxin-2-ylmethyl]-amide;
5-(4-Methyl-piperazin-1-ylmethyl)-furan-2-carboxylic acid ((R)-7-phenethyloxy-2,3-dihydro-benzo[1,4]dioxin-2-ylmethyl)-amide;
5-(4-Methyl-piperazin-1-ylmethyl)-furan-2-carboxylic acid [(R)-7-(4-chloro-benzyloxy)-2,3-dihydro-benzo[1,4]dioxin-2-ylmethyl]-amide;
5-(4-Methyl-piperazin-1-ylmethyl)-oxazole-2-carboxylic acid ((R)-7-benzyloxy-2,3-dihydro-benzo[1,4]dioxin-2-ylmethyl)-amide;
1-methyl-piperidine-4-carboxylic acid ((R)-7-benzyloxy-2,3-dihydro-benzo[1,4]dioxin-2-ylmethyl)-amide;
Tetrahydro-pyran-4-carboxylic acid ((R)-7-benzyloxy-2,3-dihydro-benzo[1,4]dioxin-2-ylmethyl)-amide;
N—((R)-7-Benzyloxy-2,3-dihydro-benzo[1,4]dioxin-2-ylmethyl)-3-dimethylamino-propionamide;
Oxazole-2-carboxylic acid ((R)-7-benzyloxy-2,3-dihydro-benzo[1,4]dioxin-2-ylmethyl)-[4-(3-dimethylamino-propoxy)-benzyl]-amide;
(4-{[((R)-7-Benzyloxy-2,3-dihydro-benzo[1,4]dioxin-2-ylmethyl)-(oxazole-2-carbonyl)-amino]-methyl}-benzyl)-carbamic acid tert-butyl ester;
Oxazole-2-carboxylic acid (4-aminomethyl-benzyl)-((R)-7-benzyloxy-2,3-dihydro-benzo[1,4]dioxin-2-ylmethyl)-amide;
Oxazole-2-carboxylic acid ((R)-7-benzyloxy-2,3-dihydro-benzo[1,4]dioxin-2-ylmethyl)-(1-benzyl-piperidin-4-ylmethyl)-amide;
((R)-7-Benzyloxy-2,3-dihydro-benzo[1,4]dioxin-2-ylmethyl)-(tetrahydro-pyran-4-ylmethyl)-amine;
Oxazole-2-carboxylic acid ((R)-7-benzyloxy-2,3-dihydro-benzo[1,4]dioxin-2-ylmethyl)-(1-benzyl-piperidin-4-yl)-amide;
5-(4-Methyl-piperazin-1-ylmethyl)-furan-2-carboxylic acid [(R)-7-(5-chloro-pyridin-3-ylmethoxy)-2,3-dihydro-benzo[1,4]dioxin-2-ylmethyl]-amide;
5-(4-Methyl-piperazin-1-ylmethyl)-furan-2-carboxylic acid ((R)-7-benzylamino-2,3-dihydro-benzo[1,4]dioxin-2-ylmethyl)-amide;
5-(4-Methyl-piperazin-1-ylmethyl)-furan-2-carboxylic acid [(R)-7-(5-chloro-pyridin-2-ylmethoxy)-2,3-dihydro-benzo[1,4]dioxin-2-ylmethyl]-amide;
1-{2-[((R)-7-Benzyloxy-2,3-dihydro-benzo[1,4]dioxin-2-ylmethyl)-amino]-2-phenyl-ethyl}-pyrrolidin-2-one;
((R)-7-Benzyloxy-2,3-dihydro-benzo[1,4]dioxin-2-ylmethyl)-indan-1-yl-amine;
C—((R)-7-Benzyloxy-2,3-dihydro-benzo[1,4]dioxin-2-yl)-methylamine;
2-[((R)-7-Benzyloxy-2,3-dihydro-benzo[1,4]dioxin-2-ylmethyl)-amino]-N-methyl-2-phenyl-acetamide;
2-[((R)-7-Benzyloxy-2,3-dihydro-benzo[1,4]dioxin-2-ylmethyl)-amino]-N-methyl-2-phenyl-acetamide;
7-Benzyloxy-2,3-dihydro-benzo[1,4]dioxine-2-carboxylic acid (1-methyl-piperidin-4-ylmethyl)-amide;
7-Benzyloxy-2,3-dihydro-benzo[1,4]dioxine-2-carboxylic acid (4-amino-cyclohexyl)-amide;
3-((R)-7-Benzyloxy-2,3-dihydro-benzo[1,4]dioxin-2-ylmethyl)-8-methyl-1,3,8-triaza-spiro[4.5]decane-2,4-dione;
7-Benzyloxy-2,3-dihydro-benzo[1,4]dioxine-2-carboxylic acid (1H-imidazol-2-yl)-amide;
3-((R)-7-Benzyloxy-2,3-dihydro-benzo[1,4]dioxin-2-ylmethyl)-1-pyridin-2-yl-imidazolidine-2,4-dione;
7-Benzyloxy-2,3-dihydro-benzo[1,4]dioxine-2-carboxylic acid [4-(2-amino-acetylamino)-cyclohexyl]-amide;

3-((R)-7-Benzyloxy-2,3-dihydro-benzo[1,4]dioxin-2-ylmethyl)-1-piperidin-4-yl-imidazolidine-2,4-dione;
((R)-7-Benzyloxy-2,3-dihydro-benzo[1,4]dioxin-2-ylmethyl)-(1-methyl-piperidin-4-ylmethyl)-amine;
7-Benzyloxy-2,3-dihydro-benzo[1,4]dioxine-2-carboxylic acid 3-(4-methyl-piperazin-1-ylmethyl)-benzylamide;
(7-Benzyloxy-2,3-dihydro-benzo[1,4]dioxin-2-yl)-(4-pyridin-4-ylmethyl-piperazin-1-yl)-methanone;
(7-Benzyloxy-2,3-dihydro-benzo[1,4]dioxin-2-yl)-[4-(tetrahydro-pyran-4-ylmethyl)-piperazin-1-yl]-methanone;
N-{4-[((R)-7-Benzyloxy-2,3-dihydro-benzo[1,4]dioxin-2-ylmethyl)-amino]-cyclohexyl}-2-dimethylamino-acetamide;
1-{2-[4-((R)-7-Benzyloxy-2,3-dihydro-benzo[1,4]dioxin-2-ylmethyl)-piperazin-1-yl]-ethyl}-1H-pyridin-2-one;
N-{4-[((R)-7-Benzyloxy-2,3-dihydro-benzo[1,4]dioxin-2-ylmethyl)-(2H-pyrazol-3-ylmethyl)-amino]-cyclohexyl}-2-dimethylamino-acetamide;
((R)-7-Benzyloxy-2,3-dihydro-benzo[1,4]dioxin-2-ylmethyl)-[3-(4-methyl-piperazin-1-yl)-benzyl]-amine;
1-(7-benzyloxy-2,3-dihydro-benzo[1,4]dioxin-2-ylmethyl)-3-(1-methyl-piperidin-4-yl)-urea;
4-methyl-piperazine-1-carboxylic acid ((R)-7-benzyloxy-2,3-dihydro-benzo[1,4]dioxin-2-ylmethyl)-amide;
3-(7-Benzyloxy-2,3-dihydro-benzo[1,4]dioxin-2-ylmethyl)-1-methyl-1-(1-methyl-piperidin-4-yl)-urea;
N—((R)-7-Benzyloxy-2,3-dihydro-benzo[1,4]dioxin-2-ylmethyl)-3-(4-methyl-piperazin-1-ylmethyl)-benzamide;
N—((R)-7-Benzyloxy-2,3-dihydro-benzo[1,4]dioxin-2-ylmethyl)-2-(1-methyl-piperidin-4-yl)-acetamide;
N—((R)-7-Benzyloxy-2,3-dihydro-benzo[1,4]dioxin-2-ylmethyl)-2-piperidin-4-yl-acetamide;
7-Benzyloxy-2,3-dihydro-benzo[1,4]dioxine-2-carboxylic acid 4-morpholin-4-ylmethyl-benzylamide;
7-Benzyloxy-2,3-dihydro-benzo[1,4]dioxine-2-carboxylic acid 3-morpholin-4-ylmethyl-benzylamide;
4-(4-{[(7-benzyloxy-2,3-dihydro-benzo[1,4]dioxine-2-carbonyl)-amino]-methyl}-benzyl)-piperazine-1-carboxylic acid tert-butyl ester;
7-benzyloxy-2,3-dihydro-benzo[1,4]dioxine-2-carboxylic acid 4-piperazin-1-ylmethyl-benzylamide;
7-Benzyloxy-2,3-dihydro-benzo[1,4]dioxine-2-carboxylic acid (pyridin-3-ylmethyl)-amide;
7-Benzyloxy-2,3-dihydro-benzo[1,4]dioxine-2-carboxylic acid (pyridin-4-ylmethyl)-amide;
N—((R)-7-Benzyloxy-2,3-dihydro-benzo[1,4]dioxin-2-ylmethyl)-2-pyridin-4-yl-acetamide;
7-Benzyloxy-2,3-dihydro-benzo[1,4]dioxine-2-carboxylic acid (morpholin-3-ylmethyl)-amide;
N—((R)-7-Benzyloxy-2,3-dihydro-benzo[1,4]dioxin-2-ylmethyl)-2-pyridin-3-yl-acetamide;
7-Benzyloxy-2,3-dihydro-benzo[1,4]dioxine-2-carboxylic acid (2-oxo-1,2-dihydro-pyridin-4-ylmethyl)-amide;
7-Benzyloxy-2,3-dihydro-benzo[1,4]dioxine-2-carboxylic acid (2-oxo-piperidin-4-ylmethyl)-amide;
7-Benzyloxy-2,3-dihydro-benzo[1,4]dioxine-2-carboxylic acid (2-fluoro-pyridin-4-ylmethyl)-amide;
N—((R)-7-Benzyloxy-2,3-dihydro-benzo[1,4]dioxin-2-ylmethyl)-2-(3,5-dimethyl-1H-pyrazol-4-yl)-acetamide;
7-Benzyloxy-2,3-dihydro-benzo[1,4]dioxine-2-carboxylic acid (1H-pyrazol-4-ylmethyl)-amide;
Piperidine-4-carboxylic acid ((R)-7-benzyloxy-2,3-dihydro-benzo[1,4]dioxin-2-ylmethyl)-amide:
((R)-7-Benzyloxy-2,3-dihydro-benzo[1,4]dioxin-2-ylmethyl)-piperidin-4-yl-amine;
((R)-7-Benzyloxy-2,3-dihydro-benzo[1,4]dioxin-2-ylmethyl)-morpholin-3-ylmethyl-amine;
1-Carbamoylmethyl-piperidine-4-carboxylic acid ((R)-7-benzyloxy-2,3-dihydro-benzo[1,4]dioxin-2-ylmethyl)-amide;
1-{4-[((R)-7-Benzyloxy-2,3-dihydro-benzo[1,4]dioxin-2-ylmethyl)-amino]-piperidin-1-yl}-ethanone;
5-{[((R)-7-Benzyloxy-2,3-dihydro-benzo[1,4]dioxin-2-ylmethyl)-amino]-methyl}-piperidin-2-one;
((R)-7-Benzyloxy-2,3-dihydro-benzo[1,4]dioxin-2-ylmethyl)-piperidin-3-ylmethyl-amine;
1-Methyl-piperidine-4-carboxylic acid [(R)-7-(3,4-difluoro-benzyloxy)-2,3-dihydro-benzo[1,4]dioxin-2-ylmethyl]-amide;
1-Methyl-piperidine-4-carboxylic acid [(R)-7-(3-methyl-benzyloxy)-2,3-dihydro-benzo[1,4]dioxin-2-ylmethyl]-amide;
1-Methyl-piperidine-4-carboxylic acid [(R)-7-(4-methyl-benzyloxy)-2,3-dihydro-benzo[1,4]dioxin-2-ylmethyl]-amide;
1-Methyl-piperidine-4-carboxylic acid [(R)-7-(3-chloro-benzyloxy)-2,3-dihydro-benzo[1,4]dioxin-2-ylmethyl]-amide;
1-Methyl-piperidine-4-carboxylic acid [(R)-7-(4-chloro-benzyloxy)-2,3-dihydro-benzo[1,4]dioxin-2-ylmethyl]-amide;
1-Methyl-piperidine-4-carboxylic acid [(R)-7-(4-fluoro-benzyloxy)-2,3-dihydro-benzo[1,4]dioxin-2-ylmethyl]-amide;
1-Methyl-piperidine-4-carboxylic acid [(R)-7-(2-methyl-benzyloxy)-2,3-dihydro-benzo[1,4]dioxin-2-ylmethyl]-amide; and
1-Furan-2-ylmethyl-piperidine-4-carboxylic acid ((R)-7-benzyloxy-2,3-dihydro-benzo[1,4]dioxin-2-ylmethyl)-amide.

88. A compound according to paragraph 87, or a salt or solvate thereof, selected from:
5-(4-Methyl-piperazin-1-ylmethyl)-furan-2-carboxylic acid ((R)-7-benzyloxy-2,3-dihydro-benzo[1,4]dioxin-2-ylmethyl)-amide;
Oxazole-2-carboxylic acid ((R)-7-benzyloxy-2,3-dihydro-benzo[1,4]dioxin-2-ylmethyl)-amide;
5-(4-Methyl-piperazin-1-ylmethyl)-furan-2-carboxylic acid [(R)-7-(4-methoxy-benzyloxy)-2,3-dihydro-benzo[1,4]dioxin-2-ylmethyl]-amide;
5-(4-Methyl-piperazin-1-ylmethyl)-furan-2-carboxylic acid ((R)-7-phenethyloxy-2,3-dihydro-benzo[1,4]dioxin-2-ylmethyl)-amide;
5-(4-Methyl-piperazin-1-ylmethyl)-furan-2-carboxylic acid [(R)-7-(4-chloro-benzyloxy)-2,3-dihydro-benzo[1,4]dioxin-2-ylmethyl]-amide;
5-(4-Methyl-piperazin-1-ylmethyl)-oxazole-2-carboxylic acid ((R)-7-benzyloxy-2,3-dihydro-benzo[1,4]dioxin-2-ylmethyl)-amide;
1-methyl-piperidine-4-carboxylic acid ((R)-7-benzyloxy-2,3-dihydro-benzo[1,4]dioxin-2-ylmethyl)-amide;
Oxazole-2-carboxylic acid ((R)-7-benzyloxy-2,3-dihydro-benzo[1,4]dioxin-2-ylmethyl)-[4-(3-dimethylamino-propoxy)-benzyl]-amide;
(4-{[((R)-7-Benzyloxy-2,3-dihydro-benzo[1,4]dioxin-2-ylmethyl)-(oxazole-2-carbonyl)-amino]-methyl}-benzyl)-carbamic acid tert-butyl ester;
Oxazole-2-carboxylic acid (4-aminomethyl-benzyl)-((R)-7-benzyloxy-2,3-dihydro-benzo[1,4]dioxin-2-ylmethyl)-amide;
Oxazole-2-carboxylic acid ((R)-7-benzyloxy-2,3-dihydro-benzo[1,4]dioxin-2-ylmethyl)-(1-benzyl-piperidin-4-ylmethyl)-amide;

((R)-7-Benzyloxy-2,3-dihydro-benzo[1,4]dioxin-2-ylm-ethyl)-(tetrahydro-pyran-4-ylmethyl)-amine;
Oxazole-2-carboxylic acid ((R)-7-benzyloxy-2,3-dihydro-benzo[1,4]dioxin-2-ylmethyl)-(1-benzyl-piperidin-4-yl)-amide;
1-{2-[((R)-7-Benzyloxy-2,3-dihydro-benzo[1,4]dioxin-2-ylmethyl)-amino]-2-phenyl-ethyl}-pyrrolidin-2-one;
7-Benzyloxy-2,3-dihydro-benzo[1,4]dioxine-2-carboxylic acid (1-methyl-piperidin-4-ylmethyl)-amide;
3-((R)-7-Benzyloxy-2,3-dihydro-benzo[1,4]dioxin-2-ylm-ethyl)-8-methyl-1,3,8-triaza-spiro[4.5]decane-2,4-dione;
7-Benzyloxy-2,3-dihydro-benzo[1,4]dioxine-2-carboxylic acid (1H-imidazol-2-yl)-amide;
formic acid salt;
7-Benzyloxy-2,3-dihydro-benzo[1,4]dioxine-2-carboxylic acid [4-(2-amino-acetylamino)-cyclohexyl]-amide;
3-((R)-7-Benzyloxy-2,3-dihydro-benzo[1,4]dioxin-2-ylm-ethyl)-1-piperidin-4-yl-imidazolidine-2,4-dione;
((R)-7-Benzyloxy-2,3-dihydro-benzo[1,4]dioxin-2-ylm-ethyl)-(1-methyl-piperidin-4-ylmethyl)-amine;
7-Benzyloxy-2,3-dihydro-benzo[1,4]dioxine-2-carboxylic acid 3-(4-methyl-piperazin-1-ylmethyl)-benzylamide;
N-{4-[((R)-7-Benzyloxy-2,3-dihydro-benzo[1,4]dioxin-2-ylmethyl)-amino]-cyclohexyl}-2-dimethylamino-acet-amide;
1-{2-[4-((R)-7-Benzyloxy-2,3-dihydro-benzo[1,4]dioxin-2-ylmethyl)-piperazin-1-yl]-ethyl}-1H-pyridin-2-one;
N-{4-[((R)-7-Benzyloxy-2,3-dihydro-benzo[1,4]dioxin-2-ylmethyl)-(2H-pyrazol-3-ylmethyl)-amino]-cyclohexyl}-2-dimethylamino-acetamide;
((R)-7-Benzyloxy-2,3-dihydro-benzo[1,4]dioxin-2-ylm-ethyl)-[3-(4-methyl-piperazin-1-yl)-benzyl]-amine;
N—((R)-7-Benzyloxy-2,3-dihydro-benzo[1,4]dioxin-2-yl-methyl)-3-(4-methyl-piperazin-1-ylmethyl)-benzamide;
4-(4-{[(7-benzyloxy-2,3-dihydro-benzo[1,4]dioxine-2-car-bonyl)-amino]-methyl}-benzyl)-piperazine-1-carboxylic acid tert-butyl ester;
7-benzyloxy-2,3-dihydro-benzo[1,4]dioxine-2-carboxylic acid 4-piperazin-1-ylmethyl-benzylamide;
((R)-7-Benzyloxy-2,3-dihydro-benzo[1,4]dioxin-2-ylm-ethyl)-piperidin-4-yl-amine;
((R)-7-Benzyloxy-2,3-dihydro-benzo[1,4]dioxin-2-ylm-ethyl)-piperidin-3-ylmethyl-amine;
1-Methyl-piperidine-4-carboxylic acid [(R)-7-(3,4-difluoro-benzyloxy)-2,3-dihydro-benzo[1,4]dioxin-2-ylmethyl]-amide;
1-Methyl-piperidine-4-carboxylic acid [(R)-7-(3-methyl-benzyloxy)-2,3-dihydro-benzo[1,4]dioxin-2-ylmethyl]-amide;
1-Methyl-piperidine-4-carboxylic acid [(R)-7-(4-methyl-benzyloxy)-2,3-dihydro-benzo[1,4]dioxin-2-ylmethyl]-amide;
1-Methyl-piperidine-4-carboxylic acid [(R)-7-(3-chloro-benzyloxy)-2,3-dihydro-benzo[1,4]dioxin-2-ylmethyl]-amide;
1-Methyl-piperidine-4-carboxylic acid [(R)-7-(4-chloro-benzyloxy)-2,3-dihydro-benzo[1,4]dioxin-2-ylmethyl]-amide;
1-Methyl-piperidine-4-carboxylic acid [(R)-7-(4-fluoro-benzyloxy)-2,3-dihydro-benzo[1,4]dioxin-2-ylmethyl]-amide; and
1-Methyl-piperidine-4-carboxylic acid [(R)-7-(2-methyl-benzyloxy)-2,3-dihydro-benzo[1,4]dioxin-2-ylmethyl]-amide.

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Salts and Solvates

The compounds (including final products and intermediates) described herein may be isolated and used per se or may be isolated in the form of a salt, suitably pharmaceutically acceptable salts. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one embodiment, the compounds of Formula I and sub-formulae thereof are isolated as pharmaceutically acceptable salts.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents)

and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of the Formula I and sub-formulae thereof may exist in solvated as well as unsolvated forms such as, for example, hydrated forms. It is to be understood that the invention encompasses all such solvated forms that possess the described biological activity.

Polymorphs

It is also to be understood that certain compounds of the Formula I and sub-formuale thereof may exhibit polymorphism, and that the invention encompasses all such forms that possess the described biological activity.

N-Oxides

Compounds of the Formula I and sub-formulae thereof containing an amine function may also form N-oxides. A reference herein to a compound of the Formula I and sub-formuale thereof that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

Tautomers

Compounds of the Formula I and sub-formulae thereof may exist in a number of different tautomeric forms and references to compounds of the Formula I and sub-formulae thereof include all such forms. For the avoidance of doubt, where a compound can exist in one of several tautomeric forms, and only one is specifically described or shown, all others are nevertheless embraced by Formula I and sub-formulae thereof. Examples of tautomeric forms include keto-, enol-, and enolate-forms, as in, for example, the following tautomeric pairs: keto/enol (illustrated below), pyrimidone/hydroxypyrimidine, imine/enamine, amide/imino alcohol, amidine/amidine, nitroso/oxime, thioketone/enethiol, and nitro/aci-nitro.

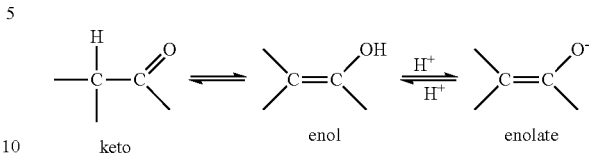

Isomers

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Certain compounds of Formula I and sub-formulae thereof may have one or more asymmetric centers and therefore can exist in a number of stereoisomeric configurations. Consequently, such compounds can be synthesized and/or isolated as mixtures of enantiomers and/or as individual (pure) enantiomers, and, in the case of two or more asymmetric centers, single diastereomers and/or mixtures of diastereomers. It should be understood that the present application includes all such enantiomers and diastereomers and mixtures thereof in all ratios.

In one embodiment, the compounds of formula I and sub-formulae thereof are the S-enantiomer or R-enantiomer, suitably the R-enantiomer.

In another embodiment, the compounds of formula I and sub-formulae thereof are racemic.

In one embodiment, where the carbon to which group $R^2$ attach is a chiral centre, the stereochemistry at this position is R or S, suitably R.

Isotopes

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^{3}H$; etc. Preferably, the constituent atoms in the compounds of the present invention are present in their naturally occurring ratios of isotope forms.

Prodrugs and Metabolites

The compounds of Formula I and sub-formulae thereof may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in-vivo cleavable amide derivatives that may be formed at a carboxy group or an amino group in a compound of the Formula I.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I and sub-formulae thereof that are produced by organic synthetic means and also such compounds that are produced in the human or animal body by way of metabolism of a precursor compound, that is a compound of the Formula I may be a synthetically-produced compound or a metabolically-produced compound.

A suitable pharmaceutically acceptable pro-drug of a compound of the Formula I and sub-formulae thereof is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
C) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the Formula I and sub-formulae thereof that possesses a carboxy group is, for example, an in vivo cleavable ester thereof. An in vivo cleavable ester of a compound of the Formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$ alkoxycarbonyloxy-$C_{1-6}$alkyl esters such as methoxycarbonyloxymethyl and 1-methoxycarbonyloxyethylesters.

A suitable pharmaceutically acceptable pro-drug of a compound of the Formula I and sub-formulae thereof that possesses a hydroxy group is, for example, an in vivo cleavable ester or ether thereof. An in vivo cleavable ester or ether of a compound of the Formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula I and sub-formulae thereof that possesses a carboxy group is, for example, an in vivo cleavable amide thereof, for example an amide formed with an amine such as ammonia, a $C_{1-4}$ alkylamine such as methylamine, a $(C_{1-4}alkyl)_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the Formula I and sub-formulae thereof that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the Formula I and sub-formulae thereof may be exerted in part by one or more metabolites that are formed within the human or animal body after administration of a compound of the Formula I and sub-formulae thereof. As stated hereinbefore, the in vivo effects of a compound of the Formula I and sub-formulae thereof may also be exerted by way of metabolism of a precursor compound (a pro-drug).

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of RAS-effector protein-protein interaction.

The present invention therefore provides a method of inhibiting a RAS-effector protein-protein interaction in vitro or in vivo, said method comprising contacting a cell with an effective amount of a compound, or a pharmaceutically acceptable salt, hydrate or solvate thereof, as defined herein.

The present invention also provides a method of treating a disease or disorder wherein an aberrant RAS-effector interaction is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of inhibiting cell proliferation, in vitro or in vivo, said method comprising contacting a cell with an effective amount of a compound, or a pharmaceutically acceptable salt, hydrate or solvate thereof, as defined herein.

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, as defined herein for use in the inhibition of a RAS-effector protein-protein interaction, suitably an aberrant RAS-effector protein-protein interaction.

The present invention provides a compound, or a pharmaceutically acceptable salt, hydrate or solvate thereof, as defined herein for use in the treatment of a disease or disorder in which aberrant RAS-effector protein-protein interaction is implicated.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the inhibition of a RAS-effector protein-protein interaction, suitably an aberrant RAS-effector protein-protein interaction.

The present invention provides a use of a compound, or a pharmaceutically acceptable salt, hydrate or solvate thereof, as defined herein in the manufacture of a medicament for the treatment of a disease or disorder in which an aberrant RAS-effector protein-protein interaction is implicated.

The term "proliferative disorder" used herein pertains to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis.

Any type of cell may be treated, including but not limited to, lung, colon, breast, ovarian, prostate, liver, pancreas, brain, and skin.

The anti-proliferative effects of the compounds of the present invention have particular application in the treatment of human cancers (for instance, by virtue of their inhibition of RAS-effector protein-protein interactions).

In one embodiment, the compounds inhibit interaction of RAS (suitably NRAS, KRAS or HRAS, more suitably KRAS) with one or more effector proteins.

In another embodiment, the compounds inhibit interaction of RAS with one or more effector proteins selected from PLCε(epsilon), PKCζ(zeta), PI3K, RASSF, RAF, RalGEF, RIN, AF-6, GAP and TIAM1, suitably selected from PI3K, RAF and RalGEF.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In a particular embodiment of the invention, the proliferative condition to be treated is cancer. For example, lung cancer, colon cancer, rectum cancer, breast cancer, ovarian cancer, prostate cancer, liver cancer, pancreatic cancer, brain cancer and skin cancer.

In one embodiment, the cancer is selected from pancreatic cancer, colon cancer, rectum cancer and lung cancer.

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXAMPLES

Chemistry

The following examples are provided solely to illustrate the present invention and are not intended to limit the scope of the invention, as described herein.

The compounds of the invention may be prepared using synthetic techniques that are known in the art (as illustrated by the examples herein).

Several methods for the chemical synthesis of the compounds of the present application are described herein. These and/or other well-known methods may be modified and/or adapted in various ways in order to facilitate the synthesis of additional compounds within the scope of the present application and claims. Such alternative methods and modifications should be understood as being within the spirit and scope of this application and claims. Accordingly, it should be understood that the methods set forth in the following descriptions, schemes and examples are intended for illustrative purposes and are not to be construed as limiting the scope of the disclosure.

Synthesis and Characterisation

Analytical Methods

Analysis of products and intermediates has been carried out using reverse phase analytical HPLC-MS using the parameters set out below.

HPLC Analytical Methods

AnalpH2_MeOH_4 min: Phenomenex Luna C18 (2) 3 μm, 50×4.6 mm; A=water+0.1% formic acid; B=MeOH+ 0.1% formic acid; 45° C.; % B: 0.0 min 5%, 1.0 min 37.5%, 3.0 min 95%, 3.5 min 95%, 3.51 min 5%, 4.0 min 5%; 2.25 mL/min.

AnalpH9_MeOH_4 min: Phenomenex Luna C18 (2) 3 μm, 50×4.6 mm; A=water pH 9 (Ammonium Bicarbonate 10 mM); B=MeOH+0.1% formic acid; 45° C.; % B: 0.0 min 5%, 1.0 min 37.5%, 3.0 min 95%, 3.5 min 95%, 3.51 5%, 4.0 min 5%; 2.25 mL/min.

AnalpH2_MeOH_QC_V1: Phenomenex Gemini NX C18 5 μm, 150×4.6 mm; A=water+0.1% formic acid; B=MeOH+ 0.1% formic acid; 40° C.; % B: 0.0 min 5%, 0.5 min, 5%, 7.5 min 95%, 10.0 min 95%, 10.1 min 5%, 13.0 min 5%; 1.5 mL/min.

AnalpH9_MeOH_QC_V1: Phenomenex Gemini NX C18 5 μm, 150×4.6 mm; A=water+pH 9 (Ammonium Bicarbonate 10 mM); B=MeOH; 40° C.; % B: 0.0 min 5%, 0.50 min 5%, 7.5 min 95%, 10.0 min 95%, 10.1 min 5%, 13.0 min 5%; 1.5 mL/min.

UPLC Analytical Methods

AnalpH2_MeCN_UPLC_4 min: Acquity UPLC BEH C-18 1.7 μm, 2.1×50 mm, A=water+0.05% formic acid; B: acetonitrile+0.05% formic acid; 35° C.; % B: 0.0 min 10%, 0.5 min 10%, 1 min 35%, 1.5 min 45%, 2.3 min 90%, 3.2 min 90%, 3.6 min 10%, 4 min 10%; 0.55 mL/min.

NMR Methods $^1$H-NMR: Spectra were obtained on a Bruker DRX 400 MHz or Jeol ECS 400 MHz or Agilent MRDD2 400 MHz spectrometer. Spectra are measured at 294K (unless otherwise stated) and chemical shifts (δ-values) are reported in parts per million (ppm), referenced to either TMS (0.0 ppm), DMSO-d6 (2.50 ppm), CDCl3 (7.26 ppm). Coupling constants (J) are reported in Hertz (Hz), spectra splitting pattern are designated as singlet (s), doublet (d), triplet (t), quadruplet (q), multiplet or more overlapping signals (m), broad signal (br); solvent is given in parentheses.

Abbreviations

The following abbreviations are used in the Examples and other parts of the description.
Boc: tert-butyloxycarbonyl
DBU: 1,8-diazabicyclo[5.4.0]undec-7-ene
DCM: dichloromethane
dioxane: 1,4-dioxane
DIPEA: N,N-diisopropylethylamine
DMF: N,N-dimethylformamide
DMSO: dimethylsulfoxide
EtOAc: ethyl acetate
h: hour(s)
HBTU: (2-(1H-benzotriazol-1-yl)-1,1,3,3-tetramethyluronium hexafluorophosphate
HPLC: High-performance liquid chromatography
LCMS: Liquid chromatography-mass spectrometry
MS: mass spectroscopy
Pet-ether: petroleum ether (b.p. 60-80° C.)
quant.: quantitative (conversion)
Rt: retention time
RT: room temperature
SCX: strong cation exchange
TEA: triethylamine
TFA: trifluoroacetic acid
THF: tetrahydrofuran
TsCl: p-toluenesulfonyl chloride
General Procedures
General Procedure A—Amide Coupling Using HBTU A mixture of carboxylic acid (1.0-1.5 eq), amine (1.0 eq), N,N-diisopropylethylamine (3.0 eq) and HBTU (2-(1H-benzotriazol-1-yl)-1,1,3,3-tetramethyluronium hexafluorophosphate) (1 eq) in anhydrous DMF or DCM was stirred at room temperature for 1-72 h. The product was isolated and purified using one of the following methods:

A1) The reaction mixture was concentrated in vacuo and the resulting residue loaded onto a SCX cartridge, washed with methanol then eluted with a solution of ammonia in methanol and the product-containing fractions concentrated in vacuo. The compound was purified by column chromatography or by preparative HPLC.

A2) The reaction mixture was diluted with a mixture of water and aqueous sat. NaCl solution and extracted with EtOAc. The organic phase was dried over $Na_2SO_4$ or $MgSO_4$, filtered and concentrated in vacuo to yield the crude material which was purified by column chromatography or preparative HPLC.
General Method B—Mitsunobu Reaction To a stirred mixture of aryl alcohol (1 eq.), alcohol (3 eq.) and triphenylphosphine (3 eq.) in anhydrous 1,4-dioxane was added dropwise diisopropyl azodicarboxylate (3 eq.) and the reaction was stirred at room temperature for 1-72 h. The product was isolated and purified using one of the following methods:

B1) The reaction mixture was loaded onto a SCX-2 cartridge, washed with methanol then eluted with ammonia in methanol and concentrated in vacuo. The compound was purified by either column chromatography or reverse phase preparative HPLC.

B2) The reaction mixture was concentrated in vacuo and the resulting residue was purified by either column chromatography or reverse phase preparative HPLC.

General Procedure C—Reductive Alkylation Using NaBH(OAc)$_3$

To a solution of the aldehyde (1.2 eq) in anhydrous DCM or MeOH under $N_2$ at 0° C. or RT was added the amine (1.0-1.3 eq) following by AcOH (1 eq) and the mixture was stirred for 0.5-2 hr. Then NaBH(OAc)$_3$ (2 eq) was added and stirred at RT for 2-16 hr. Then the volatiles were removed in vacuo. The residue was taken up in EtOAc or DCM, washed with NaHCO$_3$(aq) solution, $H_2O$ then brine. The organic phase was dried over $Na_2SO_4$, $MgSO_4$ or passed through a hydrophobic frit. The volatiles were removed under reduced pressure to yield the crude material which was purified by column chromatography or prep HPLC.
General Procedure D—Reductive Amination Using NaBH(OAc)$_3$ To a solution of the aldehyde (1 eq) in anhydrous DCM or MeOH under $N_2$ at 0° C. or RT was added the amine (1.2 eq) followed by AcOH (1 eq) and the reaction mixture stirred for 0.5-2 hr. Then NaBH(OAc)$_3$ (2 eq) was added and the mixture stirred at RT for 16 hr. Then the volatiles were removed in vacuo.

D1) The residue was taken up in EtOAc, washed with NaHCO$_3$(aq) solution, $H_2O$ then brine. The organic phase was dried over $Na_2SO_4$ or $MgSO_4$, filtered and concentrated in vacuo to yield the crude material which was purified by column chromatography or prep HPLC; or D2) The residue was loaded onto a SCX cartridge, washed with methanol then eluted with ammonia in methanol and the product-containing fractions were concentrated in vacuo to yield the crude material which was purified by column chromatography or reverse phase preparative HPLC.
General Procedure E—BOC Removal A solution of Boc protected amine in TFA:DCM was stirred at room temperature and monitored by LCMS. On consumption of starting material, the product was isolated and purified using one of the following methods:

E1) The reaction was concentrated in vacuo and the resulting residue was loaded onto a SCX-2 cartridge, washed with methanol then eluted with ammonia in methanol and concentrated in vacuo. The compound was purified by column chromatography or by reverse phase preparative HPLC.

E2) The reaction was concentrated in vacuo, then the crude was neutralised with a solution of ammonia in methanol (0.5M-7.0M) and concentrated in vacuo. The compound was purified by reverse phase preparative HPLC.
Preparations Synthesis of ethyl 5-(bromomethyl)oxazole-2-carboxylate

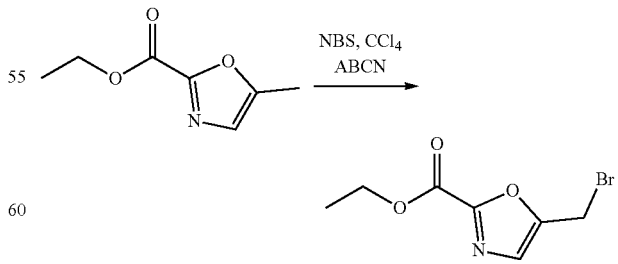

A solution of ethyl 5-methyloxazole-2-carboxylate (1 eq, 1.29 mmol), N-bromosuccinimide (1.2 eq, 1.54 mmol), and azobiscyclohexanecarbonitrile (ABCN, 0.1 eq, 0.12 mmol) in CCl$_4$ (5 ml) was heated at 80 C for 4 h. Then the reaction was cooled to RT, filtered through celite and washed with dichloromethane and concentrated in vacuo. The crude product was purified by column chromatography on silica gel eluting with 0-20% ethyl acetate in isohexane to afford ethyl 5-(bromomethyl)oxazole-2-carboxylate (250 mg, 83%) as a pale yellow oil.

AnalpH2_MeOH_4 min, Rt: 2.44 min; m/z 234/236 [M+H]$^+$

Synthesis of ethyl 5-[(4-methylpiperazin-1-yl)methyl]oxazole-2-carboxylate

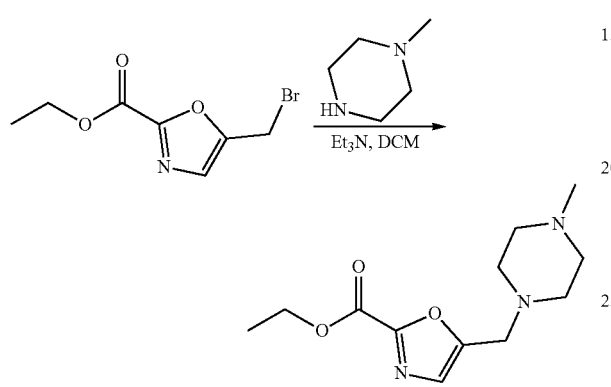

A solution of ethyl 5-(bromomethyl)oxazole-2-carboxylate (1 eq, 2.56 mmol), 1-methylpiperazine (1.1 eq, 2.82 mmol), triethylamine (1.2 eq, 3.07 mmol) in DCM (10 mL) was stirred at RT for 12 h. Water was then added to the mixture and the compound was extracted with dichloromethane. The organic extract was dried over MgSO$_4$ and concentrated in vacuo to afford ethyl 5-[(4-methylpiperazin-1-yl)methyl]oxazole-2-carboxylate (500 mg, 77%) as a yellow oil.

AnalpH2_MeOH_4 min, Rt: 2.13 min; m/z 254 [M+H]$^+$

Synthesis of 5-[(4-methylpiperazin-1-yl)methyl]oxazole-2-carboxylic acid. lithium salt

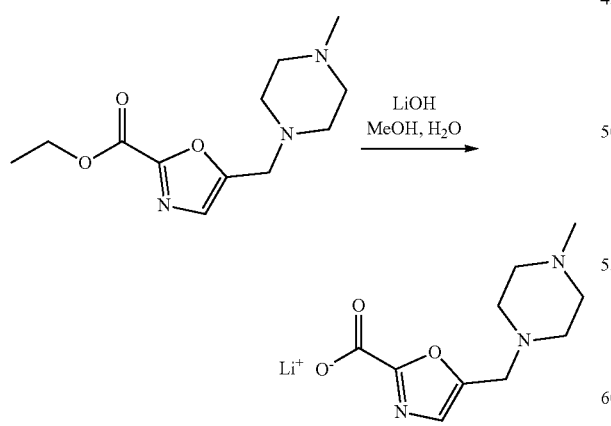

To a solution of ethyl 5-[(4-methylpiperazin-1-yl)methyl]oxazole-2-carboxylate (1 eq, 1.98 mmol) in 1:1 MeOH:H$_2$O (10 mL) was added LiOH (1 eq, 1.98 mmol) and the mixture was stirred at RT for 2 h. The mixture was then concentrated under reduced pressure. Methanol was added and concentrated in vacuo. The compound was then dissolved in MeCN:H$_2$O and lyophilised to afford 5-[(4-methylpiperazin-1-yl)methyl]oxazole-2-carboxylic acid. lithium salt (403 mg, 88%) as a white solid.

AnalpH2_MeOH_4 min, Rt: 0.31 min, m/z 226 [M+H]$^+$

Synthesis of 1-methyl-piperidine-4-carboxylic acid ((R)-7-hydroxy-2,3-dihydro-benzo[1,4]dioxin-2-ylmethyl)-amide

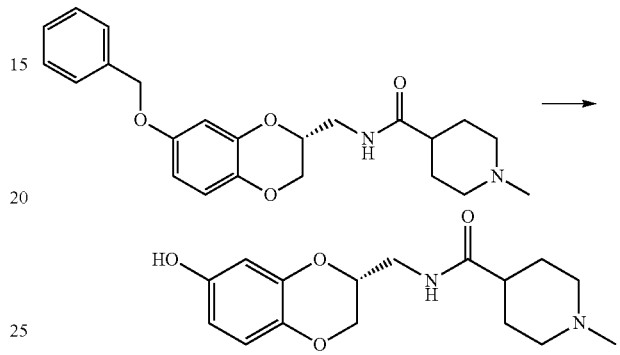

A mixture of 1-methyl-piperidine-4-carboxylic acid ((R)-7-benzyloxy-2,3-dihydro-benzo[1,4]dioxin-2-ylmethyl)-amide (4.40 mMol, 1 eq.) and 10% w/w palladium on carbon (234 mg, 5 mol %) in ethanol was placed under an atmosphere of hydrogen and allowed to stir at room temperature for 16 h. The reaction mixture was filtered through celite, the residue washed with ethanol and the combined filtrate concentrated in vacuo to afford 1-methyl-piperidine-4-carboxylic acid ((R)-7-hydroxy-2,3-dihydro-benzo[1,4]dioxin-2-ylmethyl)-amide as an off white solid (1.42 g, 0.46 mMol, 105%). The crude product was used without further purification.

AnalpH2_MeOH_4MIN, Rt: 1.85 min, m/z 307.3 [M+H]$^+$

Synthesis of 5-(4-methyl-piperazin-1-ylmethyl)-furan-2-carboxylic acid ((R)-7-hydroxy-2,3-dihydro-benzo[1,4]dioxin-2-ylmethyl)-amide

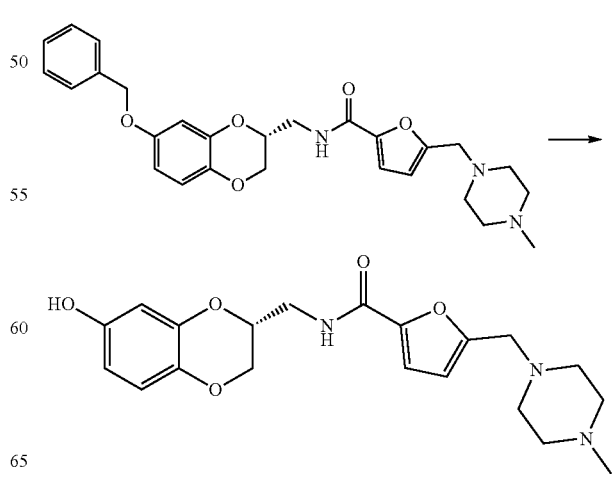

A mixture of 5-(4-methyl-piperazin-1-ylmethyl)-furan-2-carboxylic acid ((R)-7-benzyloxy-2,3-dihydro-benzo[1,4]dioxin-2-ylmethyl)-amide (562 mg, 1.12 mMol, 1 eq.) and 10% w/w palladium on carbon (60 mg, 5 mol %) in ethanol was placed under an atmosphere of hydrogen and allowed to stir at room temperature for 4 h. The reaction mixture was filtered through celite, the residue washed with ethanol and the combined filtrates concentrated in vacuo to afford 5-(4-methyl-piperazin-1-ylmethyl)-furan-2-carboxylic acid ((R)-7-hydroxy-2,3-dihydro-benzo[1,4]dioxin-2-ylmethyl)-amide as a pale yellow solid (445 mg, 1.15 mMol, 102%). The crude product was used without further purification.

AnalpH2_MeOH_4MIN, Rt: 1.39 min, m/z 388.32 [M+H]$^+$

Synthesis of Oxazole-2-carboxylic acid ((R)-7-hydroxy-2,3-dihydro-benzo[1,4]dioxin-2-ylmethyl)-amide

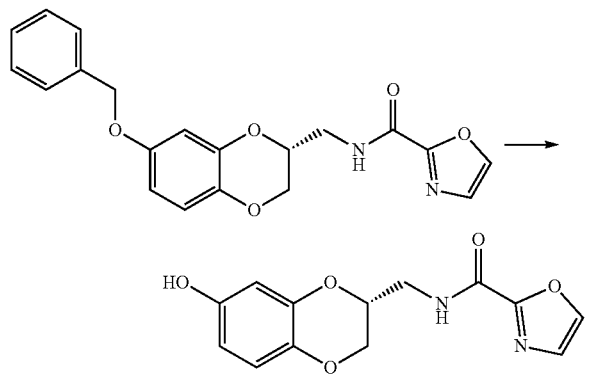

To a mixture of oxazole-2-carboxylic acid ((R)-7-benzyloxy-2,3-dihydro-benzo[1,4]dioxin-2-ylmethyl)-amide (318 mg, 0.87 mMol, 1 eq.) and 10% w/w palladium on carbon (30 mg,) was added ammonium formate (548 mg, 8.69 mMol, 10 eq.) and the mixture heated at 80° C. for 1 h. The reaction was filtered through celite, the residue washed with ethanol and the combined filtrate concentrated in vacuo. The residue was partitioned between sat. aq. NaHCO$_3$ solution and EtOAc. The organic layer was separated, dried (MgSO$_4$) and concentrated in vacuo to afford oxazole-2-carboxylic acid ((R)-7-hydroxy-2,3-dihydro-benzo[1,4]dioxin-2-ylmethyl)-amide as a white solid (240 mg). The crude product was used without further purification.

AnalpH2_MeOH_4MIN, Rt: 1.99 min, m/z 277 [M+H]$^+$

Synthesis of 1-[5-Benzyloxy-2-((S)-1-oxiranyl-methoxy)-phenyl]-ethanone

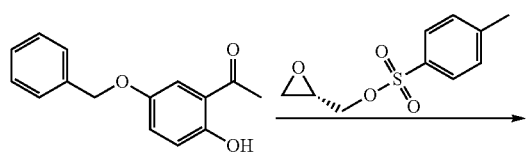

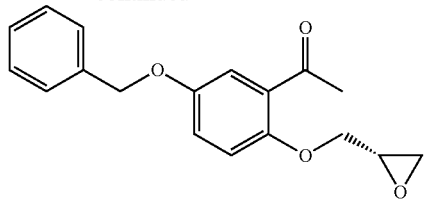

To a solution 1-(5-benzyloxy-2-hydroxy-phenyl)-ethanone (40 g, 165 mmol) in DMF (400 mL) was added K$_2$CO$_3$ (86 g, 190 mmol) and followed by (S)-oxiran-2-ylmethyl 4-methylbenzenesulfonate (37.7 g, 165 mmol) slowly at room temperature. The mixture was stirred at 80° C. for 6 h under an atmosphere of nitrogen. The reaction mixture was diluted with water (500 mL) and extracted with EtOAc (2×200 mL). The combined organic layer was washed with water (300 mL) and brine (300 mL), dried (Na$_2$SO$_4$) and concentrated under reduced pressure. Purification by column chromatography afforded 1-[5-benzyloxy-2-((S)-1-oxiranyl-methoxy)-phenyl]-ethanone as a pale yellow solid (42 g, 140 mMol, 85.7%).

AnalpH2_MeCN_UPLC_4 min: Rt: 2.15 min. m/z 299.4 [M+H]$^+$ $^1$H NMR (400 MHz, CDCl3) δ 2.66 (s, 3H), 2.74-2.76 (m, 1H), 2.91-2.93 (m, 1H), 3.35-3.39 (m, 1H), 3.93-3.98 (m, 1H), 4.30-4.33 (m, 1H), 5.04 (s, 2H), 6.90 (d, J=9.2 Hz, 1H), 7.06-7.09 (m, 1H), 7.30-7.43 (m, 6H).

Synthesis of Acetic acid 5-benzyloxy-2-((S)-1-oxiranylmethoxy)-phenyl ester

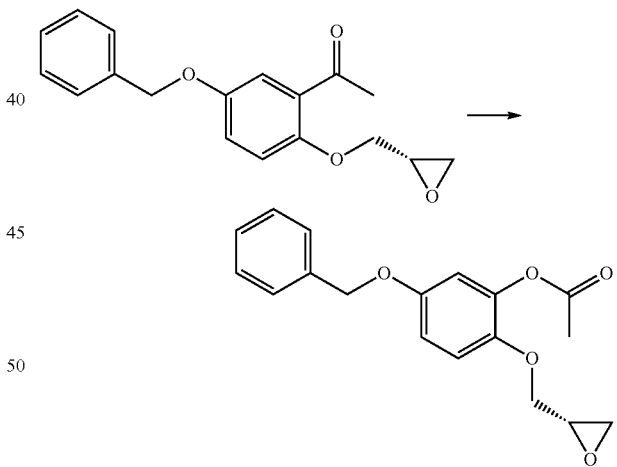

To a solution of 1-[5-benzyloxy-2-((S)-1-oxiranyl-methoxy)-phenyl]-ethanone (42 g, 140 mmol) in anhydrous DCM (600 mL) was added m-chloroperbenzoic acid (72.5 g, 425 mmol). The resulting mixture was stirred at room temperature for 16 h under an atmosphere of nitrogen. A second portion of m-chloroperbenzoic acid (72.5 g, 425 mmol) was added and the reaction mixture was stirred at room temperature for 24 h. The reaction mixture was quenched with water and extracted with DCM (3×300 mL). The organic layer was washed with sat. Na$_2$CO$_3$ solution and brine, dried (Na$_2$SO$_4$) and concentrated under reduced pressure to afford acetic acid 5-benzyloxy-2-((S)-1-oxiranylmethoxy)-phenyl ester as an off white solid (38 g, 121 mMol, 79.2%) which was used in the next step without further purification.

Synthesis of ((R)-7-Benzyloxy-2,3-dihydro-benzo[1,4]dioxin-2-yl)-methanol

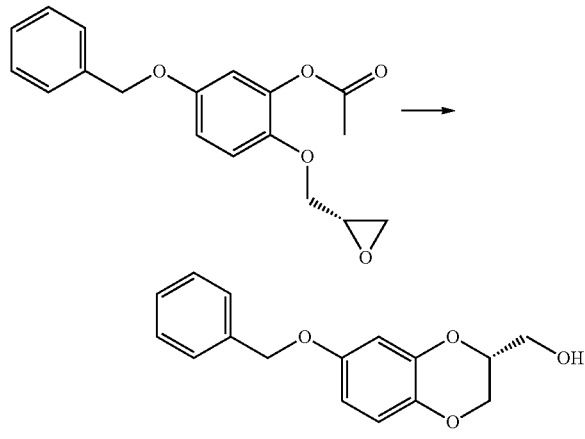

To a solution of acetic acid 5-benzyloxy-2-((S)-1-oxiranylmethoxy)-phenyl ester (50 g, 160 mMol) in MeOH (400 ml) was added a 25% solution of NaOMe in MeOH (2.59 g, 48.0 mMol). The mixture was stirred at room temperature under an atmosphere of nitrogen for 6 h. The reaction mixture was quenched with water and extracted with DCM (3×200 mL). The organic layer was washed with water, brine, dried (Na$_2$SO$_4$) and concentrated under reduced pressure. Purification by column chromatography afforded ((R)-7-benzyloxy-2,3-dihydro-benzo[1,4]dioxin-2-yl)-methanol as a grey solid (28.0 g, 103 mMol, 65%).

AnalpH2_MeCN_UPLC_4 min; Rt: 2.04 min, m/z 273.4 [M+H]$^+$ $^1$H NMR (400 MHz, CDCl$_3$) 3.79-3.89 (m, 2H), 4.03-4.07 (m, 1H), 4.22-4.27 (m, 2H), 4.98 (s, 2H), 6.48-6.56 (m, 2H), 6.79 (d, J=8 Hz, 1H), 7.29-7.42 (m, 5H).

Synthesis of (S)-7-Benzyloxy-2,3-dihydro-benzo[1,4]dioxine-2-carbaldehyde

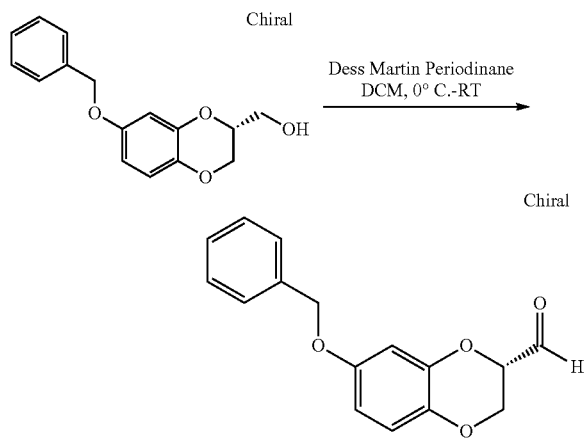

To a solution of ((R)-7-benzyloxy-2,3-dihydro-benzo[1,4]dioxin-2-yl)-methanol (1.0 eq, 1.83 mmol) anhydrous DCM (8 ml) at RT was added Dess-Martin periodinane (1.1 eq, 2.01 mmol) and the reaction was stirred at RT for 1.5 h. Once complete the reaction mixture was filtered through celite, and the filtrate was stirred with NaHCO$_3$/Na$_2$S$_2$O$_3$ 1:1 (10 mL) for 30 mins. The compound was extracted with dichloromethane, washed with water, brine, dried over magnesium sulphate and concentrated in vacuuo to give an orange oil. The crude oil was dissolved in MeOH, filtered to remove the insoluble salts, and the filtrate evaporated to dryness to give (S)-7-benzyloxy-2,3-dihydro-benzo[1,4]dioxine-2-carbaldehyde (628 mg, quant.) as a pale yellow oil. The compound was used in subsequent reactions without further purification.

AnalpH2_MeOH_4 min: Rt: 3.07 min, m/z 271.2[M+H]$^+$

Synthesis of N-(4-amino-cyclohexyl)-2-dimethylamino-acetamide

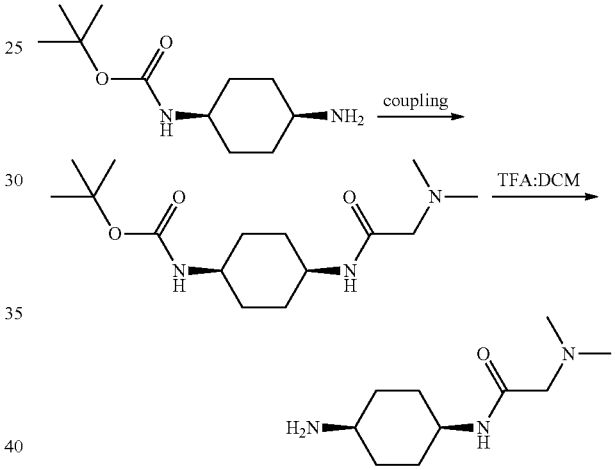

To a stirred solution of cis (4-amino-cyclohexyl)-carbamic acid tert-butyl ester (265 mg; 0.7 mmol) in DMF (2 mL) was added HBTU (265 mg, 0.7 mmol, 1 eq), N,N-dimethylglycine (72 mg, 0.7 mmol, 1 eq) and DIPEA (0.37 mL, 2.1 mmol, 3 eq), and the reaction mixture stirred at room temperature for 3 h. The reaction mixture was concentrated under reduced pressure, dissolved in EtOAc (5 mL) and washed with NaHCO$_3$ aq. solution (5 mL). The organic layer was dried over MgSO$_4$ and the solvent removed to afford the crude [4-(2-dimethylamino-acetylamino)-cyclohexyl]-carbamic acid tert-butyl ester (209 mg) which was used directly in the subsequent reaction.

The crude [4-(2-dimethylamino-acetylamino)-cyclohexyl]-carbamic acid tert-butyl ester (209 mg; assume 0.7 mmol) was dissolved in DCM (8 mL) and TFA (2 mL) added. The reaction mixture was stirred at room temperature for 3 hours. The solvent was removed and the resulting residue loaded onto a SCX-2 cartridge, washed with methanol and then eluted with a solution of ammonia in methanol. The product-containing fractions were concentrated under reduced pressure to afford the crude N-(4-amino-cyclohexyl)-2-dimethylamino-acetamide (123 mg, 0.62 mmol, 88% over 2 steps) which was used directly in subsequent reaction.

Synthesis of 7-Benzyloxy-2,3-dihydro-benzo[1,4]dioxine-2-carboxylic acid

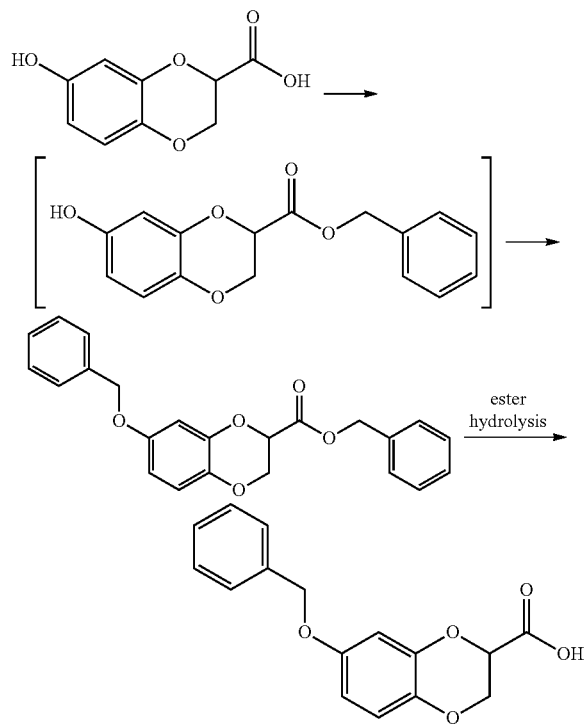

To a stirred solution of 7-hydroxy-2,3-dihydro-benzo[1,4]dioxine-2-carboxylic acid (5.00 g, 25.5 mmol) in MeCN (50 mL) was added DMF (10 mL) to aid dissolution. $K_2CO_3$ (10.6 g, 76.5 mmol) and benzyl bromide (6.35 mL, 53.5 mmol) were added whereupon the reaction mixture formed a viscous gel. A further aliquot of MeCN (70 mL) was added to the reaction mixture and stirred at 60 C overnight. The mixture was filtered to remove the fine white suspension and the filtrate was concentrated to dryness under reduced pressure. The residue was dissolved in EtOAc and washed with aq. $NaHCO_3$, 1N aq. HCl, dried over $MgSO_4$ and the solvent removed under reduced pressure to afford 7-hydroxy-2,3-dihydro-benzo[1,4]dioxine-2-carboxylic acid benzyl ester (9.5 g) as a crude product.

A sample of this crude 7-hydroxy-2,3-dihydro-benzo[1,4]dioxine-2-carboxylic acid benzyl ester (7.44 g, assumed 20 mmol) was dissolved in DMF (60 mL). $K_2CO_3$ (4.31 g, 31.2 mmol) was added followed by benzyl bromide (3.70 mL, 31.2 mmol) and the reaction mixture stirred at 60 C for 7 hours and stirred at room temperature overnight. The solvent was removed under reduced pressure and the residue was dissolved in EtOAc. The organic layer was washed with aq. $Na_2CO_3$, dried over $MgSO_4$ and the solvent removed under reduced pressure to afford 7-benzyloxy-2,3-dihydro-benzo[1,4]dioxine-2-carboxylic acid benzyl ester (1.36 g, 3.6 mmol, 18%)

To a stirred solution of 7-benzyloxy-2,3-dihydro-benzo[1,4]dioxine-2-carboxylic acid benzyl ester (322 mg, 0.855 mmol) in a 1:1:1 mixture of THF (8 mL): MeOH (8 mL): $H_2O$ (8 mL) was added LiOH monohydrate (72 mg, 1.71 mmol, 2 eq) and the reaction mixture heated at 60 C for 90 mins. The solvent was removed under reduced pressure, the residue dissolved in EtOAc. The organic layer was washed with 1N HCl aq., water, dried over $MgSO_4$ and the solvent removed under reduced pressure. The residue was re-dissolved in EtOAc and extracted into aq. $Na_2CO_3$ solution. The aqueous layer was acidified with 2M HCl aq. and extracted into EtOAc. The organic layer was dried over $MgSO_4$ and the solvent removed to afford 7-benzyloxy-2,3-dihydro-benzo[1,4]dioxine-2-carboxylic acid (229 mg, 0.80 mmol, 94%).

ANALPH2_MEOH_4MIN Rt: 3.21 min, m/z 287.2 $[M+H]^+$

Synthesis of 4-(4-Aminomethyl-benzyl)-piperazine-1-carboxylic acid tert-butyl ester

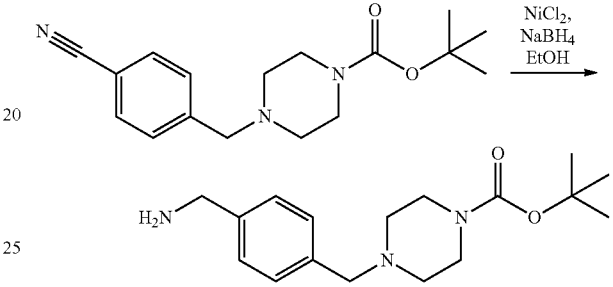

To a stirred solution of 4-(4-cyano-benzyl)-piperazine-1-carboxylic acid tert-butyl ester (300 mg, 0.99 mmol, 1 eq) in EtOH (10 mL) at 0° C. were added $NiCl_2$ (154 mg, 1.18 mmol, 1.2 eq) and $NaBH_4$ (113, 2.98 mmol, 3 eq) and the mixture was allowed to warm from 0° C. to RT over 2 h; followed by stirring for 3 h at RT. The solvent was removed and to the dark residue was added $NH_4OH$ 28%/ethyl acetate 1:1 (50 mL) with stirring, until the aqueous turned into purple. The reaction mixture was then extracted with EtOAc, and the organic extract washed with water, brine, dried over magnesium sulphate, and concentrated in vacuo to give 4-(4-aminomethyl-benzyl)-piperazine-1-carboxylic acid tert-butyl ester (290 mg, 96%) as a light yellow oil which solidified over time on standing. The crude material was used without further purification.

AnalpH9_MeOH_4 min, Rt: 2.77 min, m/z 306.4 $[M+H]^+$

Synthesis of 1-pyridin-2-yl-imidazolidine-2,4-dione

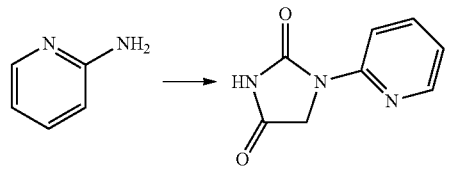 [SMILES: Nc1ccccn1 ; O=C1CN(c2ccccn2)C(=O)N1]

To a solution of pyridin-2-ylamine (0.5 g, 5.30 mmol, 1 eq) in dioxane (10 mL) under an atmosphere of nitrogen and at room temperature was added chloroacetyl isocyanate (0.63 g, 5.30 mmol, 1 eq,) and the reaction mixture was stirred for 2.25 h. DBU (2 mL, 13.3 mmol, 2.5 eq,) was added and the mixture was stirred at room temperature for 16 h. The reaction mixture was concentrated in vacuo and the resulting residue was purified column chromatography to afford 1-pyridin-2-yl-imidazolidine-2,4-dione as a white solid (408 mg, 2.30 mMol, 43%).

AnalpH2_MeOH_4MIN: Rt: 1.76 min, m/z 178 [M+H]+

Synthesis of (S)-7-benzyloxy-2-bromomethyl-2,3-dihydro-benzo[1,4]dioxine

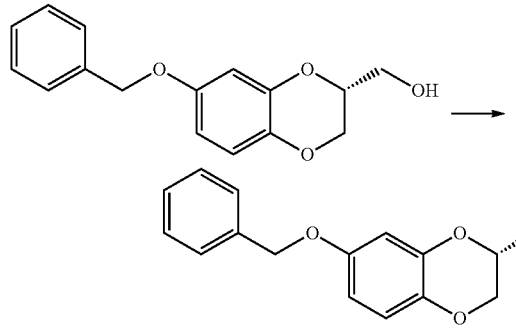

To a solution of ((R)-7-benzyloxy-2,3-dihydro-benzo[1,4]dioxin-2-yl)-methanol (100 mg, 0.37 mMol, 1.0 eq.) in DCM (10 mL) at 0° C. was added tetrabromomethane (366 mg, 1.1 mMol, 3.0 eq.) and triphenylphosphine (289 mg, 1.0 mMol, 3.0 eq.). The reaction mixture was stirred at room temperature for 13 days. The reaction mixture was concentrated in vacuo and the residue was used in the next step without further purification.

Synthesis of 4-(2,4-Dioxo-imidazolidin-1-yl)-piperidine-1-carboxylic acid tert-butyl ester To a solution of tert-butyl 4-[(2-ethoxy-2-oxo-ethyl)amino]piperidine-1-carboxylate (3.84 mmol, 1.0 eq) in water (21 ml) under nitrogen atmosphere was added potassium cyanate (1 eq, 3.84 mmol) and AcOH (7 mL) to adjust the pH of the reaction to 5.

The mixture was then heated to 40° C. for 15 h. The reaction was then quenched with sodium hydrogen carbonate and the compound was extracted with ethyl acetate, washed with water, brine, dried over sodium sulphate, filtered and concentrated in vacuo to give 4-(2,4-dioxo-imidazolidin-1-yl)-piperidine-1-carboxylic acid tert-butyl ester. AnalpH2_MeOH_4MIN: Rt: 2.53 min, m/z 284.2 [M+H]+

Synthesis of 5-(4-Methyl-piperazin-1-ylmethyl)-furan-2-carboxylic acid ((R)-7-nitro-2,3-dihydro-benzo[1,4]dioxin-2-ylmethyl)-amide The title compound was prepared by general amide coupling method A, using C—((R)-7-nitro-2,3-dihydro-benzo[1,4]dioxin-2-yl)-methylamine and 5-(4-methyl-piperazin-1-ylmethyl)-furan-2-carboxylic acid in DMF, and isolated using work-up method A1 to afford 5-(4-methyl-piperazin-1-ylmethyl)-furan-2-carboxylic acid ((R)-7-nitro-2,3-dihydro-benzo[1,4]dioxin-2-ylmethyl)-amide (676 mg, 64%) as an orange solid.

AnalpH2_MeOH_QC_V1, Rt: 4.71 min, m/z 417.2 [M+H]+

AnalpH9_MeOH_QC_V1, Rt: 7.32 min, m/z 417.2 [M+H]+

Synthesis of 5-(4-Methyl-piperazin-1-ylmethyl)-furan-2-carboxylic acid ((R)-7-amino-2,3-dihydro-benzo[1,4]dioxin-2-ylmethyl)-amide To a stirred solution of 5-(4-methyl-piperazin-1-ylmethyl)-furan-2-carboxylic acid ((R)-7-nitro-2,3-dihydro-benzo[1,4]dioxin-2-ylmethyl)-amide (676 mg, 1.6 mmol) in EtOH (20 mL) under hydrogen atmosphere was added 10% palladium on carbon (20 mg). The reaction mixture was stirred overnight, filtered through celite, washed with MeOH and the combined filtrate concentrated under reduced pressure. The resulting residue was loaded onto a SCX-2 cartridge, washed with methanol, then eluted with a solution of 0.5M ammonia in methanol and the product-containing fractions concentrated in vacuo to give 5-(4-methyl-piperazin-1-ylmethyl)-furan-2-carboxylic acid ((R)-7-amino-2,3-dihydro-benzo[1,4]dioxin-2-ylmethyl)-amide (630 mg, 100%) as a pink solid.

AnalpH2_MeOH_QC_V1, Rt: 1.25 min, m/z 387.2 [M+H]+

AnalpH9_MeOH_QC_V1, Rt: 6.04 min, m/z 387.3 [M+H]+

Route to C—[(R)-7-(4-Chloro-benzyloxy)-2,3-dihydro-benzo[1,4]dioxin-2-yl]-methylamine

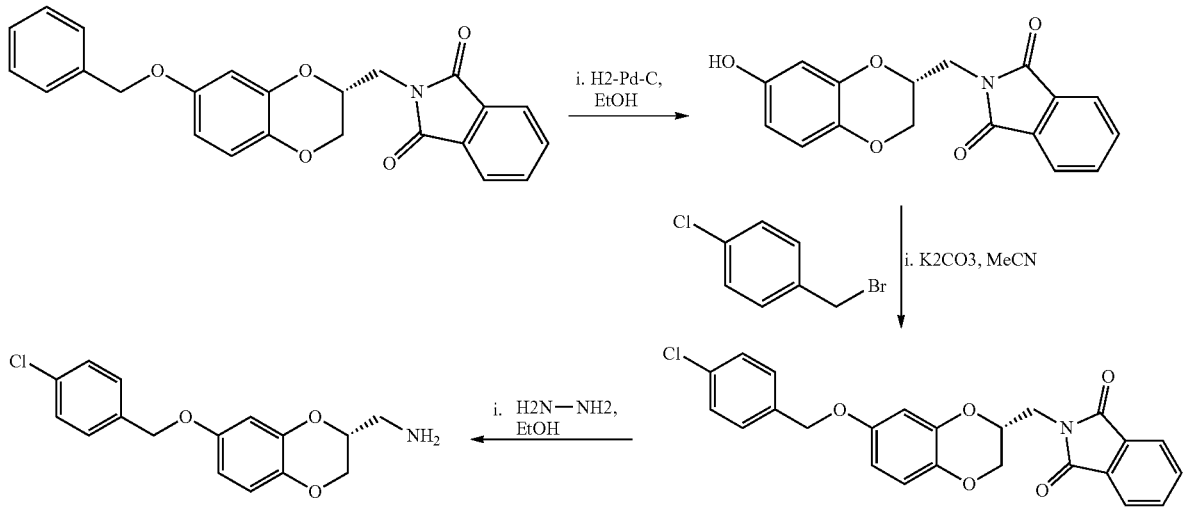

Synthesis of 2-((R)-7-Hydroxy-2,3-dihydro-benzo[1,4]dioxin-2-ylmethyl)-isoindole-1,3-dione A stirred mixture of 2-((R)-7-benzyloxy-2,3-dihydro-benzo[1,4]dioxin-2-ylmethyl)-isoindole-1,3-dione (1.50 g, 3.75 mmol, 1 eq) and 10% palladium on carbon (0.80 g, 0.75 mmol) in ethanol (80 mL) was placed under an atmosphere of hydrogen and allowed to stir at room temperature for 16 h. The reaction mixture was filtered through celite, washed with methanol and the filtrate concentrated under reduced pressure to give 2-((R)-7-hydroxy-2,3-dihydro-benzo[1,4]dioxin-2-ylmethyl)-isoindole-1,3-dione (1.03 g, 3.31 mmol, 89%) as an off-white solid.

AnalpH2_MeOH_4 min, Rt: 2.71 min; m/z 312.2 [M+H]$^+$
AnalpH9_MeOH_4 min, Rt: 2.71 min; m/z 312.2 [M+H]$^+$
$^1$H-NMR (400 MHz, DMSO-D6) δ 3.69-4.02 (m, 3H), 4.15-4.19 (m, 1H), 4.37-4.38 (m, 1H), 6.14-6.22 (m, 2H), 6.61 (d, J=8.7 Hz, 1H), 7.71-7.97 (m, 4H), 9.06 (br s, 1H)

Synthesis of 2-[(R)-7-(4-Chloro-benzyloxy)-2,3-dihydro-benzo[1,4]dioxin-2-ylmethyl]-isoindole-1,3-dione To a stirred mixture of 2-((R)-7-hydroxy-2,3-dihydro-benzo[1,4]dioxin-2-ylmethyl)-isoindole-1,3-dione (1.03 g, 3.31 mmol) and K$_2$CO$_3$ (0.46 g, 3.31 mmol) in anhydrous acetonitrile (20 mL) was added 4-chlorobenzyl bromide (0.61 g, 2.98 mmol). The resulting mixture was heated at 80° C. for 6 h. The reaction mixture was concentrated to approx. % of the volume and partitioned between ethyl acetate and water, the organic layer was separated and the aqueous layer extracted with ethyl acetate. The combined organic layers were washed with brine, dried (MgSO4) and concentrated under reduced pressure. The crude product was purified by column chromatography on silica eluting with 80-100% DCM/iso-hexane to afford 2-[(R)-7-(4-chloro-benzyloxy)-2,3-dihydro-benzo[1,4]dioxin-2-ylmethyl]-isoindole-1,3-dione (1.18 g, 2.72 mmol, 82%) as a white solid.

AnalpH2_MeOH_4 min, Rt: 3.65 min; m/z 436.1 [M+H]$^+$
$^1$H-NMR (400 MHz, CDCl3) δ 7.91-7.82 (m, 2H), 7.79-7.70 (m, 2H), 7.36-7.28 (4H), 6.82-6.72 (m, 1H), 6.51-6.39 (m, 2H), 4.91 (s, 2H), 4.56-4.43 (m, 1H), 4.24 (dd, J=11.8, 2.4 Hz, 1H), 4.07 (dd, J=14.2, 6.9 Hz, 1H), 3.98 (dd, J=11.4, 6.4 Hz, 1H), 3.88 (dd, J=14.2, 5.5 Hz, 1H)

Synthesis of C—[(R)-7-(4-Chloro-benzyloxy)-2,3-dihydro-benzo[1,4]dioxin-2-yl]-methylamine To a stirred mixture of 2-[(R)-7-(4-chloro-benzyloxy)-2,3-dihydro-benzo[1,4]dioxin-2-ylmethyl]-isoindole-1,3-dione (0.60 g, 1.38 mmol) in ethanol (14 mL) was added hydrazine monohydrate (0.67 mL, 13.8 mmol) and the resulting mixture heated at 80° C. for 1 h. The reaction mixture was diluted with 1M HCl solution, filtered and the filtrate concentrated under reduced pressure. The residue was dissolved in 1M NaOH solution and extracted with ethyl acetate. The combined organic layers were washed with brine, dried (MgSO4) and concentrated under reduced pressure to afford C—[(R)-7-(4-chloro-benzyloxy)-2,3-dihydro-benzo[1,4]dioxin-2-yl]-methylamine (0.37 g, 1.20 mmol, 87%) as a waxy solid.

AnalpH2_MeOH_4 min, Rt: 2.34 min; m/z 306.1 [M+H]$^+$
$^1$H-NMR (400 MHz, CDCl3) δ 7.26 (s, 4H), 6.70 (d, J=8.7 Hz, 1H), 6.47-6.33 (m, 2H), 4.14 (dd, J=11.0, 2.3 Hz, 1H), 4.08-4.00 (m, 1H), 3.88 (dd, J=11.0, 7.3 Hz, 1H), 2.97-2.81 (m, 2H), 1.40 (br s, 2H)

EXAMPLES

Example 1—Synthesis of 1-methyl-piperidine-4-carboxylic acid ((R)-7-benzyloxy-2,3-dihydro-benzo[1,4]dioxin-2-ylmethyl)-amide

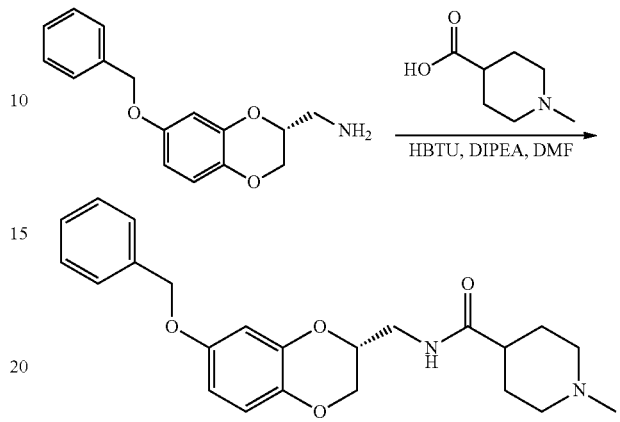

A mixture of 1-methylpiperidine-4-carboxylic acid (1.0 eq, 0.185 mmol), DIPEA (3.0 eq, 0.55 mmol) and HBTU (1.0 eq, 0.185 mmol) in anhydrous DMF (2 ml) and was stirred at room temperature for 20 min. ((R)-7-Benzyloxy-2,3-dihydro-benzo[1,4]dioxin-2-yl)-methylamine (1.0 eq, 0.185 mmol) was then added and the mixture stirred for 16 hr. The reaction was diluted with a mixture of water and aqueous sat. NaCl solution, and extracted with EtOAc. The organic phase was dried over MgSO$_4$, filtered and concentrated in vacuo to yield the crude material which was purified by preparative HPLC-MS to afford 1-methyl-piperidine-4-carboxylic acid ((R)-7-benzyloxy-2,3-dihydro-benzo[1,4]dioxin-2-ylmethyl)-amide (48.1 mg, 66%, white solid).

AnalpH2_MeOH_QC_V1, Rt: 5.63 min, m/z 397.3 [M+H]$^+$
AnalpH9_MeOH_QC_V1, Rt: 7.88 min, m/z 397.3 [M+H]$^+$
1H NMR (400 MHz, DMSO-d6): 8.00 (t, J=5.7 Hz, 1H), 7.40-7.24 (m, 5H), 6.73 (d, J=8.7 Hz, 1H), 6.49-6.42 (m, 2H), 4.97 (s, 2H), 4.16-4.07 (m, 2H), 3.81-3.74 (m, 1H), 3.38-3.17 (m, 2H), 2.75-2.67 (m, 2H) 2.08 (s, 3H) 2.09-1.99 (m, 1H) 1.80-1.71 (m, 2H) 1.64-1.43 (m, 4H)

General Scheme A—Amide Coupling Using HBTU

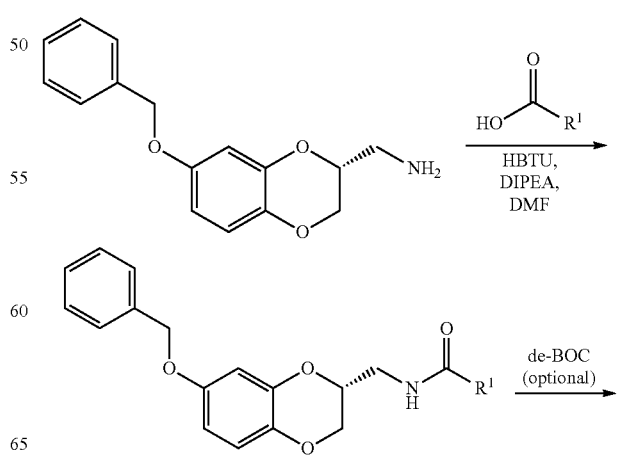

The following examples were prepared using analogous procedures (see General Method A):

| E.g. No. | Chemical Name | Structure | Analytical data | Mass, % yield, state |
|---|---|---|---|---|
| 2 | 5-(4-Methyl-piperazin-1-ylmethyl)-furan-2-carboxylic acid ((R)-7-benzyloxy-2,3-dihydro-benzo[1,4]dioxin-2-ylmethyl)-amide | Chiral | AnalpH2_MeOH_QC_V1, Rt: 5.92 min, m/z 478.3 [M + H]+ AnalpH9_MeOH_QC_V1, Rt: 8.21 min, m/z 478.3 [M + H]+ | 42.4 mg, 8%, off white solid |
| 3 | Oxazole-2-carboxylic acid ((R)-7-benzyloxy-2,3-dihydro-benzo[1,4]dioxin-2-ylmethyl)-amide | Chiral | AnalpH2_MeOH_QC_V1, Rt: 7.82 min, m/z 367.3 [M + H]+ AnalpH9_MeOH_QC_V1, Rt: 7.82 min, m/z 367.4 [M + H]+ | 26.7 mg, 28%, white solid |
| 4 | 5-(4-Methyl-piperazin-1-ylmethyl)-oxazole-2-carboxylic acid ((R)-7-benzyloxy-2,3-dihydro-benzo[1,4]dioxin-2-ylmethyl)-amide | Chiral | AnalpH2_MeOH_QC_V1, Rt: 5.87 min, m/z 479.33 [M + H]+ AnalpH9_MeOH_QC_V1, Rt: 8.02 min, m/z 479.33 [M + H]+ 1H NMR (400 MHz, DMSO-d6): 9.08 (t, J = 6.1 Hz, 1H), 7.43-7.27 (m, 6H), 6.79 (d, J = 8.8 Hz, 1H), 6.49-6.42 (m, 2H), 5.01 (s, 2H), 4.38-4.20 (m, 2H), 3.95-3.86 (m, 1H), 3.62 (s, 2H) 3.60-3.43 (m, 2H), 2.48-2.20 (m, 8H) 2.14 (s, 3H) | 39.4 mg, 46%, white solid |
| 5 | Tetrahydro-pyran-4-carboxylic acid ((R)-7-benzyloxy-2,3-dihydro-benzo[1,4]dioxin-2-ylmethyl)-amide | Chiral | AnalpH2_MeOH_QC_V1, Rt: 7.82 min, m/z 384.3 [M + H]+ AnalpH9_MeOH_QC_V1, Rt: 7.83 min, m/z 384.4 [M + H]+ | 33.0 mg, 48%, white solid |
| 6 | N-((R)-7-Benzyloxy-2,3-dihydro-benzo[1,4]dioxin-2-ylmethyl)-3-dimethylamino-propionamide | Chiral | AnalpH2_MeOH_QC_V1, Rt: 5.40 min, m/z 371.3 [M + H]+ AnalpH9_MeOH_QC_V1, Rt: 7.83 min, m/z 371.3 [M + H]+ | 24.0 mg, 36%, white solid |

| E.g. No. | Chemical Name | Structure | Analytical data | Mass, % yield, state |
|---|---|---|---|---|
| 7 | N-((R)-7-Benzyloxy-2,3-dihydro-benzo[1,4]dioxin-2-ylmethyl)-3-(4-methyl-piperazin-1-ylmethyl)-benzamide | Chiral | AnalpH2_MeOH_QC_V1, Rt: 5.97 min, m/z 487.6 [M + H]+ AnalpH9_MeOH_QC_V1, Rt: 8.22 min, m/z 487.6 [M + H]+ | 13.6 mg, 13%, white solid |
| 8 | N-((R)-7-Benzyloxy-2,3-dihydro-benzo[1,4]dioxin-2-ylmethyl)-2-(1-methyl-piperidin-4-yl)-acetamide | Chiral | AnalpH2_MeOH_QC_V1, Rt: 5.38 min, m/z 411.4 [M + H]+ AnalpH9_MeOH_QC_V1, Rt: 7.79 min, m/z 411.4 [M + H]+ | 43.5 mg, 59%, white solid |
| 9 | 4-{[((R)-7-Benzyloxy-2,3-dihydro-benzo[1,4]dioxin-2-ylmethyl)-carbamoyl]-methyl}-piperidine-1-carboxylic acid tert-butyl ester | Chiral | AnalpH2_MeOH_4 min_V1: Rt: 3.50 min, m/z 497.3 [M + H]+ | |
| 10 | N-((R)-7-Benzyloxy-2,3-dihydro-benzo[1,4]dioxin-2-ylmethyl)-2-pyridin-4-yl-acetamide | Chiral | AnalpH2_MeOH_QC_V1, Rt: 6.02 min, m/z 390.4 [M + H]+ AnalpH9_MeOH_QC_V1, Rt: 7.48 min, m/z 390.4 [M + H]+ | 38.0 mg, 66%, white solid |
| 11 | N-((R)-7-Benzyloxy-2,3-dihydro-benzo[1,4]dioxin-2-ylmethyl)-2-pyridin-3-yl-acetamide | Chiral | AnalpH2_MeOH_QC_V1, Rt: 6.44 min, m/z 391.2 [M + H]+ AnalpH9_MeOH_QC_V1, Rt: 7.52 min, m/z 391.2 [M + H]+ | 44.0 mg, 81%, white solid |
| 12 | N-((R)-7-Benzyloxy-2,3-dihydro-benzo[1,4]dioxin-2-ylmethyl)-2-(3,5-dimethyl-1H-pyrazol-4-yl)-acetamide | Chiral | AnalpH2_MeOH_QC_V1 Rt: 7.07 min, m/z 408.2 [M + H]+ AnalpH9_MeOH_QC_V1, Rt: 7.53 min, m/z 408.2 [M + H]+ | 37.0 mg, 64%, white solid |

| E.g. No. | Chemical Name | Structure | Analytical data | Mass, % yield, state |
|---|---|---|---|---|
| 13 | 4-[((R)-7-Benzyloxy-2,3-dihydro-benzo[1,4]dioxin-2-ylmethyl)-carbamoyl]-piperidine-1-carboxylic acid tert-butyl ester | Chiral | AnalpH2_MeOH_4 min_V1: Rt: 3.39 min, m/z 483.2 M + H]$^+$ solid | 85 mg, 80%, white |
| 14 | 1-Carbamoyl methyl-piperidine-4-carboxylic acid ((R)-7-benzyloxy-2,3-dihydro-benzo[1,4]dioxin-2-ylmethyl)-amide | Chiral | AnalpH2_MeOH_QC_Chiral V1, Rt: 5.44 min, m/z 440.2 [M + H]$^+$ AnalpH9_MeOH_QC_V1, Rt: 7.52 min, m/z 440.2 [M + H]$^+$ | 47.0 mg, 77%, white solid |
| 15 | 1-Furan-2-ylmethyl-piperidine-4-carboxylic acid ((R)-7-benzyloxy-2,3-dihydro-benzo[1,4]dioxin-2-ylmethyl)-amide | Chiral | AnalpH2_MeOH_QC_Chiral V1, Rt: 5.70 min, m/z 463.2 [M + H]$^+$ AnalpH9_MeOH_QC_V1, Rt: 8.13 min, m/z 463.2 [M + H]$^+$ 1H NMR (400 MHz, DMSO-d6): 7.99 (t, J = 5.7 Hz, 1H), 7.53 (s, 1H), 7.40-7.24 (m, 5H), 6.73 (d, J = 8.5 Hz, 1H), 6.49-6.42 (m, 2H), 6.36-6.33 (m, 1H), 6.21 (d, J = 3.5 Hz, 1H), 4.97 (s, 2H), 4.16-4.07 (m, 2H), 3.81-3.74 (m, 1H), 3.41 (s, 2H) 3.37-3.17 (m, 2H) 2.8-2.72 (m, 2H) 2.09-1.99 (m, 1H) 1.92-1.83 (m, 2H) 1.64-1.43 (m, 4H) | 35.0 mg, 53%, white solid |

The following compounds were made using General Method E:

| E.g. No. | Compound | | Analytical data | Mass, % yield, state |
|---|---|---|---|---|
| 16 | N-((R)-7-Benzyloxy-2,3-dihydro-benzo[1,4]dioxin-2-ylmethyl)-2-piperidin-4-yl-acetamide | Chiral | AnalpH2_MeOH_QC_V1, Rt: 5.41 min, m/z 397.3 [M + H]+ AnalpH9_MeOH_QC_V1, Rt: 7.47 min, m/z 397.3 [M + H]+ | 16 mg, 22%, white solid |

| E.g. No. | Compound | Analytical data | Mass, % yield, state |
|---|---|---|---|
| 17 | Piperidine-4-carboxylic acid ((R)-7-benzyloxy-2,3-dihydro-benzo[1,4]dioxin-2-ylmethyl)-amide 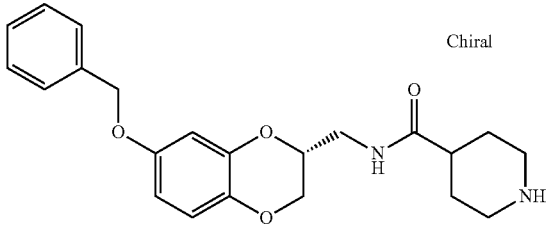 [SMILES: O=C(NC[C@@H]1COc2ccc(OCc3ccccc3)cc2O1)C1CCNCC1] Chiral | AnalpH2_MeOH_QC_V 1, Rt: 5.49 min, m/z 383.2 [M + H]+ AnalpH9_MeOH_QC_V 1, Rt: 7.38 min, m/z 383.2 [M + H]+ 1H NMR (400 MHz, CD2Cl2): 7.39-7.29 (m, 5H), 6.74 (d, J = 8.8 Hz, 1H), 6.49 (d, J = 3.2 Hz, 1H), 6.46 (dd, J = 3.2 Hz, J = 8.8 Hz, 1H), 5.85 (s, 1H), 4.95 (s, 2H), 4.23-4.16 (m, 2H), 3.85 (dd, J = 7.6 Hz, J = 12.0 Hz, 1H), 3.60-3.54 (m, 1H), 3.47-3.41 (m, 1H), 3.05 (d, J = 12.4 Hz, 2H), 2.58 (t, J = 12.4 Hz, 2H), 2.21-2.13 (m, 1H), 1.73 (d, J = 13.2 Hz, 2H), 1.54-1.45 (m, 2H) | 48 mg, 73%, pale brown solid |

General Scheme B - Mitsunobu Reaction

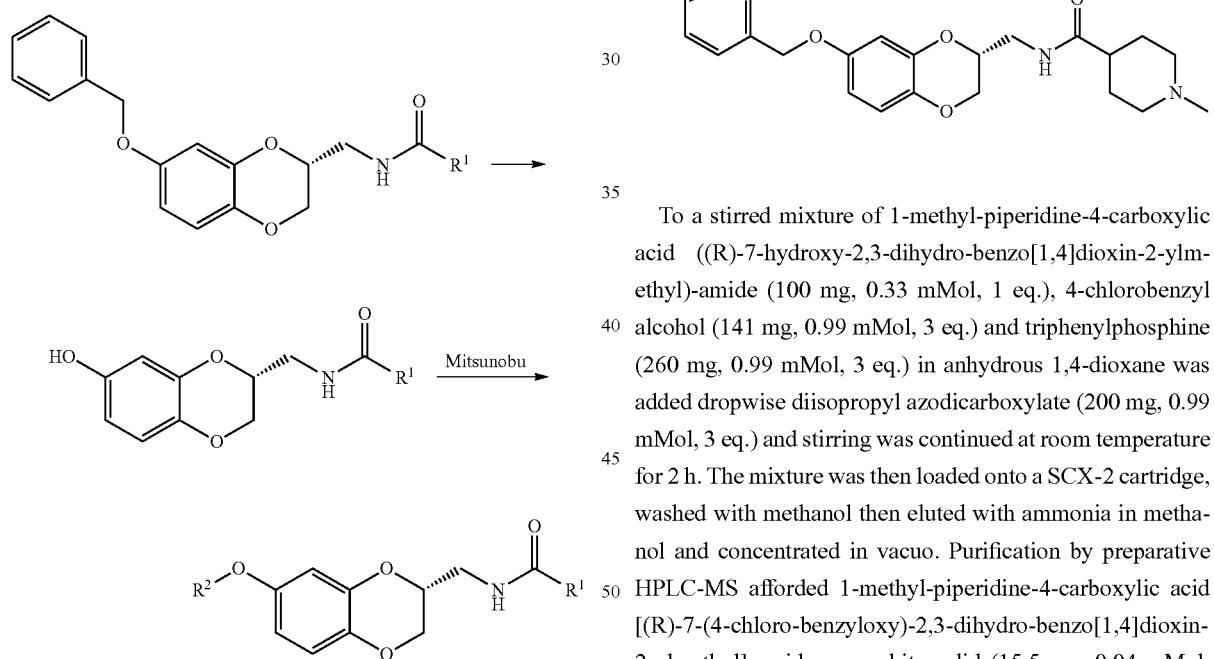

Example 18: Synthesis of 1-Methyl-piperidine-4-carboxylic acid [(R)-7-(4-chloro-benzyloxy)-2,3-dihydro-benzo[1,4]dioxin-2-ylmethyl]-amide

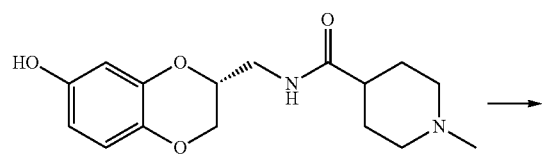

To a stirred mixture of 1-methyl-piperidine-4-carboxylic acid ((R)-7-hydroxy-2,3-dihydro-benzo[1,4]dioxin-2-ylmethyl)-amide (100 mg, 0.33 mMol, 1 eq.), 4-chlorobenzyl alcohol (141 mg, 0.99 mMol, 3 eq.) and triphenylphosphine (260 mg, 0.99 mMol, 3 eq.) in anhydrous 1,4-dioxane was added dropwise diisopropyl azodicarboxylate (200 mg, 0.99 mMol, 3 eq.) and stirring was continued at room temperature for 2 h. The mixture was then loaded onto a SCX-2 cartridge, washed with methanol then eluted with ammonia in methanol and concentrated in vacuo. Purification by preparative HPLC-MS afforded 1-methyl-piperidine-4-carboxylic acid [(R)-7-(4-chloro-benzyloxy)-2,3-dihydro-benzo[1,4]dioxin-2-ylmethyl]-amide as a white solid (15.5 mg, 0.04 mMol, 11%).

AnalpH2_MeOH_QC_V1, Rt: 5.99 min, m/z 431.2 [M+H]+

AnalpH9_MeOH_QC_V1, Rt: 8.06 min, m/z 431.2 [M+H]+

$^1$H NMR (400 MHz, DMSO-$d_6$): δ 1.39-1.67 (m, 4H), 1.71-1.78 (m, 2H), 1.92-2.16 (m, 4H), 2.69-2.72 (m, 2H), 3.18-3.24 (m, 1H), 3.31-3.37 (m, 1H), 3.75-3.80 (m, 1H), 4.09-4.15 (m, 2H), 4.97 (s, 2H), 6.42-6.47 (m, 2H), 6.73 (d, J=8.7 Hz, 1H), 7.31-7.48 (m, 4H), 8.00 (t, J=5.7 Hz, 1H)

The following compounds were made analogously using General Method B:

| E.g. No. | Chemical Name | Compound | Analytical data | Mass, % yield, state |
|---|---|---|---|---|
| 19 | Oxazole-2-carboxylic acid [(R)-7-(pyridin-3-ylmethoxy)-2,3-dihydro-benzo[1,4]dioxin-2-ylmethyl]-amide | Chiral | AnalpH2_MeOH_QC_V1, Rt: 5.33 min, m/z 368.26 [M + H]$^+$ AnalpH9_MeOH_QC_V1, Rt: 6.86 min, m/z 368.20 [M + H]$^+$ | 23.1 mg, 35%, white solid |
| 20 | Oxazole-2-carboxylic acid [(R)-7-(1H-pyrazol-4-ylmethoxy)-2,3-dihydro-benzo[1,4]dioxin-2-ylmethyl]-amide | Chiral | AnalpH2_MeOH_QC_V1, Rt: 6.23 min, m/z 307.23 [M + H]$^+$ AnalpH9_MeOH_QC_V1, Rt: 6.26 min, m/z 357.23 [M + H]$^+$ | 22.0 mg, 34%, white solid |
| 21 | Oxazole-2-carboxylic acid [(R)-7-(1-methyl-piperidin-4-ylmethoxy)-2,3-dihydro-benzo[1,4]dioxin-2-ylmethyl]-amide | Chiral | AnalpH2_MeOH_QC_V1, Rt: 4.28 min, m/z 388.32 [M + H]$^+$ AnalpH9_MeOH_QC_V1, Rt: 7.06 min, m/z 388.32 [M + H]$^+$ | 9.9 mg, 13%, white solid |
| 22 | 5-(4-Methyl-piperazin-1-ylmethyl)-furan-2-carboxylic acid [(R)-7-(4-methoxy-benzyloxy)-2,3-dihydro-benzo[1,4]dioxin-2-ylmethyl]-amide | Chiral | AnalpH2_MeOH_QC_V1, Rt: 5.91 min, m/z 508.36 [M + H]$^+$ AnalpH9_MeOH_QC_V1, Rt: 8.12 min, m/z 508.36 [M + H]$^+$ | 17.6 mg, 17%, off white solid |
| 23 | 5-(4-Methyl-piperazin-1-ylmethyl)-furan-2-carboxylic acid ((R)-7-phenethyloxy-2,3-dihydro-benzo[1,4]dioxin-2-ylmethyl)-amide | Chiral | AnalpH2_MeOH_QC_V1, Rt: 6.21 min, m/z 492.36 [M + H]$^+$ AnalpH9_MeOH_QC_V1, Rt: 8.40 min, m/z 492.36 [M + H]$^+$ | 30.0 mg, 29%, white solid |
| 24 | 5-(4-Methyl-piperazin-1-ylmethyl)-furan-2-carboxylic acid [(R)-7-(4-chloro-benzyloxy)-2,3-dihydro-benzo[1,4]dioxin-2-ylmethyl]-amide | Chiral | AnalpH2_MeOH_QC_V1, Rt: 6.35 min, m/z 512.36 [M + H]$^+$ AnalpH9_MeOH_QC_V1, Rt: 8.49 min, m/z 512.36 [M + H]$^+$ | 52.5 mg, 49%, white solid |

| E.g. No. | Chemical Name | Compound | Analytical data | Mass, % yield, state |
|---|---|---|---|---|
| 25 | 5-(4-Methyl-piperazin-1-ylmethyl)-furan-2-carboxylic acid [(R)-7-(5-chloro-pyridin-3-ylmethoxy)-2,3-dihydro-benzo[1,4]dioxin-2-ylmethyl]-amide | Chiral | AnalpH2_MeOH_QC_V1, Rt: 5.68 min, m/z 513.33 [M + H]$^+$ AnalpH9_MeOH_QC_V1, Rt: 7.92 min, m/z 513.26 [M + H]$^+$ | 17.8 mg, 16%, white solid |
| 26 | 5-(4-Methyl-piperazin-1-ylmethyl)-furan-2-carboxylic acid [(R)-7-(5-chloro-pyridin-2-ylmethoxy)-2,3-dihydro-benzo[1,4]dioxin-2-ylmethyl]-amide | Chiral | AnalpH2_MeOH_QC_V1, Rt: 5.61 min, m/z 513.20 [M + H]$^+$ AnalpH9_MeOH_QC_V1, Rt: 7.86 min, m/z 513.20 [M + H]$^+$ | 14.2 mg, 13%, white solid |
| 27 | 1-Methyl-piperidine-4-carboxylic acid [(R)-7-(3,4-difluoro-benzyloxy)-2,3-dihydro-benzo[1,4]dioxin-2-ylmethyl]-amide | Chiral | AnalpH2_MeOH_QC_V1, Rt: 5.78 min, m/z 433.2 [M + H]$^+$ AnalpH9_MeOH_QC_V1, Rt: 7.82 min, m/z 433.2 [M + H]$^+$ | 4.27 mg, 3% white solid |
| 28 | 1-Methyl-piperidine-4-carboxylic acid [(R)-7-(3-methyl-benzyloxy)-2,3-dihydro-benzo[1,4]dioxin-2-ylmethyl]-amide | Chiral | AnalpH2_MeOH_QC_V1, Rt: 5.93 min, m/z 411.2 [M + H]$^+$ AnalpH9_MeOH_QC_V1, Rt: 7.93 min, m/z 411.2 [M + H]$^+$ $^1$H NMR (400 MHz, CDCl$_3$): δ 1.64-2.21 (m, 7H), 2.22-2.52 (m, 3H), 2.91 (d, J = 10.5 Hz, 2H), 3.37-3.56 (m, 1H), 3.60-3.66 (m, 1H), 3.80-3.85 (m, 1H), 4.10-4.38 (m, 2H), 4.90 (s, 2H), 5.88 (br s, 1H), 6.37-6.60 (m, 2H), 6.73 (d, J = 8.7 Hz, 1H), 7.00-7.35 (m, 4H) | 21.4 mg, 16%, white solid |
| 29 | 1-Methyl-piperidine-4-carboxylic acid [(R)-7-(4-methyl-benzyloxy)-2,3-dihydro-benzo[1,4]dioxin-2-ylmethyl]-amide | Chiral | AnalpH2_MeOH_QC_V1, Rt: 5.92 min, m/z 411.3 [M + H]$^+$ AnalpH9_MeOH_QC_V1, Rt: 7.92 min, m/z 411.2 [M + H]$^+$ $^1$H NMR (400 MHz, CDCl$_3$) δ 1.71-2.26 (m, 4H), 2.30-2.53 (m, 5H), 2.99 (br s, 2H), 3.36-3.51 (m, 2H), 3.59-3.66 (m, 1H), 3.82 (dd, J = 11.4, 7.3 Hz, 1H), 4.12-4.27 (m, 2H), 4.90 (s, 2H), 5.92 (s, 1H), 6.42-6.52 (m, 2H), 6.69-6.77 (m, 1H), 7.14 (d, J = 8.9 Hz, 2H), 7.25 (d, J = 8.2 Hz, 2H) | 9.3 mg, 7%, white solid |

| E.g. No. | Chemical Name | Compound | | Analytical data | Mass, % yield, state |
|---|---|---|---|---|---|
| 30 | 1-Methyl-piperidine-4-carboxylic acid [(R)-7-(3-chloro-benzyloxy)-2,3-dihydro-benzo[1,4]dioxin-2-ylmethyl]-amide | | Chiral | AnalpH2_MeOH_QC_V1, Rt: 6.01 min, m/z 431.2 [M + H]⁺ AnalpH9_MeOH_QC_V1, Rt: 8.01 min, m/z 431.1 [M + H]⁺ 1H-NMR (400 MHz, CDCl₃) δ 1.59-2.53 (m, 9H), 2.96 (s, 2H), 3.36-3.50 (m, 2H), 3.60-3.66 (m, 1H), 3.82 (dd, J = 11.3, 7.4 Hz, 1H), 4.08-4.31 (m, 2H), 4.91 (s, 2H), 5.89 (s, 1H), 6.38-6.47 (m, 2H), 6.73 (d, J = 8.2 Hz, 1H), 7.22-7.30 (m, 3H), 7.36 (s, 1H) | 24.4 mg, 17%, white solid |
| 31 | 1-Methyl-piperidine-4-carboxylic acid [(R)-7-(4-fluoro-benzyloxy)-2,3-dihydro-benzo[1,4]dioxin-2-ylmethyl]-amide | | Chiral | AnalpH2_MeOH_QC_V1, Rt: 5.60 min, m/z 415.2 [M + H]⁺ AnalpH9_MeOH_QC_V1, Rt: 7.72 min, m/z 415.2 [M + H]⁺ | 17.7 mg, 13%, white solid |
| 32 | 1-Methyl-piperidine-4-carboxylic acid [(R)-7-(2-methyl-benzyloxy)-2,3-dihydro-benzo[1,4]dioxin-2-ylmethyl]-amide | | Chiral | AnalpH2_MeOH_QC_V1, Rt: 5.88 min, m/z 411.3 [M + H]⁺ AnalpH9_MeOH_QC_V1, Rt: 7.93 min, m/z 411.2 [M + H]⁺ | 22.2 mg, 16%, white solid |

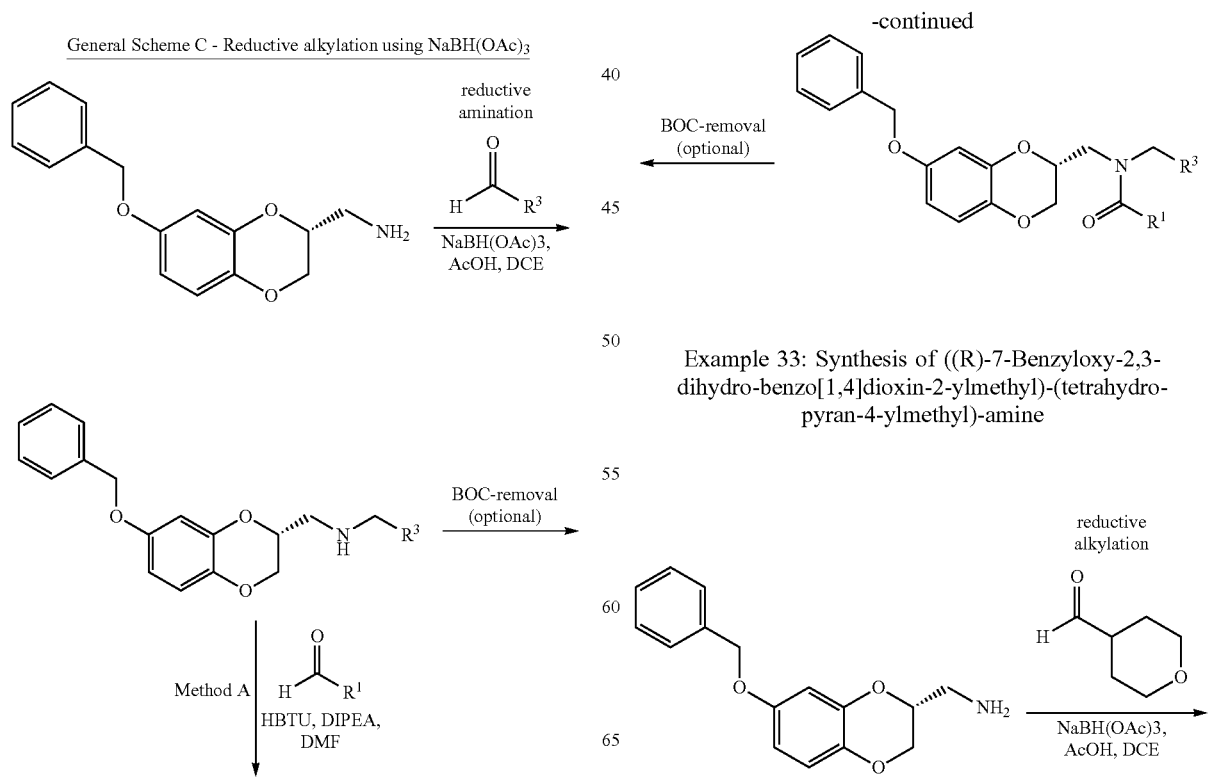

Example 33: Synthesis of ((R)-7-Benzyloxy-2,3-dihydro-benzo[1,4]dioxin-2-ylmethyl)-(tetrahydro-pyran-4-ylmethyl)-amine -continued

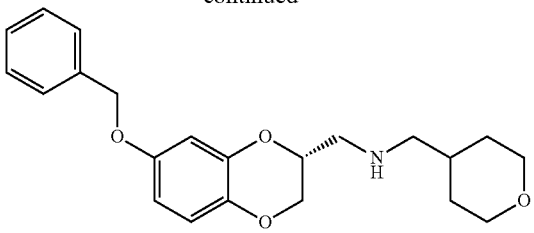

To a solution of tetrahydro-2H-pyran-4-carbaldehyde (1.3 eq, 0.23 mmol) in anhydrous DCM (2 ml) at RT was added ((R)-7-benzyloxy-2,3-dihydro-benzo[1,4]dioxin-2-yl)-methylamine (1 eq, 0.18 mmol), then AcOH (1.3 eq, 0.23 mmol) and the mixture was stirred at RT for 2 h. Then NaBH(OAc)$_3$ (1.3 eq, 0.23) was added and stirred at RT for 16 h, then the volatiles were removed in vacuo. The residue was taken up in DCM and the organic solution washed with NaHCO$_3$(aq) solution, passed through a hydrophobic frit and concentrated under reduced pressure. The crude material was purified by reverse phase prep HPLC to give ((R)-7-benzyloxy-2,3-dihydro-benzo[1,4]dioxin-2-ylmethyl)-(tetrahydro-pyran-4-ylmethyl)-amine (34.5, 52%) as a white solid.

Anal pH2MeOH_QC_V1: Rt: 5.37 min, m/z 369.5 [M+H]$^+$

AnalpH9MeOH_QC_V1: Rt: 8.21 min, m/z 369.5 [M+H]$^+$ $^1$H NMR (400 MHz, DMSO): 7.40-7.24 (m, 5H) 6.74-6.69 (d, J=8.3 Hz, 1H) 6.50-6.40 (m, 2H) 4.96 (s, 2H) 4.25-4.09 (m, 2H) 3.89-3.75 (3H) 3.26-3.17 (m, 2H) 2.76-2.61 (m, 2H) 2.41-2.35 (m, 2H) 1.76 (s, 1H) 1.60-1.50 (m, 3H) 1.14-1.00 (m, 2H)

The following compounds were made analogously using General Method C:

| E.g. No. | Chemical Name | Compound | | Analytical data | Mass, % yield, state |
|---|---|---|---|---|---|
| 34 | 1-{4-[((R)-7-Benzyloxy-2,3-dihydro-benzo[1,4]dioxin-2-ylmethyl)-amino]-piperidin-1-yl}-ethanone | Chiral | | AnalpH2_MeOH_QC_V1: Rt: 5.23 min, m/z 397.2 [M + H]$^+$ AnalpH9_MeOH_QC_V1: Rt: 7.78 min, m/z 397.2 [M + H]$^+$ | 21 mg, 36%, white solid |
| 35 | [3-(4-{[((R)-7-Benzyloxy-2,3-dihydro-benzo[1,4]dioxin-2-ylmethyl)-amino]-methyl}-phenoxy)-propyl]-dimethyl-amine | | Chiral | AnalpH2_MeOH_4 min: Rt: 1.69 min, m/z 463 [M + H]$^+$ | 100 mg, quant., yellow oil |
| 36 | (4-{[((R)-7-Benzyloxy-2,3-dihydro-benzo[1,4]dioxin-2-ylmethyl)-amino]-methyl}-benzyl)-carbamic acid tert-butyl ester | | Chiral | AnalpH2_MeOH_4 min: Rt: 2.64 min, m/z 491 [M + H]$^+$ | 120 mg, quant., colourless oil |
| 37 | ((R)-7-Benzyloxy-2,3-dihydro-benzo[1,4]dioxin-2-ylmethyl)-(1-benzyl-piperidin-4-ylmethyl)-amine | | Chiral | AnalpH2_MeOH_4 min: Rt: 1.77 min, m/z 459 [M + H]$^+$ | 145 mg, quant., |

| E.g. No. | Chemical Name | Compound | Analytical data | Mass, % yield, state |
|---|---|---|---|---|
| 38 | ((R)-7-Benzyloxy-2,3-dihydro-benzo[1,4]diox-in-2-ylmethyl)-(1-benzyl-piperidin-4-yl)-amine | Chiral | AnalpH2_MeOH_4 min: Rt: 1.80 min, m/z 445 [M + H]$^+$ | 125 mg, quant., yellow oil |
| 39 | 4-[((R)-7-Benzyloxy-2,3-dihydro-benzo[1,4]diox-in-2-ylmethyl)-amino]-piperidine-1-carboxylic acid tert-butyl ester | Chiral | AnalpH2_MeOH_4 min: Rt: 2.45 min, m/z 454.9 [M + H]$^+$ | 100 mg, quant., clear oil |

The following compounds were subsequently prepared using General Method A:

| E.g. No. | Chemical Name | Compound | Analytical data | Mass, % yield, state |
|---|---|---|---|---|
| 40 | Oxazole-2-carboxylic acid ((R)-7-benzyloxy-2,3-dihydro-benzo[1,4]dioxin-2-ylmethyl)-[4-(3-dimethylamino-propoxy)-benzyl]-amide | Chiral | AnalpH2_MeOH_QC_V1: Rt: 6.26 min, m/z 558.29 [M + H]$^+$ AnalpH9_MeOH_QC_V1: Rt: 8.59 min, m/z 558.29 [M + H]$^+$ | 19.4 mg, 19%, yellow gum |
| 41 | (4-{[((R)-7-Benzyloxy-2,3-dihydro-benzo[1,4]dioxin-2-ylmethyl)-(oxazole-2-carbonyl)-amino]-methyl}-benzyl)-carbamic acid tert-butyl ester | Chiral | AnalpH2_MeOH_QC_V1: Rt: 8.51 min, m/z 586.4 [M + H]$^+$ AnalpH9_MeOH_QC_V1: Rt: 8.53 min, m/z 586.2 [M + H]$^+$ | 17 mg, 16%, white solid |

| E.g. No. | Chemical Name | Compound | Analytical data | Mass, % yield, state |
|---|---|---|---|---|
| 42 | Oxazole-2-carboxylic acid ((R)-7-benzyloxy-2,3-dihydro-benzo[1,4]dioxin-2-ylmethyl)-(1-benzyl-piperidin-4-ylmethyl)-amide | Chiral | AnalpH2_MeOH_QC_V1: Rt: 6.23 min, m/z 554.35 [M + H]$^+$ AnalpH9_MeOH_QC_V1: Rt: 8.81 min, m/z 554.35 [M + H]$^+$ | 23.2 mg, 23%, white solid |
| 43 | Oxazole-2-carboxylic acid ((R)-7-benzyloxy-2,3-dihydro-benzo[1,4]dioxin-2-ylmethyl)-(1-benzyl-piperidin-4-yl)-amide | Chiral | AnalpH2_MeOH_QC_V1: Rt: 6.28 min, m/z 540.35 [M + H]$^+$ AnalpH9_MeOH_QC_V1: Rt: 8.87 min, m/z 540.35 [M + H]$^+$ | 10.7 mg, 11%, white solid |

45

The following compounds were subsequently prepared using General Method E:

| E.g. No. | Chemical Name | Compound | Analytical data | Mass, % yield, state |
|---|---|---|---|---|
| 44 | Oxazole-2-carboxylic acid (4-aminomethyl-benzyl)-((R)-7-benzyloxy-2,3-dihydro-benzo[1,4]dioxin-2-ylmethyl)-amide | Chiral | AnalpH2_MeOH_QC_V1: Rt: 6.11 min, m/z 486.3 [M + H]$^+$ AnalpH9_MeOH_QC_V1: Rt: 7.83 min, m/z 486.3 [M + H]$^+$ | 30 mg, 55%, white solid |

| E.g. No. | Chemical Name | Compound | Analytical data | Mass, % yield, state |
|---|---|---|---|---|
| 45 | ((R)-7-Benzyloxy-2,3-dihydro-benzo[1,4]dioxin-2-ylmethyl)-piperidin-4-yl-amine | Chiral | AnalpH2_MeOH_QC_V1: Rt: 3.69 min, m/z 355.2 [M + H]$^+$ AnalpH9_MeOH_QC_V1: Rt: 7.67 min, m/z 355.2 [M + H]$^+$ 1H NMR (400 MHz, CD2Cl2): 7.39-7.14 (m, 5H), 6.73 (d, J = 8.4 Hz, 1H), 6.48 (d, J = 2.4 Hz, 1H), 6.44 (dd, J = 1.6 Hz, J = 2.8 Hz, 1H), 4.94 (s, 2H), 4.18-4.17 (m, 2H), 3.95-3.92 (m, 1H), 3.01 (d, J = 20.4 Hz, 2H), 2.89-2.79 (m, 2H), 2.55-2.45 (m, 3H), 1.82 (d, J = 10.8 Hz, 2H), 1.17-1.08 (m, 2H) | 42 mg, 49%, white solid |

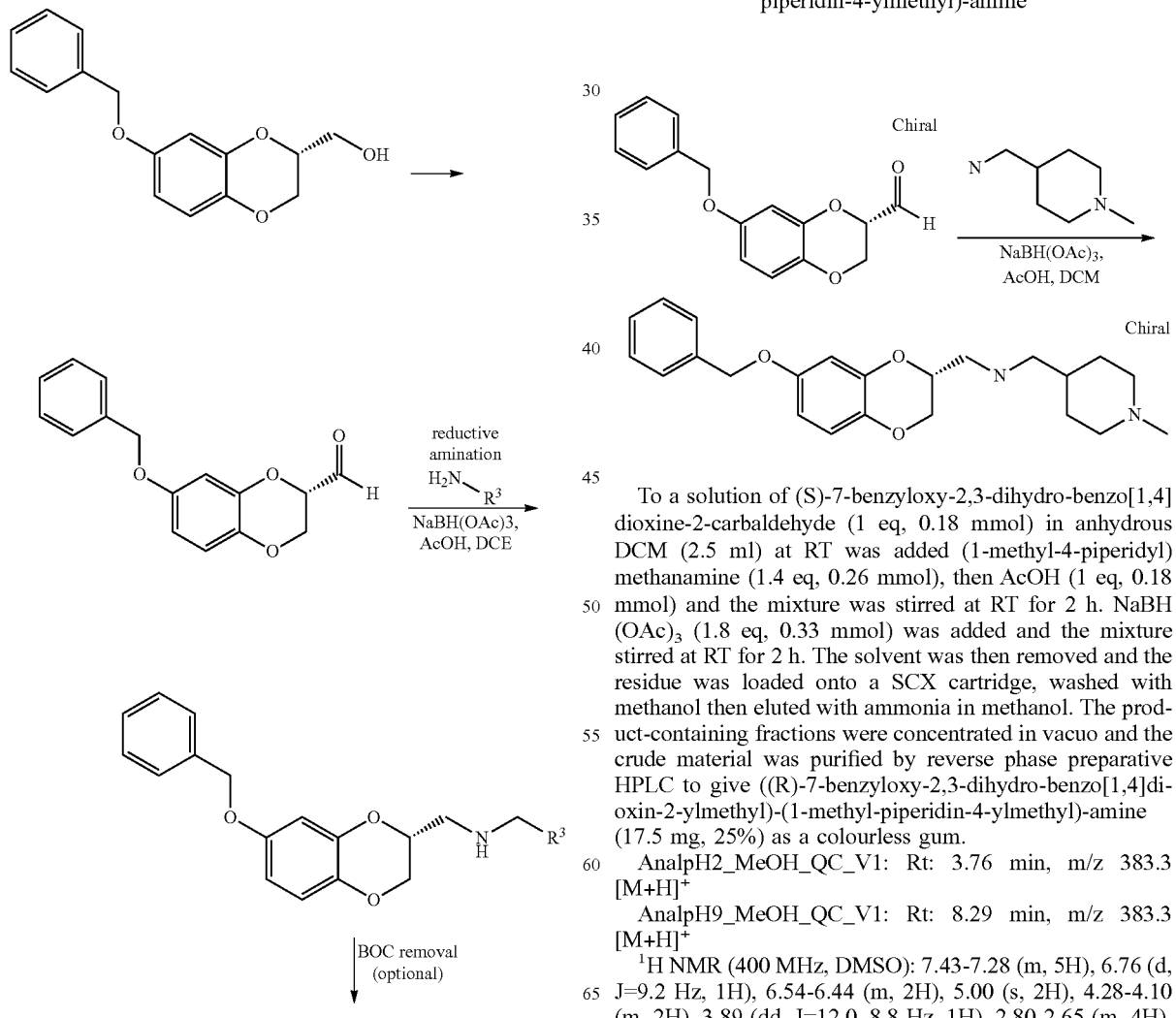

Example 46: Synthesis of ((R)-7-Benzyloxy-2,3-dihydro-benzo[1,4]dioxin-2-ylmethyl)-(1-methyl-piperidin-4-ylmethyl)-amine To a solution of (S)-7-benzyloxy-2,3-dihydro-benzo[1,4]dioxine-2-carbaldehyde (1 eq, 0.18 mmol) in anhydrous DCM (2.5 ml) at RT was added (1-methyl-4-piperidyl)methanamine (1.4 eq, 0.26 mmol), then AcOH (1 eq, 0.18 mmol) and the mixture was stirred at RT for 2 h. NaBH(OAc)$_3$ (1.8 eq, 0.33 mmol) was added and the mixture stirred at RT for 2 h. The solvent was then removed and the residue was loaded onto a SCX cartridge, washed with methanol then eluted with ammonia in methanol. The product-containing fractions were concentrated in vacuo and the crude material was purified by reverse phase preparative HPLC to give ((R)-7-benzyloxy-2,3-dihydro-benzo[1,4]dioxin-2-ylmethyl)-(1-methyl-piperidin-4-ylmethyl)-amine (17.5 mg, 25%) as a colourless gum.

AnalpH2_MeOH_QC_V1: Rt: 3.76 min, m/z 383.3 [M+H]$^+$
AnalpH9_MeOH_QC_V1: Rt: 8.29 min, m/z 383.3 [M+H]$^+$
$^1$H NMR (400 MHz, DMSO): 7.43-7.28 (m, 5H), 6.76 (d, J=9.2 Hz, 1H), 6.54-6.44 (m, 2H), 5.00 (s, 2H), 4.28-4.10 (m, 2H), 3.89 (dd, J=12.0, 8.8 Hz, 1H), 2.80-2.65 (m, 4H), 2.40 (d, J=6.6 Hz, 2H), 2.12 (s, 3H), 1.82-1.72 (m, 2H), 1.68-1.60 (m, 2H), 1.56-1.45 (m, 1H) 1.37-1.23 (m, 1H), 1.16-1.03 (m, 2H).

The following compounds were made analogously using General Method D:

| E.g. No. | Chemical Name | Compound | Analytical data | Mass, % yield, state |
|---|---|---|---|---|
| 47 | 1-{2-[((R)-7-Benzyloxy-2,3-dihydro-benzo[1,4]dioxin-2-ylmethyl)-amino]-2-phenyl-ethyl}-pyrrolidin-2-one | Chiral | $^1$H NMR (400 MHz, DMSO) 7.43-7.22 (m, 10H) 6.74 (d, J = 8.7 Hz, 1H) 6.51-6.43 (m, 2H) 5.00 (s, 2H) 4.26-4.06 (m, 2H) 3.91-3.80 (m, 2H) 3.53-3.44 (m, 1H) 3.32-3.24 (m, 1H) 3.18-3.02 (m, 2H) 2.64-2.52 (m, 2H) 2.48-2.24 (m, 2H) 2.20-2.09 (m, 2H) 1.85-1.74 (m, 2H) AnalpH2_MeOH_QC_V1: Rt: 6.33 min, m/z 459.3 [M + H]$^+$ AnalpH9_MeOH_QC_V1: Rt: 8.47 min, m/z 459.3 [M + H]$^+$ | 15 mg, 17%, brown oil |
| 48 | ((R)-7-Benzyloxy-2,3-dihydro-benzo[1,4]dioxin-2-ylmethyl)-indan-1-yl-amine | Chiral | AnalpH2_MeOH_QC_V1: Rt: 6.20 min, m/z 388.3 [M + H]$^+$ AnalpH9_MeOH_QC_V1: Rt: 8.89 min, m/z 388.3 [M + H]$^+$ | 12.5 mg, 17%, white gum |
| 49 | 2-[((R)-7-Benzyloxy-2,3-dihydro-benzo[1,4]dioxin-2-ylmethyl)-amino]-N-methyl-2-phenyl-acetamide | Chiral | AnalpH2_MeOH_QC_V1: Rt: 6.16 min, m/z 419.3 [M + H]$^+$ AnalpH9_MeOH_QC_V1: Rt: 8.13 min, m/z 419.3 [M + H]$^+$ | 6.6 mg, 6%, white solid |
| 50 | N-{4-[((R)-7-Benzyloxy-2,3-dihydro-benzo[1,4]dioxin-2-ylmethyl)-amino]-cyclohexyl}-2-dimethyl-amino-acetamide | Chiral | AnalpH2_MeOH_QC_V1: Rt: 4.07 min, m/z 454.4 [M + H]$^+$ AnalpH9_MeOH_QC_V1: Rt: 8.25 min, m/z 454.4 [M + H]$^+$ | 12.3 mg, 5.3%, colourless gum |

-continued

| E.g. No. | Chemical Name | Compound | Analytical data | Mass, % yield, state |
|---|---|---|---|---|
| 51 | N-{4-[((R)-7-Benzyloxy-2,3-dihydro-benzo[1,4]dioxin-2-ylmethyl)-(2H-pyrazol-3-ylmethyl)-amino]-cyclohexyl}-2-dimethyl-amino-acetamide | Chiral | AnalpH2_MeOH_QC_V1: Rt: 4.26 min, m/z 534.4 [M + H]+ AnalpH9_MeOH_QC_V1: Rt: 8.33 min, m/z 534.4 [M + H]+ | 31.4 mg, 37%, white solid |
| 52 | 1-{2-[4-((R)-7-Benzyloxy-2,3-dihydro-benzo[1,4]dioxin-2-ylmethyl)-piperazin-1-yl]-ethyl}-1H-pyridin-2-one | Chiral | AnalpH2_MeOH_QC_V1: Rt: 5.61 min, m/z 462.3 [M + H]+ AnalpH9_MeOH_QC_V1: Rt: 8.08 min, m/z 462.3 [M + H]+ $^1$H NMR (400 MHz, DMSO): 7.60-7.55 (m, 1H) 7.40-7.23 (m, 6H) 6.72 (d, J = 8.7 Hz, 1H) 6.49 (d, J = 2.7 Hz, 1H) 6.43 (dd, J = 8.7, 3.2 Hz, 1H) 6.31 (d, J = 9.2 Hz, 1H) 6.14 (dt, J = 6.8, 1.3 Hz, 1H) 4.96 (s, 2H) 4.30-4.21 (m, 1H) 4.20-4.13 (m, 1H) 3.92 (t, J = 6.3 Hz, 2H) 3.83 (dd, J = 11.4, 6.7 Hz, 1H) 2.52-2.45 (m, 4H) 2.45-2.20 (m, 8H) | 69 mg, 50%, brown gum |
| 53 | ((R)-7-Benzyloxy-2,3-dihydro-benzo[1,4]dioxin-2-ylmethyl)-[3-(4-methyl-piperazin-1-yl)-benzyl]-amine | Chiral | AnalpH2_MeOH_QC_V1: Rt: 4.25 min, m/z 460.3 [M + H]+ AnalpH9_MeOH_QC_V1: Rt: 8.58 min, m/z 460.3 [M + H]+ | 4.6 mg, 2.1%, brown gum |
| 54 | 3-{[((R)-7-Benzyloxy-2,3-dihydro-benzo[1,4]dioxin-2-ylmethyl)-amino]-methyl}-morpholine-4-carboxylic acid tert-butyl ester | Chiral | AnalpH2_MeOH_4min_V1: Rt: 2.48 min, m/z 471.3 [M + H]+ | 278 mg, 53%, brown oil |

| E.g. No. | Chemical Name | Compound | Analytical data | Mass, % yield, state |
|---|---|---|---|---|
| 55 | 5-{[((R)-7-Benzyloxy-2,3-dihydro-benzo[1,4]dioxin-2-ylmethyl)-amino]-methyl}-piperidin-2-one | Chiral | AnalpH2_MeOH_QC_V1: Rt: 5.14 min, m/z 383.2 [M + H]+ AnalpH9_MeOH_QC_V1: Rt: 7.71 min, m/z 383.2 [M + H]+ | 9 mg, 13%, white solid |
| 56 | 3-{[((R)-7-Benzyloxy-2,3-dihydro-benzo[1,4]dioxin-2-ylmethyl)-amino]-methyl}-piperidine-1-carboxylic acid tert-butyl ester | Chiral | AnalpH2_MeOH_4min_V1: Rt: 2.48 min, m/z 471.3 [M + H]+ | 32 mg, 23%, brown oil |

The following compounds were subsequently made using General Method E:

| E.g. No. | Chemical Name | Compound | Analytical data | Mass, % yield, state |
|---|---|---|---|---|
| 57 | ((R)-7-Benzyloxy-2,3-dihydro-benzo[1,4]dioxin-2-ylmethyl)-morpholin-3-ylmethyl-amine | Chiral | AnalpH2_MeOH_QC_V1: Rt: 4.71 min, m/z 371.2 [M + H]+ AnalpH9_MeOH_QC_V1: Rt: 7.63 min, m/z 371.2 [M + H]+ 1H NMR (400 MHz, CD$_2$Cl$_2$): 7.39-7.27 (m, 5H), 6.73 (d, J = 8.8 Hz, 1H), 6.48 (bs, 1H), 6.45 (d, J = 8.8 Hz, 1H), 4.94 (s, 2H), 4.19 (d, J = 10.0 Hz, 2H), 3.96 (dd, J = 8.8 Hz, J = 18.0 Hz, 1H), 3.71 (d, J = 11.2 Hz, 2H), 3.45 (t, J = 9.6 Hz, 1H), 3.17 (t, J = 10.0 Hz, 1H), 2.88 (m, 5H), 2.59 (d, J = 11.6 Hz, 1H), 2.48 (t, J = 11.2 Hz, 1H) | 28 mg, 59%, brown gum |
| 58 | ((R)-7-Benzyloxy-2,3-dihydro-benzo[1,4]dioxin-2-ylmethyl)-piperidin-3-ylmethyl-amine | Chiral | AnalpH2_MeOH_QC_V1: Rt: 3.87 min, m/z 369.2 [M + H]+ AnalpH9_MeOH_QC_V1: Rt: 7.10 min, m/z 369.2 [M + H]+ | 6 mg, 24%, brown gum |

General Scheme E

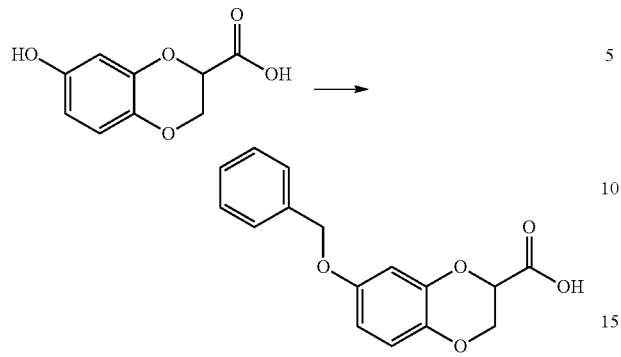

Example 59 Synthesis of 4-(4-{[(7-benzyloxy-2,3-dihydro-benzo[1,4]dioxine-2-carbonyl)-amino]-methyl}-benzyl)-piperazine-1-carboxylic acid tert-butylester

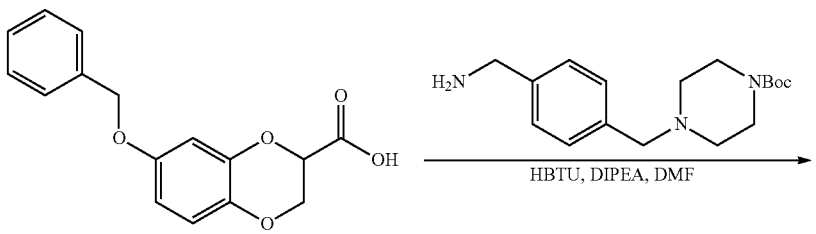

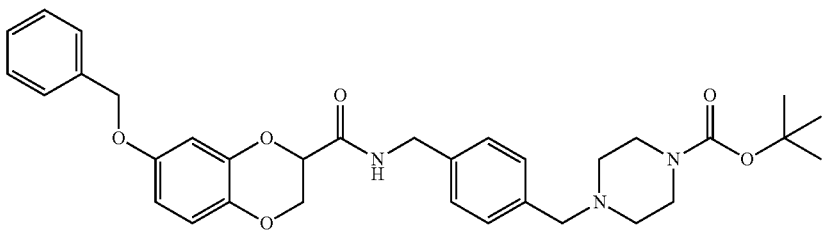

To a solution of 6-benzyloxy-2,3-dihydro-1,4-benzodioxine-3-carboxylic acid (80 mg, 0.27 mmol, 1 eq), 4-(4-aminomethyl-benzyl)-piperazine-1-carboxylic acid tert-butyl ester (100 mg, 0.33 mmol, 1.2 eq) and HBTU (127 mg, 0.33 mmol, 1.2 eq) in anhydrous DMF (3 mL) was added N,N-diisopropylethylamine (141 uL, 0.81 mmol, 3.0 eq) and the reaction was stirred at RT for 4 h. The reaction mixture was then extracted with EtOAc, and the organic extract washed with water, brine, dried over magnesium sulphate, and concentrated in vacuo. The crude material was partially-purified by column chromatography to give a crude sample (123 mg) of the title compound as a brown oil. 43 mg of this crude sample was further purified by preparative HPLC to give 4-(4-{[(7-benzyloxy-2,3-dihydro-benzo[1,4]dioxine-2-carbonyl)-amino]-methyl}-benzyl)-piperazine-1-carboxylic acid tert-butyl ester (10 mg, 20%) as a white solid.

AnalpH2_MeOH_QC_V1: Rt: 6.27 min, m/z 574.4 [M+H]$^+$

AnalpH9_MeOH_QC_V1: Rt: 8.43 min, m/z 574.3 [M+H]$^+$

The following compounds were made analogously using General Method A:

| E.g. No. | Chemical Name | Compound | Analytical data | Mass, % yield, state |
|---|---|---|---|---|
| 59 | 7-Benzyloxy-2,3-dihydro-benzo[1,4]diox-ine-2-carboxylic acid (1-methyl-piperidin-4-ylmethyl)-amide | | AnalpH2_MeOH_QC_V1: Rt: 5.53 min, m/z 397.3 [M + H]+ AnalpH9_MeOH_QC_V1: Rt: 8.05 min; m/z 397.3 [M + H]+ | 51 mg, 61%, colour-less gum |
| 60 | {4-[(7-Benzyloxy-2,3-dihydro-benzo[1,4]diox-ine-2-carbonyl)-amino]-cyclohexyl}-carbamic acid tert-butyl ester | Chiral | AnalpH2_MeOH_ 4min, Rt: 3.49 min, m/z 383.3 [M + H]+ | 110 mg, 65% |
| 61 | 7-Benzyloxy-2,3-dihydro-benzo[1,4]diox-ine-2-carboxylic acid (1H-imidazol-2-yl)-amide; formic acid salt | | AnalpH2_MeOH_QC_V1: Rt: 5.94 min, m/z 352.1 [M + H]+ AnalpH9_MeOH_QC_V1: Rt: 7.65 min, m/z 352.2 [M + H]+ | 9.0 mg, 12%, white solid |
| 62 | 7-Benzyloxy-2,3-dihydro-benzo[1,4]diox-ine-2-carboxylic acid 3-(4-methyl-piperazin-1-ylmethyl)-benzylamide | | AnalpH2_MeOH_QC_V1: Rt: 5.81 min, m/z 488.3 [M + H]+ AnalpH9_MeOH_QC_V1: Rt: 8.18 min, m/z 488.3 [M + H]+ $^1$H NMR (400 MHz, DMSO-d6): 8.62 (t, d = 6.1 Hz, 1H) 7.41-7.24 (m, 5H) 7.18 (t, J = 7.3 Hz, 1H) 7.12-6.98 (m, 3H) 6.76 (d, J = 9.0, 1H) 6.61 (d, J = 2.9 Hz, 1H) 6.50 (dd, J = 9.0, 2.9 Hz, 1H) 4.98 (s, 2H) 4.82 (t, J = 3.5 Hz, 1H) 4.36-4.17 (m, 4H) 3.33 (s, 2H) 2.40-2.15 (m, 8H) 2.09 (s, 3H) | 73.6 mg, 43%, brown solid |
| 63 | (7-Benzyloxy-2,3-dihydro-benzo[1,4]diox-in-2-yl)-(4-pyridin-4-ylmethyl-piperazin-1-yl)-methanone | | AnalpH2_MeOH_QC_V1: Rt: 6.28 min, m/z 446.2 [M + H]+ AnalpH9_MeOH_QC_V1: Rt 7.98 min, m/z 446.2 [M + H]+ | 92.2 mg, 59%, white solid |

| E.g. No. | Chemical Name | Compound | Analytical data | Mass, % yield, state |
|---|---|---|---|---|
| 64 | (7-Benzyloxy-2,3-dihydro-benzo[l,4]diox-in-2-yl)-[4-(tetrahydro-pyran-4-ylmethyl)-piperazin-1-yl]-methanone | | AnalpH2_MeOH_QC_V1: Rt: 5.59 min, m/z 453.3 [M + H]+ AnalpH9_MeOH_QC_V1: Rt 8.16 min, m/z 453.3 [M + H]+ | 44.0 mg, 28%, off-white solid |
| 65 | 7-Benzyloxy-2,3-dihydro-benzo[l,4]diox-ine-2-carboxylic acid 4-morpholin-4-ylmethyl-benzylamide | | AnalpH2_MeOH_QC_V1: Rt: 5.52 min, m/z 475.3 [M + H]+ AnalpH9_MeOH_QC_V1: Rt: 7.92 min, m/z 475.3 [M + H]+ | 38 mg, 62%, white solid |
| 66 | 7-Benzyloxy-2,3-dihydro-benzo[l,4]diox-ine-2-carboxylic acid 3-morpholin-4-ylmethyl-benzylamide | | AnalpH2_MeOH_QC_V1: Rt: 5.57 min, m/z 475.3 [M + H]+ AnalpH9_MeOH_QC_V1: Rt: 7.95 min, m/z 475.3 [M + H]+ | 26 mg, 42%, light brown gum |
| 67 | 7-Benzyloxy-2,3-dihydro-benzo[l,4]diox-ine-2-carboxylic acid (pyridin-3-ylmethyl)-amide | | AnalpH2_MeOH_QC_V1: Rt: 6.39 min, m/z 377.3 [M + H]+ AnalpH9_MeOH_QC_V1: Rt: 7.44 min, m/z 377.3 [M + H]+ | 18 mg, 48%, light brown gum |
| 68 | 7-Benzyloxy-2,3-dihydro-benzo[l,4]diox-ine-2-carboxylic acid (pyridin-4-ylmethyl)-amide | | AnalpH2_MeOH_QC_V1: Rt: 5.80 min, m/z 377.3 [M + H]+ AnalpH9_MeOH_QC_V1: Rt: 7.39 min, m/z 377.3 [M + H]+ | 18 mg, 48%, light brown solid |
| 69 | 3-{[(7-Benzyloxy-2,3-dihydro-benzo[l,4]diox-ine-2-carbonyl)-amino]-methyl}-morpholine-4-carboxylic acid tert-butyl ester | | AnalpH2_MeOH_4min, Rt: 3.33 min, m/z 485.3 [M + H]+ | 75 mg, 91%, light yellow oil |

| E.g. No. | Chemical Name | Compound | Analytical data | Mass, % yield, state |
|---|---|---|---|---|
| 70 | 7-Benzyloxy-2,3-dihydro-benzo[1,4]dioxine-2-carboxylic acid (2-oxo-1,2-dihydro-pyridin-4-ylmethyl)-amide | | AnalpH2_MeOH_QC_V1: Rt: 7.10 min, m/z 393.2 [M + H]$^+$ AnalpH9_MeOH_QC_V1: Rt: 7.11 min, m/z 393.2 [M + H]$^+$ | 35 mg, 64%, light brown solid |
| 71 | 7-Benzyloxy-2,3-dihydro-benzo[1,4]dioxine-2-carboxylic acid (2-oxo-piperidin-4-ylmethyl)-amide | | AnalpH2_MeOH_QC_V1: Rt: 7.14 min, m/z 397.2 [M + H]$^+$ AnalpH9_MeOH_QC_V1: Rt: 7.16 min, m/z 397.2 [M + H]$^+$ | 24 mg, 43%, light brown solid |
| 72 | 7-Benzyloxy-2,3-dihydro-benzo[1,4]dioxine-2-carboxylic acid (2-fluoro-pyridin-4-ylmethyl)-amide | | AnalpH2_MeOH_QC_V1: Rt: 7.55 min, m/z 395.2 [M + H]$^+$ AnalpH9_MeOH_QC_V1: Rt: 7.55 min, m/z 395.2 [M + H]$^+$ | 23 mg, 41%, white solid |
| 73 | 7-Benzyloxy-2,3-dihydro-benzo[1,4]dioxine-2-carboxylic acid (1H-pyrazol-4-ylmethyl)-amide | | AnalpH2_MeOH_QC_V1: Rt: 7.22 min, m/z 366.2 [M + H]$^+$ AnalpH9_MeOH_QC_V1: Rt: 7.24 min, m/z 366.2 [M + H]$^+$ | 32 mg, 62%, white solid |

Example 74: Synthesis of 7-Benzyloxy-2,3-dihydro-benzo[1,4]dioxine-2-carboxylic acid 4-piperazin-1-ylmethyl-benzylamide

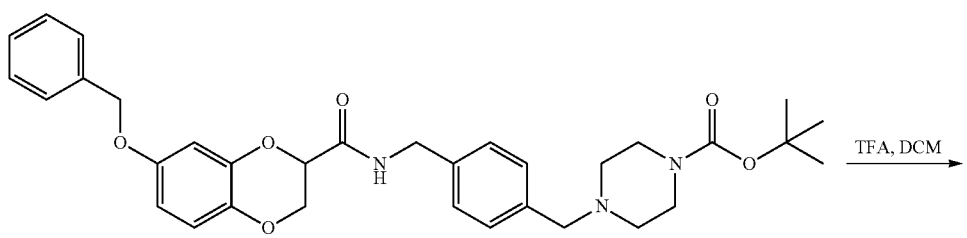

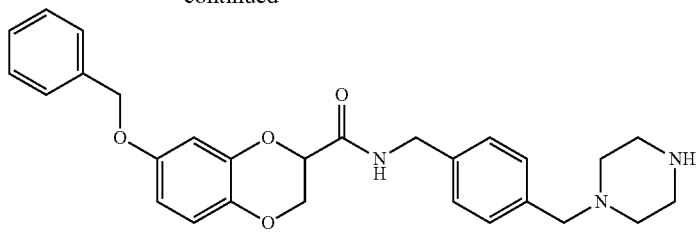

To a solution of 4-(4-{[(7-benzyloxy-2,3-dihydro-benzo[1,4]dioxine-2-carbonyl)-amino]-methyl}-benzyl)-piperazine-1-carboxylic acid tert-butyl ester (80 mg 0.139 mmol) in DCM (3 mL) under nitrogen atmosphere was added trifluoroacetic acid (0.5 mL) dropwise. The mixture was stirred at RT for 1 h. The reaction mixture was concentrated in vacuo, and the crude product was then neutralised with a solution of 7M ammonia in methanol (2 mL) and the solvent removed under reduced pressure. The compound was purified by reverse phase preparative HPLC-MS to afford 7-benzyloxy-2,3-dihydro-benzo[1,4]dioxine-2-carboxylic acid 4-piperazin-1-ylmethyl-benzylamide (49 mg, 74%) as a white solid.

AnalpH2_MeOH_QC_V1: Rt: 5.36 min, m/z 474.3 [M+H]$^+$

AnalpH9_MeOH_QC_V1: Rt: 7.75 min, m/z 474.3 [M+H]$^+$ $^1$H NMR (400 MHz, CD$_2$Cl$_2$): 7.37-7.12 (m, 9H), 6.86 (bs, 1H), 6.81 (dd, J=2.8 Hz, J=9.2 Hz, 1H), 6.56-6.56 (m, 1H), 6.52 (dd, J=2.8 Hz, J=8.8 Hz, 1H), 4.94 (s, 2H), 4.71 (dd, J=2.0 Hz, J=6.4 Hz, 1H), 4.43 (m, 3H), 4.20 (m, 1H), 3.58 (s, 2H), 2.82 (s, 4H), 2.31 (s, 4H)

The following compounds were made analogously using General Method E

Example 77: Synthesis of 3-((R)-7-Benzyloxy-2,3-dihydro-benzo[1,4]dioxin-2-ylmethyl)-8-methyl-1,3,8-triaza-spiro[4.5]decane-2,4-dione

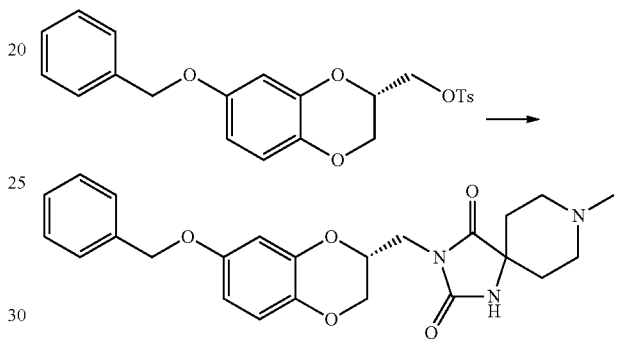

A mixture of 8-methyl-1,3,8-triaza-spiro[4.5]decane-2,4-dione (30 mg, 0.16 mMol, 2 eq.) and K$_2$CO$_3$ (79 mg, 0.57 mMol, 7.0 eq) in DMF (3 mL) was sonicated for 10 min, followed by addition of a solution of toluene-4-sulfonic acid 7-benzyloxy-2,3-dihydro-benzo[1,4]dioxin-2-ylmethyl ester (35 mg, 0.08 mMol, 1 eq.) in DMF (2 mL). The reaction was heated at 60° C. for 16 h, and then at 90° C. for 4 h. The solvent was removed in vacuo and the residue dissolved in EtOAc. The organic extract was washed with sat. aq. NaHCO$_3$, dried (MgSO$_4$) and concentrated in vacuo.

| E.g. No. | Chemical Name | Compound | Analytical data | Mass, % yield, state |
|---|---|---|---|---|
| 75 | 7-Benzyloxy-2,3-dihydro-benzo[1,4]dioxine-2-carboxylic acid (4-amino-cyclohexyl)-amide | Chiral | AnalpH2_MeOH_QC_V1: Rt: 5.47 min, m/z 383.2 [M + H]$^+$ AnalpH9_MeOH_QC_V1: Rt: 7.42 min, m/z 383.2 [M + H]$^+$ | 40 mg, 46%, white solid |
| 76 | 7-Benzyloxy-2,3-dihydro-benzo[1,4]dioxine-2-carboxylic acid (morpholin-3-ylmethyl)-amide | | AnalpH2_MeOH_QC_V1: Rt: 5.24 min, m/z 385.2 [M + H]$^+$ AnalpH9_MeOH_QC_V1: Rt: 7.25 min, m/z 385.2 [M + H]$^+$ | 47 mg, 79%, white solid |

Purification by preparative HPLC-MS afforded 3-((R)-7-benzyloxy-2,3-dihydro-benzo[1,4]dioxin-2-ylmethyl)-8-methyl-1,3,8-triaza-spiro[4.5]decane-2,4-dione as a white solid (29.8 mg, 0.068 mMol, 85%).

AnalpH2_MeOH_QC_V1, Rt: 5.45 min, m/z 438.2 [M+H]$^+$

AnalpH9_MeOH_QC_V1, Rt: 7.81 min, m/z 438.2 [M+H]$^+$

1H-NMR (400 MHz, DMSO-D$_6$) δ 1.46-1.55 (m, 2H), 1.70-1.87 (m, 2H), 2.15-2.21 (m, 5H), 2.55-2.70 (m, 2H), 352-3.67 (m, 2H), 3.87-3.09 (m, 1H), 4.14-4.17 (m, 1H), 4.32-4.37 (m, 1H), 4.95 (s, 2H), 6.42-6.46 (m. 2H), 6.74 (d, J=8.7 Hz, 1H), 7.19-7.47 (m, 5H), 8.74 (s, 1H)

Example 78: Synthesis of 3-((R)-7-Benzyloxy-2,3-dihydro-benzo[1,4]dioxin-2-ylmethyl)-1-pyridin-2-yl-imidazolidine-2,4-dione

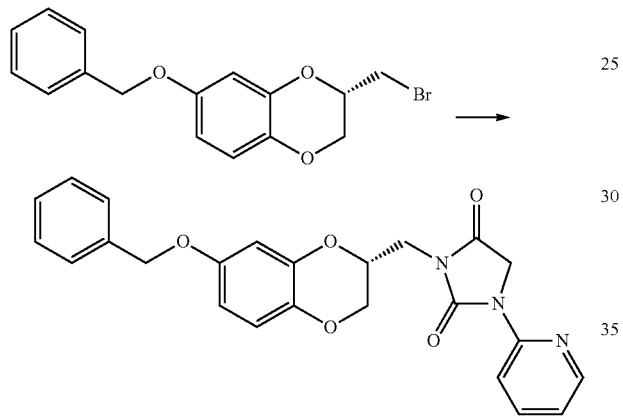

To a stirred mixture of 1-pyridin-2-yl-imidazolidine-2,4-dione (63 mg, 0.36 mMol, 1.0 eq.) and K$_2$CO$_3$ (109 mg, 0.78 mMol, 1.1 eq.) in DMF (20 mL) was added (S)-7-benzyloxy-2-bromomethyl-2,3-dihydro-benzo[1,4]dioxine (120 mg, 0.36 mMol, 1.0 eq.) and the mixture heated at 50° C. for 16 h. A further portion of 1-pyridin-2-yl-imidazolidine-2,4-dione (50 mg) and K$_2$CO$_3$ (109 mg) were added and the reaction mixture was heated at 60° C. for 16 h, and then at 90° C. for 4 h. The reaction mixture was concentrated in vacuo and the resulting residue dissolved in MeOH and filtered. The crude product was loaded onto a SCX cartridge, washed with methanol, then eluted with ammonia in methanol and the product-containing fractions concentrated in vacuo. Purification by column chromatography followed by reverse phase preparative HPLC-MS afforded the formate salt of 3-((R)-7-benzyloxy-2,3-dihydro-benzo[1,4]dioxin-2-ylmethyl)-1-pyridin-2-yl-imidazolidine-2,4-dione as an off-white solid (2.46 mg, 0.005 mMol, 1.4%).

AnalpH2_MeOH_QC_V1, Rt: 8.28 min, m/z 432.2 [M+H]$^+$

AnalpH9_MeOH_QC_V1, Rt: 8.27 min, m/z 432.3 [M+H]$^+$

Example 79: Synthesis of 3-((R)-7-Benzyloxy-2,3-dihydro-benzo[1,4]dioxin-2-ylmethyl)-1-piperidin-4-yl-imidazolidine-2,4-dione

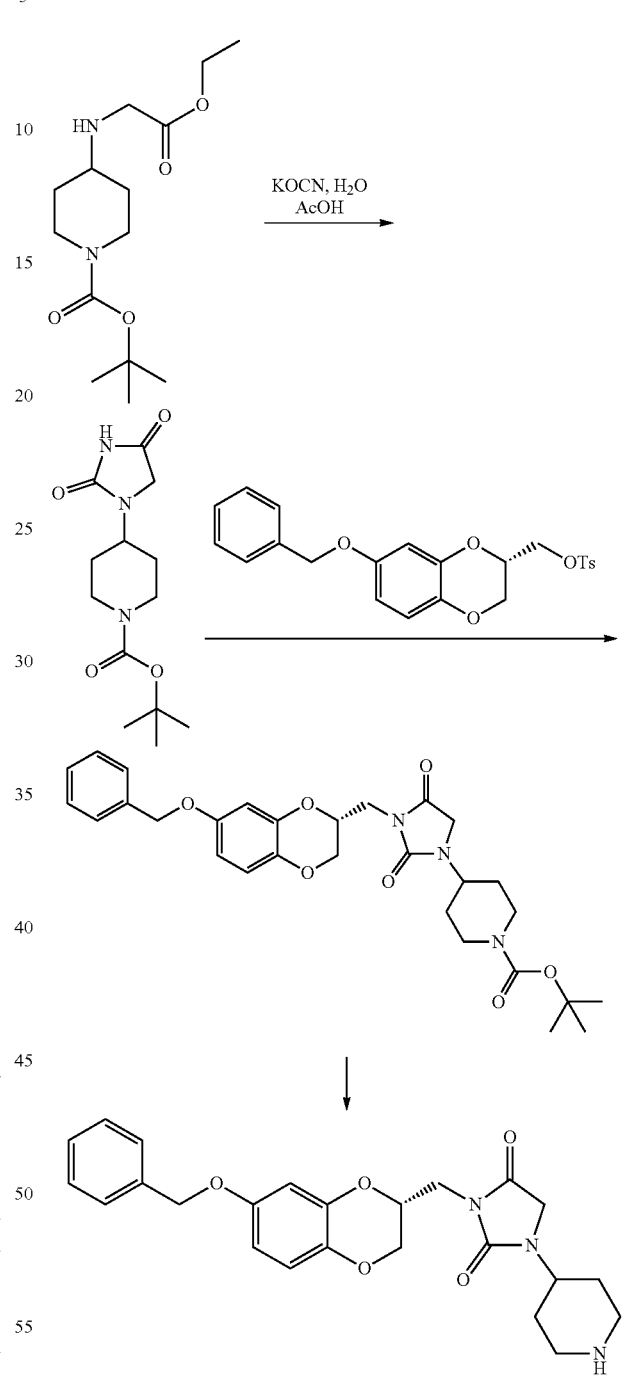

A mixture of 4-(2,4-dioxo-imidazolidin-1-yl)-piperidine-1-carboxylic acid tert-butyl ester (80 mg, 0.28 mMol, 2 eq.) and K$_2$CO$_3$ (136 mg, 0.98 mMol, 7.0 eq) in DMF (3 mL) was sonicated at 40° C. for 10 min, followed by the addition of a solution of toluene-4-sulfonic acid 7-benzyloxy-2,3-dihydro-benzo[1,4]dioxin-2-ylmethyl ester (80 mg, 0.19 mMol, 1 eq.) in DMF (3 mL). The reaction mixture was heated at 60° C. for 16 h and then at 90° C. for 4 h. The solvent was removed in vacuo and the residue dissolved in EtOAc. The organic extract was washed with sat. aq. NaHCO₃, dried (MgSO₄) and concentrated in vacuo to afford 4-[3-((R)-7-benzyloxy-2,3-dihydro-benzo[1,4]dioxin-2-ylmethyl)-2,4-dioxo-imidazolidin-1-yl]-piperidine-1-carboxylic acid tert-butyl ester (66 mg) which was used directly in the subsequent reaction.

The crude 4-[3-((R)-7-benzyloxy-2,3-dihydro-benzo[1,4]dioxin-2-ylmethyl)-2,4-dioxo-imidazolidin-1-yl]-piperidine-1-carboxylic acid tert-butyl ester (66 mg) was dissolved in DCM (8 mL) and TFA (2 mL) was added and the reaction mixture stirred at room temperature for 1 h. The mixture was concentrated in vacuo and the resulting residue was loaded onto a SCX-2 cartridge, washed with methanol then eluted with ammonia in methanol and the product-containing fractions were concentrated in vacuo. Purification by preparative HPLC-MS afforded 3-((R)-7-benzyloxy-2,3-dihydro-benzo[1,4]dioxin-2-ylmethyl)-1-piperidin-4-yl-imidazolidine-2,4-dione as a white solid (10.2 mg, 0.02 mMol, 8.3%).

AnalpH2_MeOH_QC_V1, Rt: 5.53 min, m/z 438.3 [M+H]⁺

AnalpH9_MeOH_QC_V1, Rt: 7.59 min, m/z 438.3 [M+H]⁺

Example 80: Synthesis of 1-(7-benzyloxy-2,3-dihydro-benzo[1,4]dioxin-2-ylmethyl)-3-(1-methyl-piperidin-4-yl)-urea

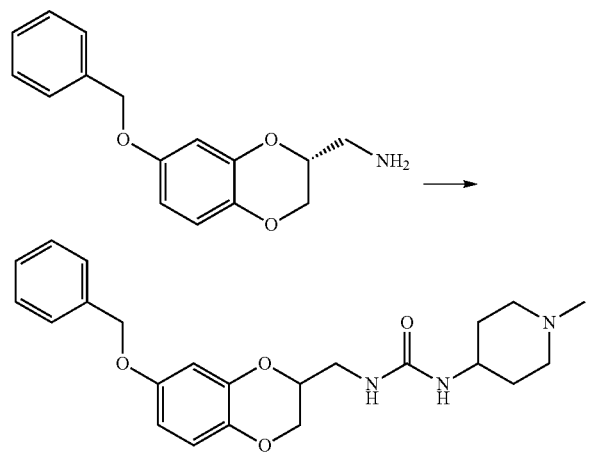

To a stirred solution of phosgene (20% in toluene, 0.37 mL, 0.74 mMol, 1 eq.) in DCM (14 mL) under an atmosphere of nitrogen and at −20° C. was slowly added a solution of 1-methyl-piperidin-4-ylamine (85 mg, 0.74 mMol, 1 eq.) in DCM (6 mL) followed by NEt₃ (188 mg, 1.86 mMol, 2.5 eq.). The reaction mixture was stirred at −20° C. for 5 min and then at room temperature for 1 h. The reaction mixture was concentrated in vacuo and the resulting residue dissolved in DCM (15 mL), cooled to 0° C. and a solution of C—((R)-7-benzyloxy-2,3-dihydro-benzo[1,4]dioxin-2-yl)-methylamine (200 mg, 0.74 mMol, 1 eq.) in DCM was added. The reaction mixture was stirred at 0° C. for 15 min and then at room temperature for 4 h. The reaction was quenched by the addition of methanol and the mixture was concentrated in vacuo. Purification by preparative HPLC-MS afforded 1-(7-benzyloxy-2,3-dihydro-benzo[1,4]dioxin-2-ylmethyl)-3-(1-methyl-piperidin-4-yl)-urea as a white solid (56.8 mg, 0.14 mMol, 18.6%).

AnalpH2_MeOH_QC_V1, Rt: 5.62 min, m/z 412.2 [M+H]⁺

AnalpH9_MeOH_QC_V1, Rt: 7.89 min, m/z 412.3 [M+H]⁺

¹H-NMR (400 MHz, DMSO-D₆) δ 1.14-1.39 (m, 2H), 1.58-1.74 (m, 2H), 1.79-2.00 (m, 2H), 2.08 (s, 3H), 2.50-2.62 (m, 2H), 3.18-3.27 (m, 3H), 3.76 (dd, J=11.4, 7.3 Hz, 1H), 4.00-4.24 (m, 2H), 4.97 (s, 2H), 5.81-6.07 (m, 2H), 6.37-6.56 (m, 2H), 6.73 (d, J=9.2 Hz, 1H), 7.20-7.51 (m, 5H)

Example 81: Synthesis of 3-(7-Benzyloxy-2,3-dihydro-benzo[1,4]dioxin-2-ylmethyl)-1-methyl-1-(1-methyl-piperidin-4-yl)-urea

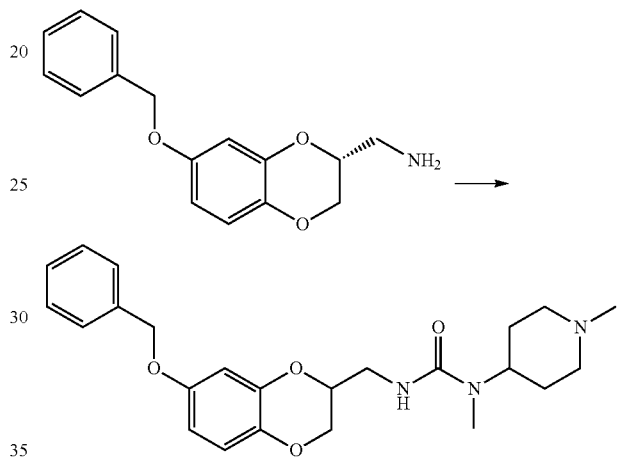

To a stirred solution of phosgene (0.19 mL, 0.37 mMol, 1 eq., 20% in toluene) in DCM (7 mL) under an atmosphere of nitrogen and at −20° C. was slowly added a solution of methyl-(1-methyl-piperidin-4-yl)-amine (47 mg, 0.37 mMol, 1 eq.) in DCM (3 mL) followed by NEt₃ (93 mg, 0.92 mMol, 2.5 eq.). The reaction mixture was stirred at −20° C. for 5 min and then at room temperature for 1 h. The reaction mixture was concentrated in vacuo and the resulting residue dissolved in DCM (10 mL), cooled to 0° C. and a solution of C—((R)-7-benzyloxy-2,3-dihydro-benzo[1,4]dioxin-2-yl)-methylamine (100 mg, 0.37 mMol, 1 eq.) in DCM was added. The reaction mixture was stirred at 0° C. for 15 min and then at 40° C. for 16 h. The reaction was quenched with methanol and the reaction mixture was concentrated in vacuo. Purification by preparative HPLC-MS afforded 3-(7-benzyloxy-2,3-dihydro-benzo[1,4]dioxin-2-ylmethyl)-1-methyl-1-(1-methyl-piperidin-4-yl)-urea (18.0 mg, 0.042 mMol, 11%).

AnalpH2_MeOH_QC_V1, Rt: 5.57 min, m/z 426.3 [M+H]⁺

AnalpH9_MeOH_QC_V1 Rt: 7.99 min m/z 426.3 [M+H]⁺

¹H-NMR (400 MHz, DMSO-Ds) δ 1.39-1.42 (m, 2H), 1.58-1.68 (m, 2H), 1.87-1.92 (m, 2H), 2.14 (s, 3H), 2.65 (s, 3H), 2.77-2.80 (m, 2H), 3.18-3.25 (m, 1H), 3.32-3.38 (m, 1H), 3.82-3.92 (m, 2H), 4.14-4.17 (m, 2H), 5.01 (s, 2H), 6.47-6.56 (m, 3H), 6.76-6.78 (d, J=8.8 Hz, 1H), 7.30-7.43 (m, 5H).

Example 82: Synthesis of 4-methyl-piperazine-1-carboxylic acid ((R)-7-benzyloxy-2,3-dihydro-benzo[1,4]dioxin-2-ylmethyl)-amide

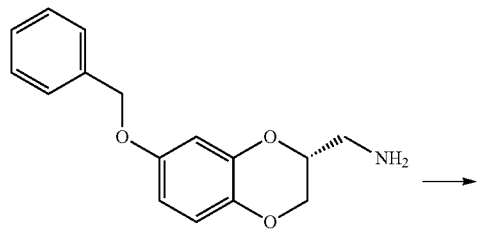

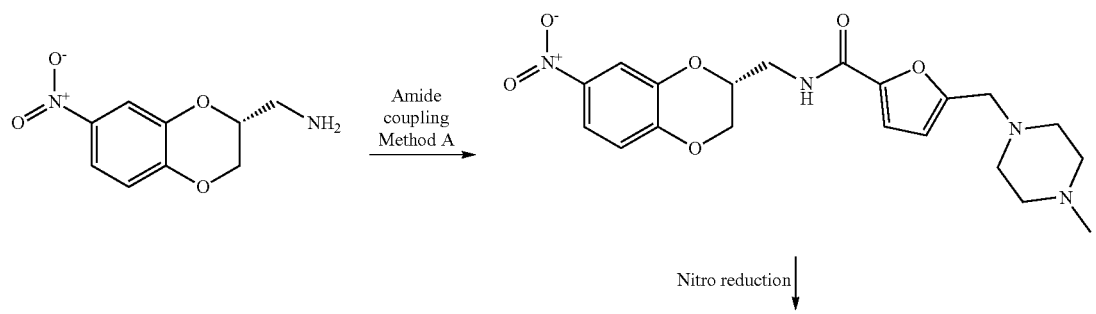

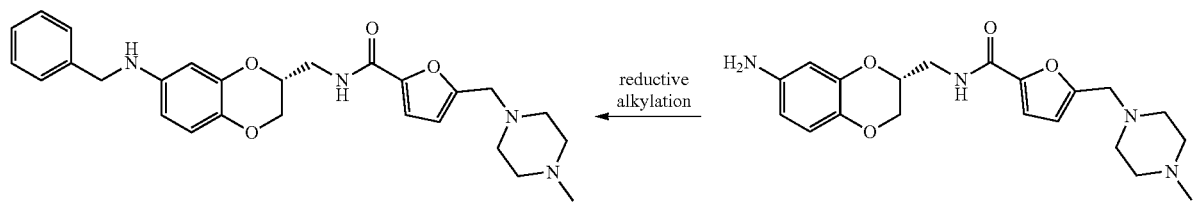

-continued

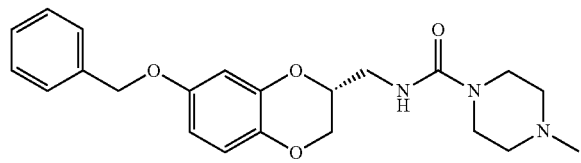

To a stirred solution of C—((R)-7-benzyloxy-2,3-dihydro-benzo[1,4]dioxin-2-yl)-methylamine (100 mg, 0.37 mMol, 0.7 eq.) in DCM (5 mL) was added 4-methyl-piperazine-1-carbonyl chloride (100 mg, 0.50 mMol, 1 eq.) followed by NEt₃ (126 mg, 1.25 mMol, 2.5 eq.) and the reaction mixture was stirred at room temperature for 72 h. The reaction was quenched with methanol and the reaction mixture was concentrated in vacuo. Purification by preparative HPLC-MS afforded 4-methyl-piperazine-1-carboxylic acid ((R)-7-benzyloxy-2,3-dihydro-benzo[1,4]dioxin-2-ylmethyl)-amide as a white solid (64.8 mg, 0.16 mMol, 43.2%).

AnalpH2_MeOH_QC_V1, Rt: 5.47 min, m/z 398.3 [M+H]⁺

AnalpH9_MeOH_QC_V1, Rt: 7.79 min, m/z 398.3 [M+H]⁺

Example 83: Synthesis of 5-(4-Methyl-piperazin-1-ylmethyl)-furan-2-carboxylic acid ((R)-7-benzylamino-2,3-dihydro-benzo[1,4]dioxin-2-ylmethyl)-amide To a solution of 5-(4-methyl-piperazin-1-ylmethyl)-furan-2-carboxylic acid ((R)-7-amino-2,3-dihydro-benzo[1,4]dioxin-2-ylmethyl)-amide (50 mg, 0.13 mmol) in anhydrous 3:1 DCM:MeOH (4 mL) at RT was added benzaldehyde (19 uL, 0.19 mmol), then AcOH (11 uL, 0.19 mmol) and the mixture was stirred at RT for 16 h. Sodium borohydride (7 mg, 0.19 mmol) was added and the mixture stirred at RT for 4 h, then the volatiles were removed in vacuo. The resulting residue was loaded onto a SCX-2 cartridge, washed with methanol, then eluted with a solution of 0.5M ammonia in methanol and the product-containing fractions concentrated in vacuo. The crude material was purified by reverse phase prep HPLC to give 5-(4-methyl-piperazin-1-ylmethyl)-furan-2-carboxylic acid ((R)-7-benzylamino-2,3-dihydro-benzo[1,4]dioxin-2-ylmethyl)-amide (19.8 mg, 20%) as a white solid.

AnalpH2_MeOH_QC_V1, Rt: 4.32 min, m/z 777.3 [M+H]⁺

AnalpH9_MeOH_QC_V1, Rt: 7.69 min, m/z 477.3 [M+H]⁺

Example 84 Synthesis of ({4-[(7-Benzyloxy-2,3-dihydro-benzo[1,4]dioxine-2-carbonyl)-amino]-cyclohexyl-carbamoyl}-methyl)-carbamic acid tert-butyl ester

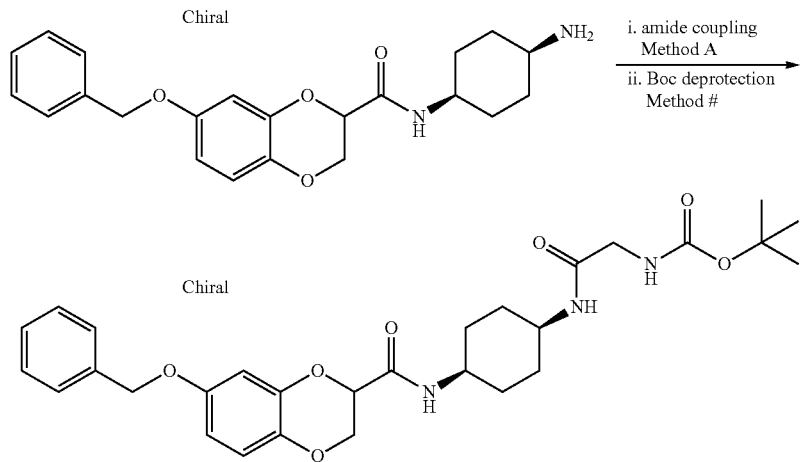

The title compound was prepared by general amide coupling method A, using 7-benzyloxy-2,3-dihydro-benzo[1,4]dioxine-2-carboxylic acid (4-amino-cyclohexyl)-amide (45 mg, 0.11 mmol) and Boc-Glycine (21 mg, 0.11 mmol) in DMF, and isolated using work-up method A2 to afford ({4-[(7-benzyloxy-2,3-dihydro-benzo[1,4]dioxine-2-carbonyl)-amino]-cyclohexyl-carbamoyl}-methyl)-carbamic acid tert-butyl ester (41 mg, 70%)

AnalpH2_MeOH_4 min, Rt: 3.35 min, m/z 540.4 [M+H]+
AnalpH9_MeOH_4 min, Rt: 7.69 min, m/z 540.4 [M+H]+

Example 85: Synthesis of 7-Benzyloxy-2,3-dihydro-benzo[1,4]dioxine-2-carboxylic acid [4-(2-amino-acetylamino)-cyclohexyl]-amide The title compound was prepared by general method E, using ({4-[(7-benzyloxy-2,3-dihydro-benzo[1,4]dioxine-2-carbonyl)-amino]-cyclohexyl-carbamoyl}-methyl)-carbamic acid tert-butyl ester (41 mg, 0.077 mmol) and purified by reverse phase preparative HPLC to afford 7-benzyloxy-2,3-dihydro-benzo[1,4]dioxine-2-carboxylic acid [4-(2-amino-acetylamino)-cyclohexyl]-amide (23 mg, 70%) as a white solid.

AnalpH2_MeOH_QC_V1, Rt: 5.62 min, m/z 440.3 [M+H]+
AnalpH9_MeOH_QC_V1, Rt: 7.45 min, m/z 440.4 [M+H]+

Example 86: Synthesis of C—((R)-7-Benzyloxy-2,3-dihydro-benzo[1,4]dioxin-2-yl)-methylamine

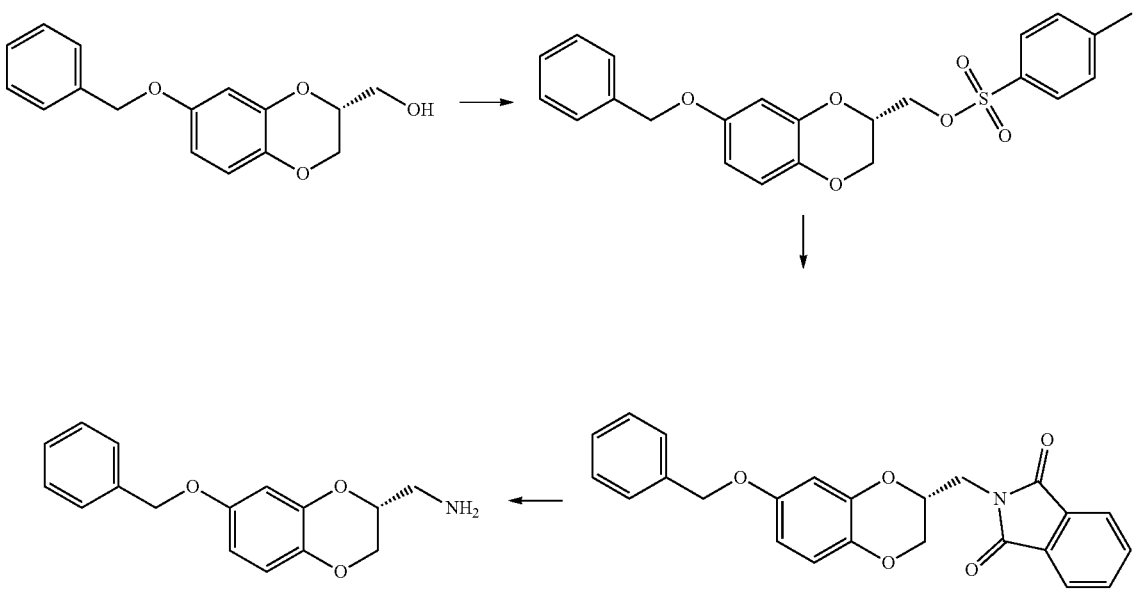

Step 1—Toluene-4-sulfonic acid (S)-7-benzyloxy-2,3-dihydro-benzo[1,4]dioxin-2-ylmethyl ester To a solution of ((R)-7-benzyloxy-2,3-dihydro-benzo[1,4]dioxin-2-yl)-methanol (5.0 g, 18.4 mmol) in DCM (50 ml) under nitrogen was added TEA (7.9 mL, 55.14 mmol) dropwise over 10 min. Then TsCl (4.1 g, 22.0 mmol) was added portionwise over 10 min. The reaction mixture was stirred at room temperature for 16 h. The reaction mixture was quenched with water, and the aqueous layer extracted with DCM (2×100 mL). The combined organic layers were washed with water (2×200 mL) and brine (2×200 mL), dried over $Na_2SO_4$ and concentrated under reduced pressure. The crude product was purified by column chromatography on silica gel (10% EtOAc/Pet ether) to afford toluene-4-sulfonic acid (S)-7-benzyloxy-2,3-dihydro-benzo[1,4]dioxin-2-ylmethyl ester (7 g, 89.7%) as an off-white solid.

AnalpH2_MeCN_UPLC_4 min, Rt: 2.47 min, m/z 427.5 [M+H]+

1H NMR (400 MHz, CDCl3) δ 2.45 (s, 3H), 3.95-4.01 (m, 1H), 4.09-4.28 (m, 3H), 4.37-4.41 (m, 1H), 4.96 (s, 2H), 6.43-6.49 (m, 2H), 6.74 (d, J=8.8 Hz, 1H), 7.31-7.39 (m, 7H), 7.79-7.81 (m, 2H).

Step 2—2-((R)-7-Benzyloxy-2,3-dihydro-benzo[1,4]dioxin-2-ylmethyl)-isoindole-1,3-dione To a solution of toluene-4-sulfonic acid (S)-7-benzyloxy-2,3-dihydro-benzo[1,4]dioxin-2-ylmethyl ester (9.0 g, 21.1 mmol) in DMF (100 ml) was added potassium phthalimide (4.6 g, 25.0 mmol). The mixture was stirred at 90° C. under $N_2$ for 3 h, and then quenched with water. The mixture was extracted with ethyl acetate (3×100 mL) and the combined organic layers were washed with water (2×100 mL), brine (2×100 mL), dried over $Na_2SO_4$ and concentrated under reduced pressure. The crude product was purified by column chromatography on silica gel (20-30% EtAOAc/Pet ether) to afford 2-((R)-7-benzyloxy-2,3-dihydro-benzo[1,4]dioxin-2-ylmethyl)-isoindole-1,3-dione (8.0 g, 94%) as an off white solid.

AnalpH2_MeCN_UPLC_4 min, Rt: 2.4 min, m/z 402.4 [M+H]+

1H NMR (400 MHz, CDCl$_3$): 7.89-7.85 (m, 2H), 7.76-7.71 (m, 2H), 7.41-7.30 (m, 4H), 6.77 (d, J=8.8 Hz, 1H, 6.51-6.47 (m, 1H), 4.95 (s, 1H), 4.51-4.49 (m, 1H), 4.27-4.24 (dd, J=11.4 Hz, J=2.4 Hz, 1H), 4.15-4.06 (m, 2H), 4.01-3.96 (dd, J=11.4 Hz, 6.6 Hz, 1H), 3.92-3.87 (dd, J=14 Hz, 5.2 Hz, 1H), 2.04 (s, 1H), 1.26 (t, J=7 Hz, 1H)

Step 3—C—((R)-7-Benzyloxy-2,3-dihydro-benzo[1,4]dioxin-2-yl)-methylamine

To a stirred solution of 2-((R)-7-benzyloxy-2,3-dihydro-benzo[1,4]dioxin-2-ylmethyl)-isoindole-1,3-dione (10.4 g, 25.9 mmol) in ethanol (150 ml) under nitrogen atmosphere was added hydrazine hydrate (14 mL, 259 mmol) and the mixture heated at 90° C. for 2 h. The reaction mixture was filtered and the residue was washed with DCM (2×200 mL). The combined filtrates were concentrated under reduced pressure, and the crude product was purified by column chromatography on silica gel (60-70% EtOAc/Pet ether) to afford C—((R)-7-benzyloxy-2,3-dihydro-benzo[1,4]dioxin-2-yl)-methylamine (3.2 g, 45.7%) as a pale yellow, gummy solid.

AnalpH2_MeCN_UPLC_4 min Rt: 2.4 min, m/z 272.2 [M+H]+

1H NMR (400 MHz, CDCl3): 7.42-7.29 (m, 5H), 6.76 (d, J=8.8 Hz, 1H), 6.53 (d, J=3.2 Hz, 1H), 6.47 (dd, J=9 Hz, 3.0 Hz, 1H), 5.00 (s, 2H), 4.28 (dd, J=11.4 Hz, J=1.8 Hz, 1H), 4.01 (q, 5.7 Hz, 1H), 3.88 (dd, J=11.6 Hz, 6.6 Hz, 1H), 2.83-2.70 (m, 2H), 1.73 (br s, 2H).

Example 87: Synthesis of 1-[(R)-7-(4-Chloro-benzyloxy)-2,3-dihydro-benzo[1,4]dioxin-2-ylmethyl]-3-(1-methyl-piperidin-4-yl)-urea

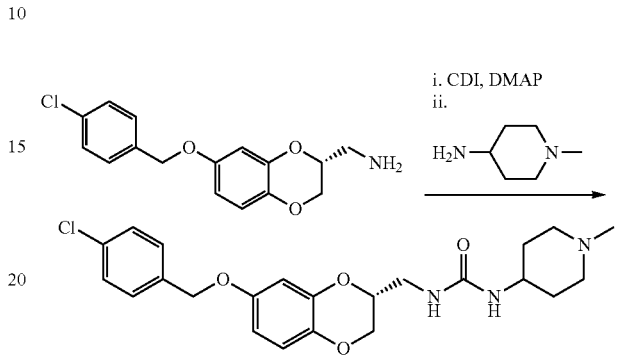

To a solution of [(3R)-6-[(4-chlorophenyl)methoxy]-2,3-dihydro-1,4-benzodioxin-3-yl]methanamine (26 mg, 0.08 mMol, 1 eq.) in DCM (1 mL) was added carbonyldiimidazole (20.6 mg, 0.12 mMol, 1.5 eq.) followed by dimethylaminopyridine (11.4 mg, 0.09 mMol, 1.2 eq.) and the reaction mixture was stirred at room temperature for 1 h. Then 1-methyl-piperidin-4-ylamine (15 uL, 0.12 mMol, 1.5 eq.) was added and the mixture was stirred at room temperature for 1 h. The solvent was then removed under reduced pressure and the crude product purified by preparative HPLC to afford 1-[(R)-7-(4-chloro-benzyloxy)-2,3-dihydro-benzo[1,4]dioxin-2-ylmethyl]-3-(1-methyl-piperidin-4-yl)-urea (30 mg, 0.06 mMol, 78%) as a white solid.

AnalpH2_MeOH_QC_V1, Rt: 6.26 min, m/z 446.3 [M+H]$^+$

AnalpH9_MeOH_QC_V1, Rt: 8.33 min, m/z 446.3 [M+H]$^+$ $^1$H-NMR (400 MHz, DCM-D$_2$) δ 7.33 (s, 4H), 6.74 (d, J=8.8 Hz, 1H), 6.46-6.41 (m, 2H), 4.92 (s, 2H), 4.57 (t, J=6.0 Hz, 1H), 4.23-4.16 (m, 3H), 3.89 (dd, J=7.6 Hz, J=4.0 Hz, 1H), 3.51-3.34 (m, 3H), 2.69 (d, J=12.4 Hz, 2H), 2.18 (s, 3H), 2.03 (t, J=10.8 Hz, 2H), 1.86 (d, J=9.6 Hz, 2H), 1.42 (dd, J=10.8 Hz, J=11.6 Hz, 2H).

Biological Activity

Protein Expression and Purification

For SPR assays pGEX-KRAS(G12V) plasmid was transformed into *E. coli* C41(DE3). Bacterial cells were cultured at 37° C. to an OD$_{600}$ of 0.6 and induced with IPTG (final 0.1 mM) at 18° C. overnight. The GST fusion proteins were extracted from bacteria pellets after cell disruption in 140 mM NaCl, 2.7 mM KCl, 10 mM NaH$_2$PO$_4$, 1.8 mM KH$_2$PO$_4$, 1 mM EDTA, 2 mM MgCl$_2$ pH 7.4 and purified by glutathione-sepharose column chromatography (GE Healthcare), eluting with 50 mM Tris-HCl pH8.0, 10 mM reduced glutathione, 1 mM DTT, 2 mM MgC$_2$. The eluted proteins were dialysed against 50 mM Tris-HCl pH8.0, 1 mM DTT, 2 mM MgCl$_2$ and concentrated to 10 mg/ml using a Biomax-30 ULTRAFREE-15 centrifugal filter device (Millipore). Purified KRAS protein was loaded with GPPNHP as described elsewhere (Pacold et al., 2000). Loaded protein was then purified by gel filtration on a HiLoad Superdex-75 HR column (GE Healthcare) in 1×PBS pH7.4, 5 mM MgCl$_2$ and concentrated for storage.

Protocol for KRas Small-Molecule Screening and Affinity Measurements by SPR

Protein Immobilization

To a previously immobilized CM5 chip (GE Healthcare BR-1005-30) with anti GST antibody via amine coupling method, GST in channel 1 and GST-human KRas166 (G12V) GPPNHP in channel 2 were immobilised. GST was immobilised between 2,000 and 5,000 Response units. KRAS166 (G12V) was immobilized between 10,000 to 15,000 Response Units.

Compound Screening

In a 96 well plate, compounds were diluted in 25 mM, 100 mM NaCl, 5 mM $MgCl_2$ and 5% DMSO Buffer to a final concentration of 100 uM. DCAI was used as positive control. Experiment also included a solvent correction curve for 5% DMSO. Screening and evaluation of the protein immobilization and the compounds screening was done accordingly to the BIACORE T200 control and evaluation software.

Calculations for how many response units are required for a 1:1 ratio of compound/protein interaction are shown below.

Protein immobilisation: 10,000 RU; average fragment 300 Da in size.

$$R_{max}=(MWA/MWL)\times RL\times SM$$

MWA is the molecular weight of the analyte in Da
MWL is the molecular weight of the ligand in Da
RL is the immobilization level in RU
SM is the molar stoichiometry (assume 1:1)
Rmax=300/47,500×10,000×1
Rmax=63 RU.

Cell Viability Assay protocols

Cells (A549 ATCC CCL-185) are cultured in Dulbecco's Modified Eagle's Medium plus 10% foetal calf serum and 2 mM L-glutamine at 37° C., 5% $CO_2$. Cells are plated onto white clear bottom 96-well plates (5000 cells/well in 200 μl media) and left to adhere overnight at 37° C., 5% $CO_2$. Next day, test compound (1 μl at 200× concentration in 100% DMSO) is added to give final test compound concentration 1× in 0.5% DMSO. After 48 h of incubation at 37° C., 5% $CO_2$, 20 μl CellTiter-Glo reagent (Promega G7572) is added into each well. Plates are incubated at room temperature with shaking for 30 min and then luminescence is read using a PheraStar plate reader. The concentration of compounds that decrease cell viability by 50% is calculated from dose response curves generated using Dotmatics data analysis software.

In the DLD1 cell assay, cells (ATCC CCL-221) are cultured in RPMI-1640 medium plus 10% foetal calf serum and 2 mM L-glutamine at 37° C., 5% $CO_2$.

In the H358 cell assay, cells (ATCC CRL-5807) are cultured in RPM-1640 medium plus 10% foetal calf serum and 2 mM L-glutamine at 37° C., 5% $CO_2$.

Protein affinity and cell viability data for compounds of formula I are provided in Table 1.

TABLE 1

| Example No. | Chemical Structure | SPR Response Units | Cell Viability (μM) H358 DLD-1 |
|---|---|---|---|
| 1 | 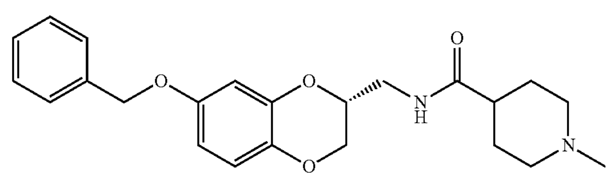 [SMILES: CN1CCC(C(=O)NC[C@@H]2COc3ccc(OCc4ccccc4)cc3O2)CC1] | 48 | 61 13 |
| 2 | 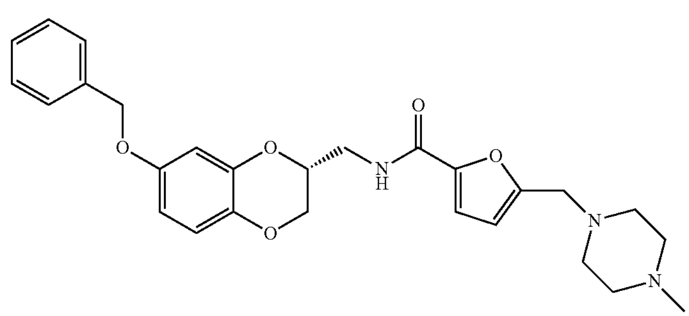 [SMILES: CN1CCN(Cc2ccc(C(=O)NC[C@@H]3COc4ccc(OCc5ccccc5)cc4O3)o2)CC1] | 224 | 43 10 |
| 3 | 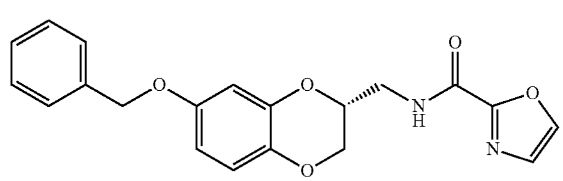 [SMILES: O=C(NC[C@@H]1COc2ccc(OCc3ccccc3)cc2O1)c1ncco1] | 12 | >100 20 |

TABLE 1-continued
| Example No. | Chemical Structure | SPR Response Units | Cell Viability (μM) H358 DLD-1 |
|---|---|---|---|
| 4 | 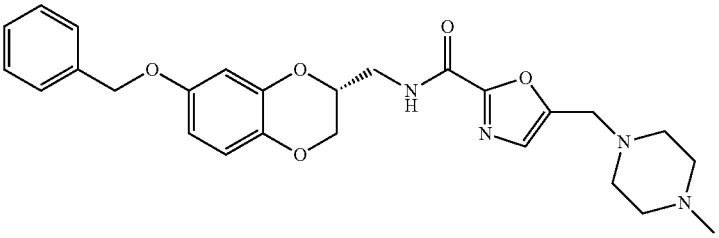 | 66 | 57<br>12 |
| 5 | 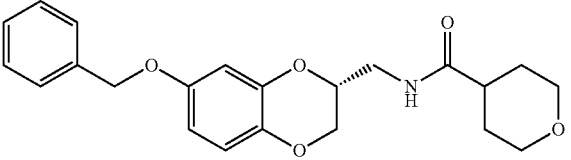 [SMILES: O=C(NC[C@@H]1COc2ccc(OCc3ccccc3)cc2O1)C1CCOCC1] | 25 | |
| 6 | 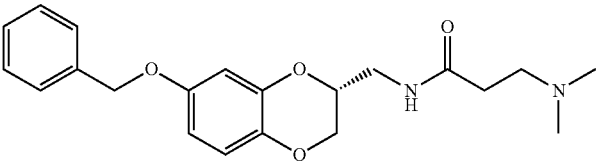 [SMILES: CN(C)CCC(=O)NC[C@@H]1COc2ccc(OCc3ccccc3)cc2O1] | 21 | |
| 7 | 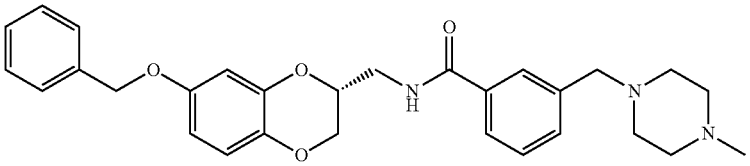 [SMILES: CN1CCN(Cc2cccc(C(=O)NC[C@@H]3COc4ccc(OCc5ccccc5)cc4O3)c2)CC1] | 145 | 19.2<br>10.5 |
| 8 | 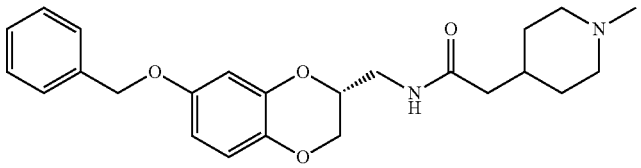 [SMILES: CN1CCC(CC(=O)NC[C@@H]2COc3ccc(OCc4ccccc4)cc3O2)CC1] | 24 | |
| 10 | 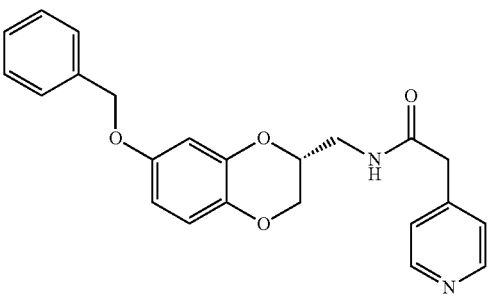 [SMILES: O=C(Cc1ccncc1)NC[C@@H]1COc2ccc(OCc3ccccc3)cc2O1] | 80 | |

TABLE 1-continued

| Example No. | Chemical Structure | SPR Response Units | Cell Viability (μM) H358 DLD-1 |
|---|---|---|---|
| 11 | 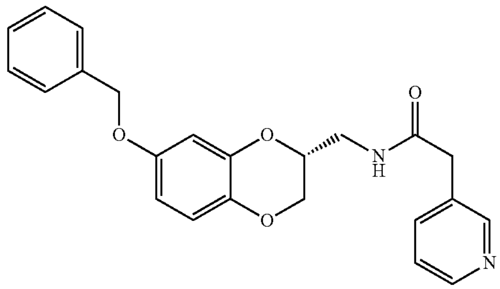 [SMILES: O=C(Cc1cccnc1)NC[C@@H]1COc2ccc(OCc3ccccc3)cc2O1] | | 68 |
| 12 | 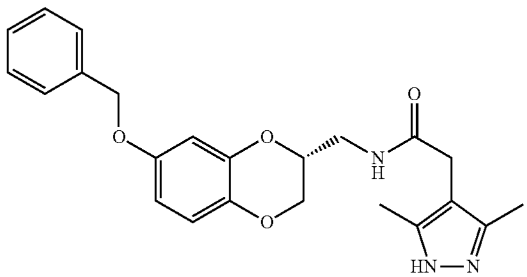 [SMILES: Cc1n[nH]c(C)c1CC(=O)NC[C@@H]1COc2ccc(OCc3ccccc3)cc2O1] | | 53 |
| 14 | 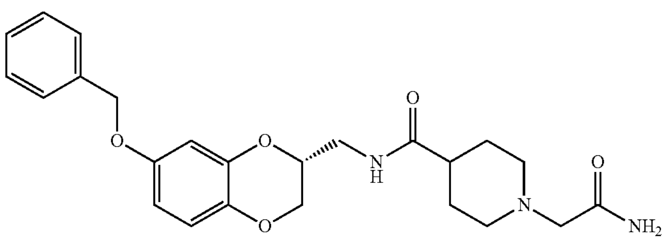 [SMILES: NC(=O)CN1CCC(C(=O)NC[C@@H]2COc3ccc(OCc4ccccc4)cc3O2)CC1] | | 24 |
| 15 | 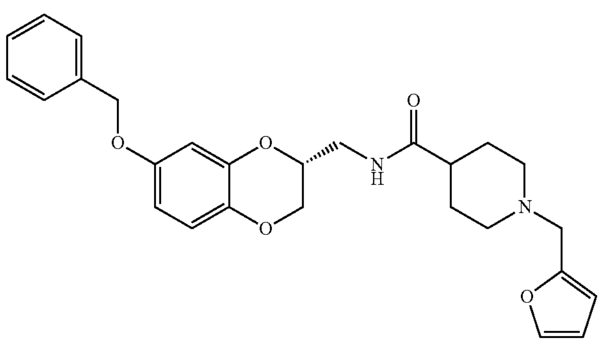 [SMILES: O=C(NC[C@@H]1COc2ccc(OCc3ccccc3)cc2O1)C1CCN(Cc2ccco2)CC1] | | 33 |
| 16 | 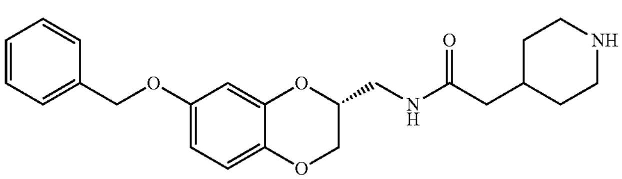 [SMILES: O=C(CC1CCNCC1)NC[C@@H]1COc2ccc(OCc3ccccc3)cc2O1] | | 25 |

TABLE 1-continued
| Example No. | Chemical Structure | SPR Response Units | Cell Viability (μM) H358 DLD-1 |
|---|---|---|---|
| 17 | 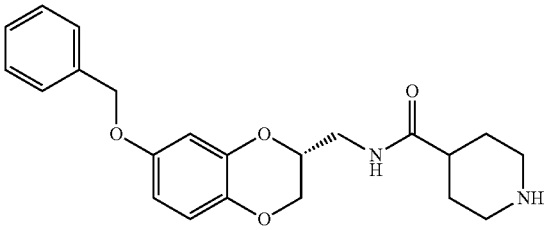 [SMILES: O=C(NC[C@@H]1COc2ccc(OCc3ccccc3)cc2O1)C1CCNCC1] | 22 | |
| 18 | 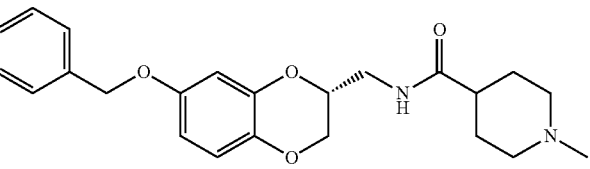 | 61 | 10.0<br>5.4 |
| 19 | 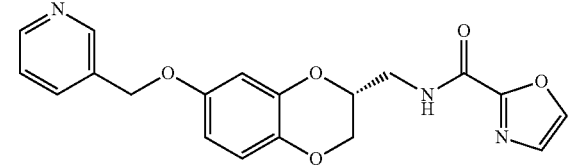 [SMILES: O=C(NC[C@@H]1COc2ccc(OCc3cccnc3)cc2O1)c1ncco1] | 40 | |
| 20 | 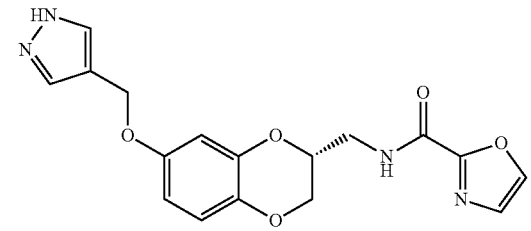 [SMILES: O=C(NC[C@@H]1COc2ccc(OCc3cn[nH]c3)cc2O1)c1ncco1] | 40 | |
| 21 | 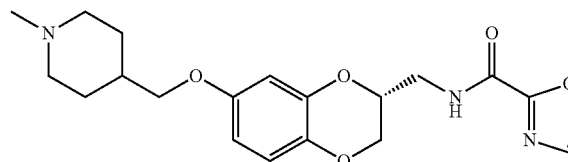 | 9 | |
| 22 | 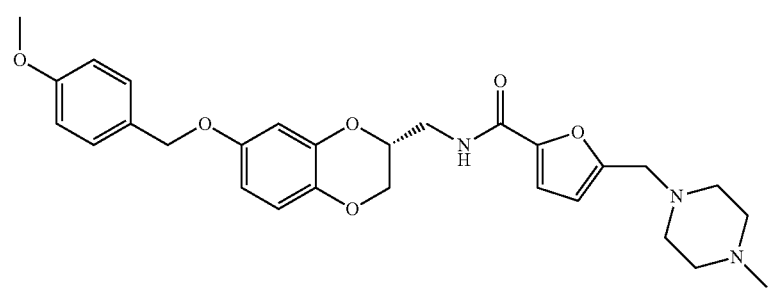 [SMILES: COc1ccc(COc2ccc3c(c2)O[C@H](CNC(=O)c2ccc(CN4CCN(C)CC4)o2)CO3)cc1] | 96 | 46<br>12 |

TABLE 1-continued

| Example No. | Chemical Structure | SPR Response Units | Cell Viability (μM) H358 DLD-1 |
|---|---|---|---|
| 23 | 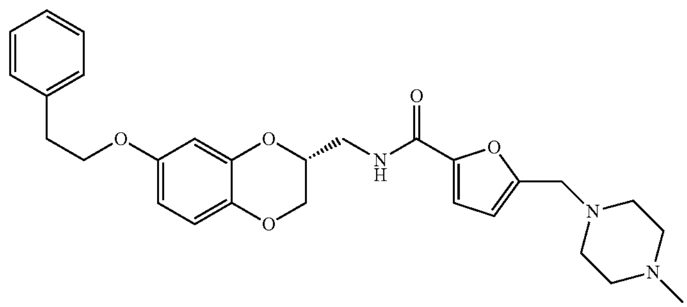 [SMILES: CN1CCN(Cc2ccc(C(=O)NC[C@@H]3COc4ccc(OCCc5ccccc5)cc4O3)o2)CC1] | 86 | 35<br>3.5 |
| 24 | 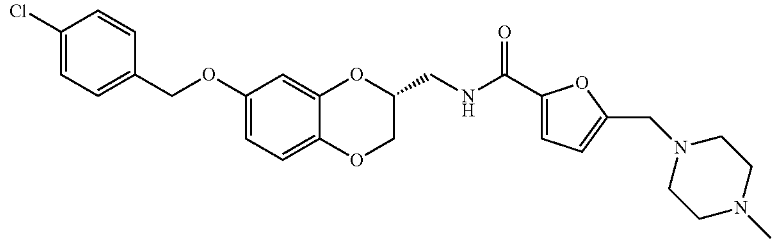 [SMILES: CN1CCN(Cc2ccc(C(=O)NC[C@@H]3COc4ccc(OCc5ccc(Cl)cc5)cc4O3)o2)CC1] | 226 | 49<br>2.5 |
| 25 | 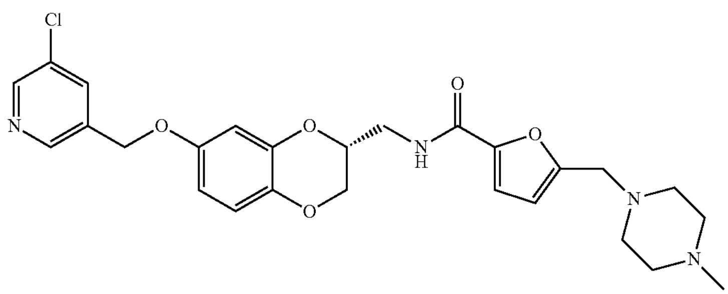 [SMILES: CN1CCN(Cc2ccc(C(=O)NC[C@@H]3COc4ccc(OCc5cncc(Cl)c5)cc4O3)o2)CC1] | 45 | |
| 26 | 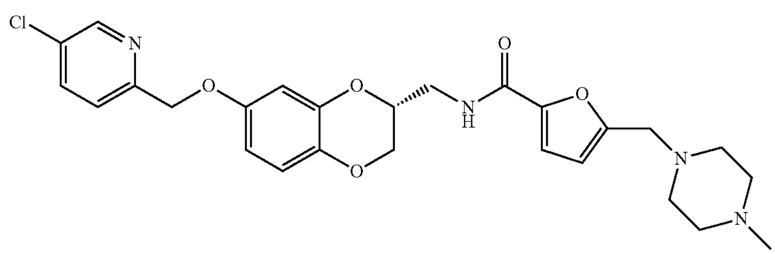 | 48 | |
| 27 | 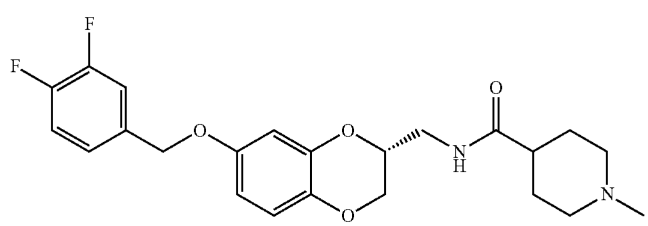 [SMILES: CN1CCC(C(=O)NC[C@@H]2COc3ccc(OCc4ccc(F)c(F)c4)cc3O2)CC1] | 44 | 33.2<br>5.6 |
| 28 | 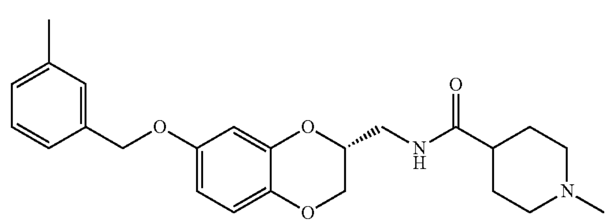 [SMILES: Cc1cccc(COc2ccc3c(c2)O[C@H](CNC(=O)C2CCN(C)CC2)CO3)c1] | 39 | 16.6<br>8.2 |

TABLE 1-continued

| Example No. | Chemical Structure | SPR Response Units | Cell Viability (μM) H358 DLD-1 |
|---|---|---|---|
| 29 | 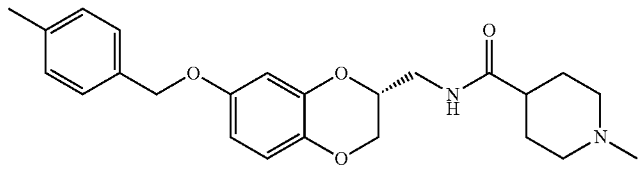 | 37 | 12.5<br>6.8 |
| 30 | 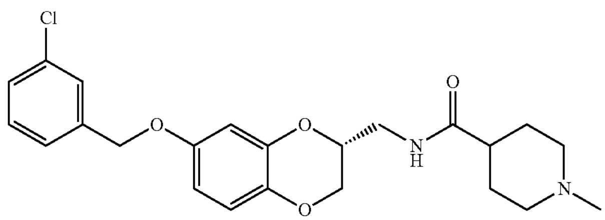 [SMILES: CN1CCC(C(=O)NC[C@@H]2COc3ccc(OCc4cccc(Cl)c4)cc3O2)CC1] | 64 | 16.2<br>3.9 |
| 31 | 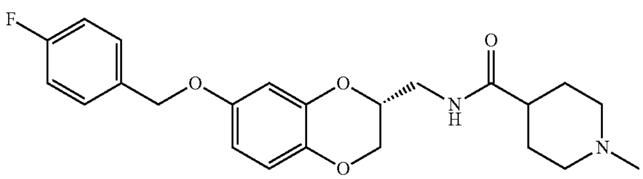 [SMILES: CN1CCC(C(=O)NC[C@@H]2COc3ccc(OCc4ccc(F)cc4)cc3O2)CC1] | 28 | 18.2<br>9.6 |
| 32 | 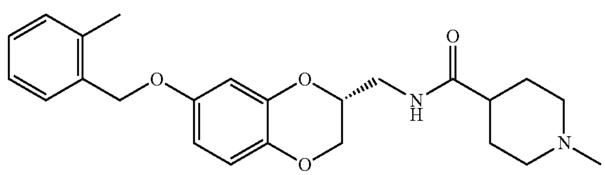 [SMILES: Cc1ccccc1COc1ccc2c(c1)O[C@H](CNC(=O)C1CCN(C)CC1)CO2] | 37 | 26.2<br>15.9 |
| 33 | 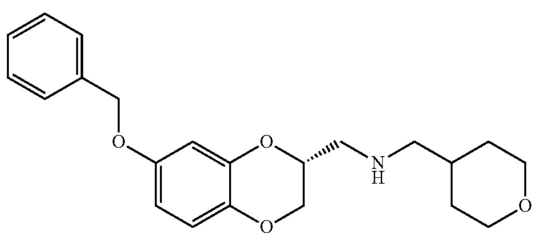 [SMILES: c1ccc(COc2ccc3c(c2)O[C@H](CNCC2CCOCC2)CO3)cc1] | 16 | >100<br>18 |
| 34 | 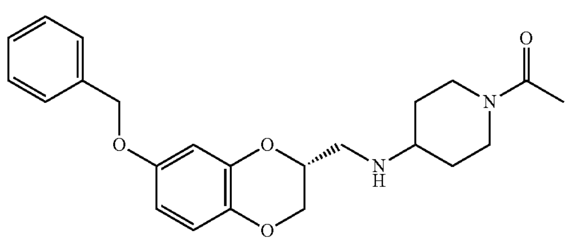 [SMILES: CC(=O)N1CCC(NC[C@@H]2COc3ccc(OCc4ccccc4)cc3O2)CC1] | 23 | |
| 40 | 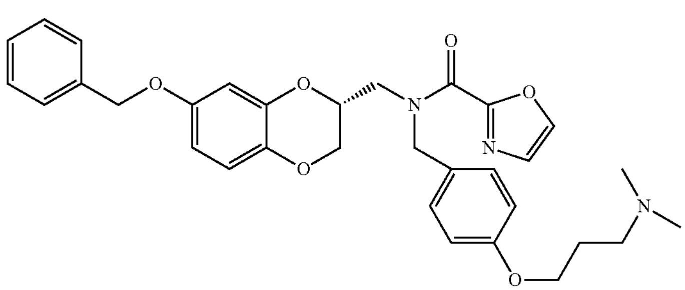 [SMILES: CN(C)CCCOc1ccc(CN(C[C@@H]2COc3ccc(OCc4ccccc4)cc3O2)C(=O)c2ncco2)cc1] | 173 | 14<br>2 |

TABLE 1-continued

| Example No. | Chemical Structure | SPR Response Units | Cell Viability (μM) H358 DLD-1 |
|---|---|---|---|
| 41 | 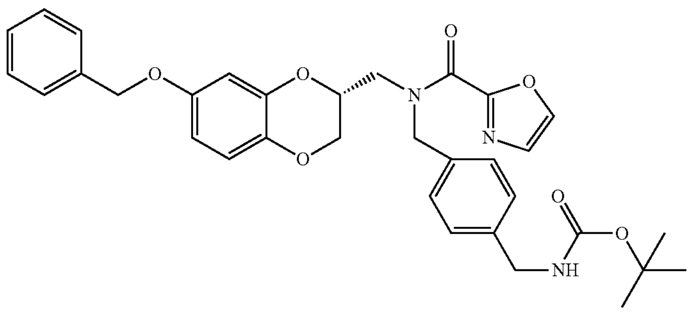 [SMILES: CC(C)(C)OC(=O)NCc1ccc(CN(C[C@@H]2COc3ccc(OCc4ccccc4)cc3O2)C(=O)c2ncco2)cc1] | 7 | 74<br>16 |
| 42 | 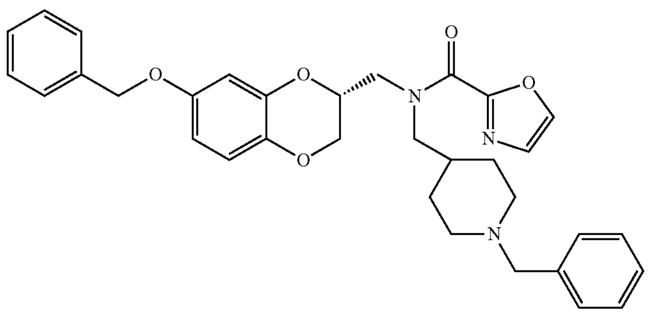 [SMILES: O=C(c1ncco1)N(CC1CCN(Cc2ccccc2)CC1)C[C@@H]1COc2ccc(OCc3ccccc3)cc2O1] | 93 | 29<br>3 |
| 43 | 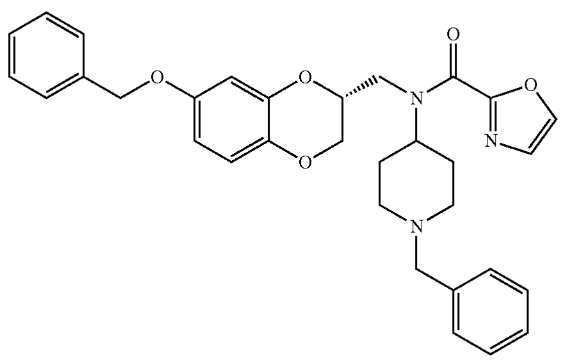 [SMILES: O=C(c1ncco1)N(C[C@@H]1COc2ccc(OCc3ccccc3)cc2O1)C1CCN(Cc2ccccc2)CC1] | 35 | 20.8<br>18.5 |
| 44 | 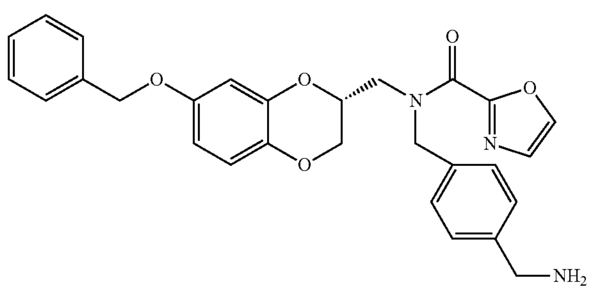 [SMILES: NCc1ccc(CN(C[C@@H]2COc3ccc(OCc4ccccc4)cc3O2)C(=O)c2ncco2)cc1] | 221 | >100<br>9 |
| 45 | 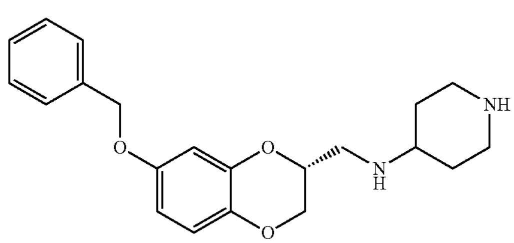 [SMILES: c1ccc(COc2ccc3c(c2)O[C@H](CNC2CCNCC2)CO3)cc1] | 22 | 26.3<br>9.6 |

TABLE 1-continued

| Example No. | Chemical Structure | SPR Response Units | Cell Viability (μM) H358 DLD-1 |
|---|---|---|---|
| 46 | 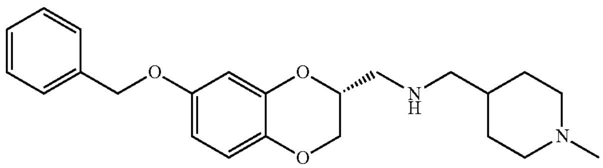 [SMILES: CN1CCC(CNC[C@@H]2COc3ccc(OCc4ccccc4)cc3O2)CC1] | 75 | 16<br>2 |
| 47 | 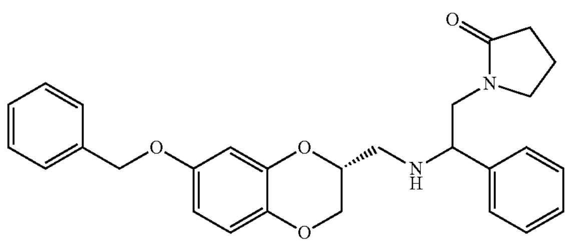 [SMILES: O=C1CCCN1CC(NC[C@@H]1COc2ccc(OCc3ccccc3)cc2O1)c1ccccc1] | 48 | 35<br>15.7 |
| 48 | 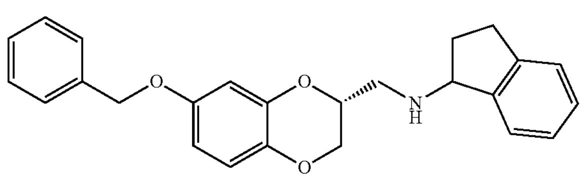 [SMILES: c1ccc(COc2ccc3c(c2)O[C@H](CNC2CCc4ccccc42)CO3)cc1] | 24 | |
| 49 | 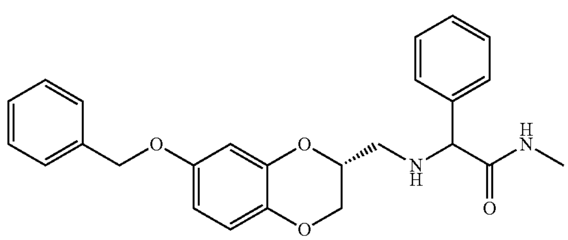 [SMILES: CNC(=O)C(NC[C@@H]1COc2ccc(OCc3ccccc3)cc2O1)c1ccccc1] | 67 | |
| 50 | 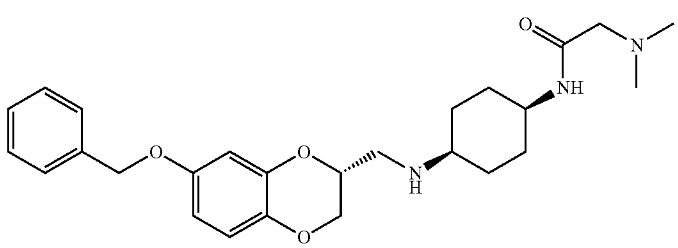 [SMILES: CN(C)CC(=O)N[C@H]1CC[C@@H](NC[C@@H]2COc3ccc(OCc4ccccc4)cc3O2)CC1] | 70 | 28<br>5 |
| 51 | 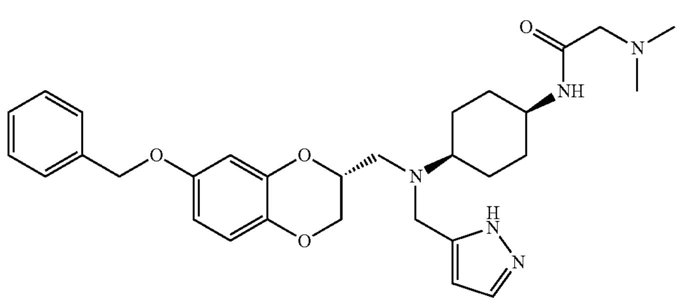 [SMILES: CN(C)CC(=O)N[C@H]1CC[C@@H](N(Cc2ccn[nH]2)C[C@@H]2COc3ccc(OCc4ccccc4)cc3O2)CC1] | 166 | 14<br>7.3 |

TABLE 1-continued

| Example No. | Chemical Structure | SPR Response Units | Cell Viability (μM) H358 DLD-1 |
|---|---|---|---|
| 52 | 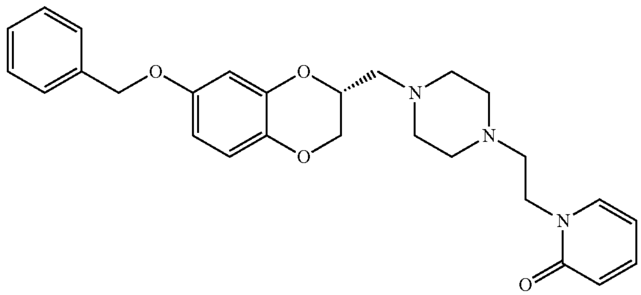 [SMILES: O=c1ccccn1CCN1CCN(C[C@@H]2COc3ccc(OCc4ccccc4)cc3O2)CC1] | 70 | >100<br>15 |
| 53 | 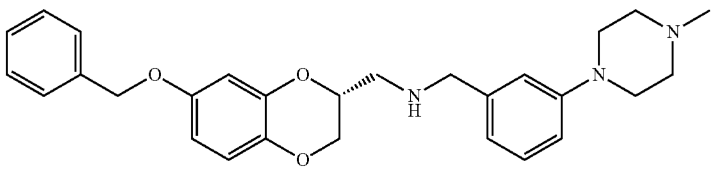 [SMILES: CN1CCN(c2cccc(CNC[C@@H]3COc4ccc(OCc5ccccc5)cc4O3)c2)CC1] | | 8.0<br>5.0 |
| 57 | 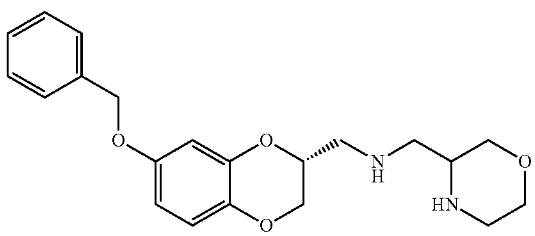 [SMILES: c1ccc(COc2ccc3c(c2)O[C@H](CNCC2COCCN2)CO3)cc1] | 29 | |
| 58 | 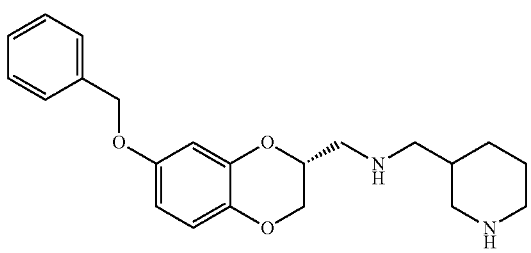 [SMILES: c1ccc(COc2ccc3c(c2)O[C@H](CNCC2CCCNC2)CO3)cc1] | | 14.7<br>13.8 |
| 59 | | 36 | >100<br>14 |
| 59 | | 39 | 22.7<br>18.6 |

TABLE 1-continued

| Example No. | Chemical Structure | SPR Response Units | Cell Viability (μM) H358 DLD-1 |
|---|---|---|---|
| 61 | 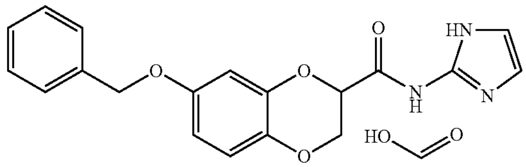 | 25 | >100<br>13 |
| 62 | 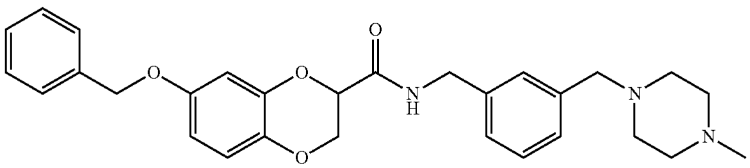 [SMILES: CN1CCN(Cc2cccc(CNC(=O)C3COc4ccc(OCc5ccccc5)cc4O3)c2)CC1] | 93 | 42<br>7 |
| 63 | 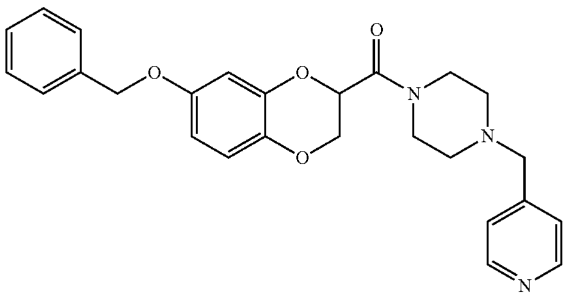 [SMILES: O=C(C1COc2ccc(OCc3ccccc3)cc2O1)N1CCN(Cc2ccncc2)CC1] | 79 | |
| 64 | 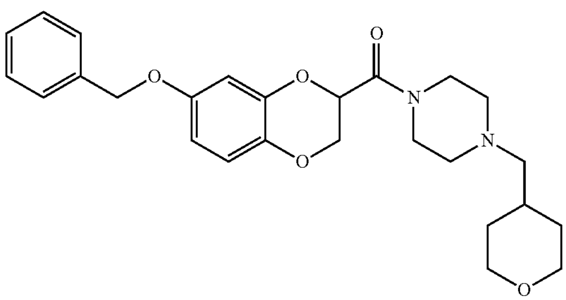 [SMILES: O=C(C1COc2ccc(OCc3ccccc3)cc2O1)N1CCN(CC2CCOCC2)CC1] | 36 | |
| 65 | 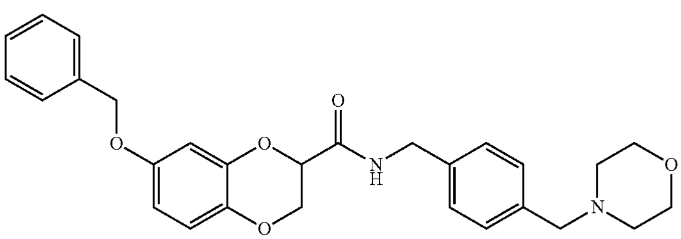 [SMILES: O=C(NCc1ccc(CN2CCOCC2)cc1)C1COc2ccc(OCc3ccccc3)cc2O1] | 46 | |
| 66 | 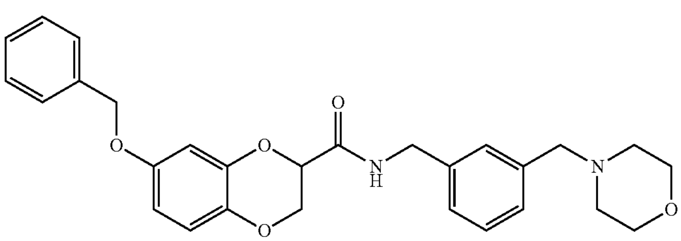 [SMILES: O=C(NCc1cccc(CN2CCOCC2)c1)C1COc2ccc(OCc3ccccc3)cc2O1] | 53 | |

TABLE 1-continued

| Example No. | Chemical Structure | SPR Response Units | Cell Viability (μM) H358 DLD-1 |
|---|---|---|---|
| 67 | 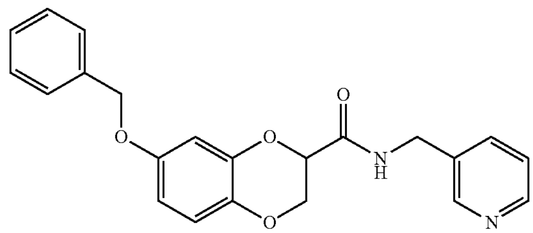 [SMILES: O=C(NCc1cccnc1)C1COc2ccc(OCc3ccccc3)cc2O1] | 49 | |
| 68 | 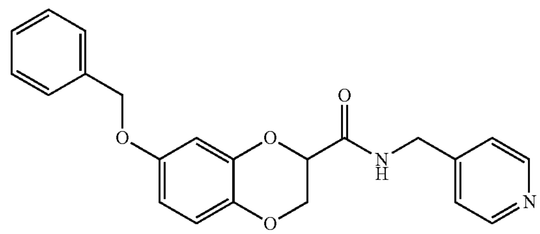 [SMILES: O=C(NCc1ccncc1)C1COc2ccc(OCc3ccccc3)cc2O1] | 57 | |
| 71 | 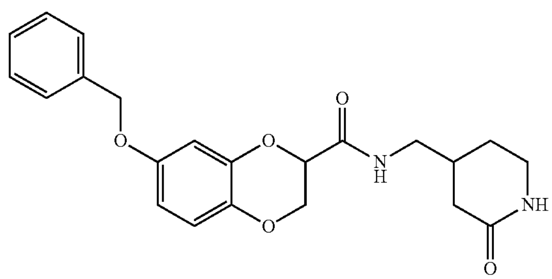 [SMILES: O=C1CC(CNC(=O)C2COc3ccc(OCc4ccccc4)cc3O2)CCN1] | 7 | |
| 72 | 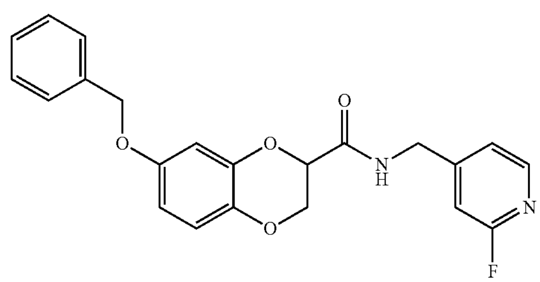 [SMILES: O=C(NCc1ccnc(F)c1)C1COc2ccc(OCc3ccccc3)cc2O1] | 12 | |
| 73 | 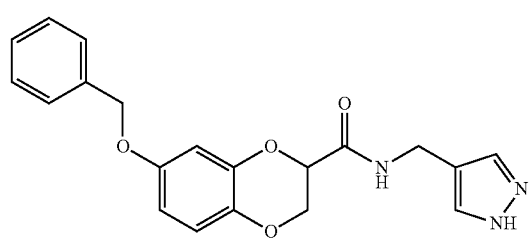 [SMILES: O=C(NCc1cn[nH]c1)C1COc2ccc(OCc3ccccc3)cc2O1] | 33 | |
| 74 | 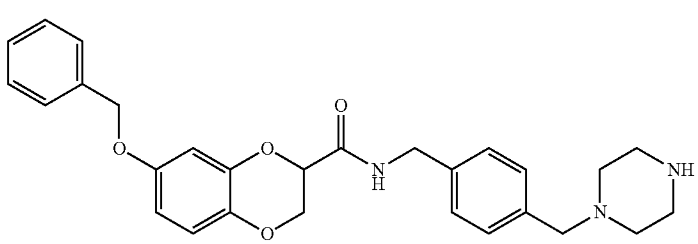 [SMILES: O=C(NCc1ccc(CN2CCNCC2)cc1)C1COc2ccc(OCc3ccccc3)cc2O1] | 115 | 21.3<br>16.7 |

TABLE 1-continued

| Example No. | Chemical Structure | SPR Response Units | Cell Viability (μM) H358 DLD-1 |
|---|---|---|---|
| 75 | 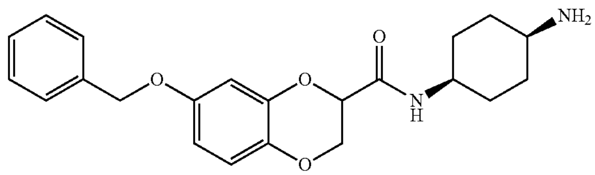 [SMILES: N[C@H]1CC[C@@H](NC(=O)C2COc3ccc(OCc4ccccc4)cc3O2)CC1] | 51 | |
| 76 | 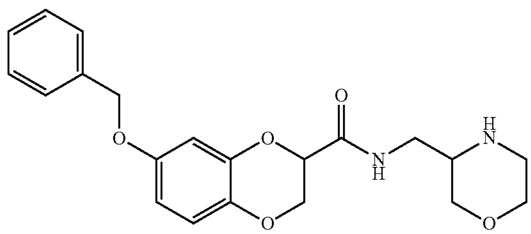 [SMILES: O=C(NCC1COCCN1)C1COc2ccc(OCc3ccccc3)cc2O1] | 48 | |
| 77 | 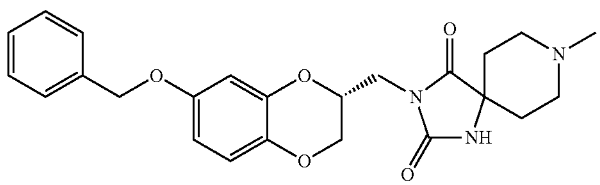 [SMILES: CN1CCC2(CC1)NC(=O)N(C[C@@H]1COc3ccc(OCc4ccccc4)cc3O1)C2=O] | 49 | 59 4 |
| 78 | 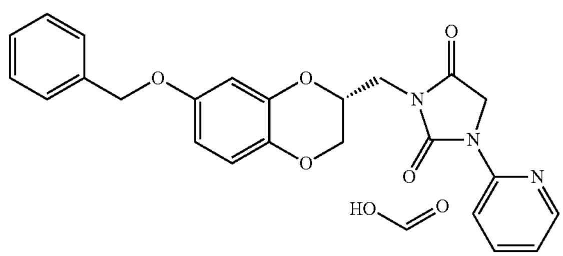 | 28 | |
| 79 | 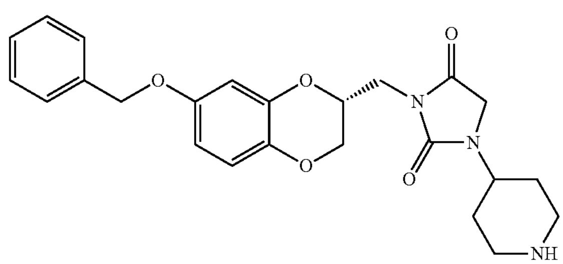 [SMILES: O=C1CN(C2CCNCC2)C(=O)N1C[C@@H]1COc2ccc(OCc3ccccc3)cc2O1] | 72 | 50 9 |
| 80 | 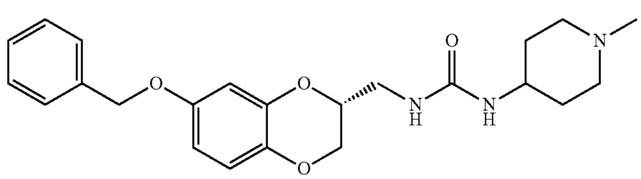 [SMILES: CN1CCC(NC(=O)NC[C@@H]2COc3ccc(OCc4ccccc4)cc3O2)CC1] | 93 | |
| 81 | 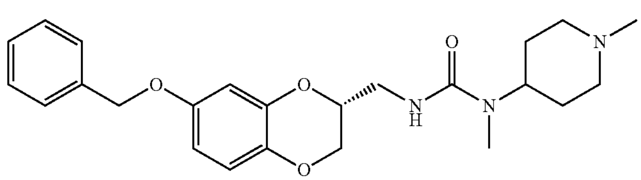 [SMILES: CN1CCC(N(C)C(=O)NC[C@@H]2COc3ccc(OCc4ccccc4)cc3O2)CC1] | 75 | |

TABLE 1-continued

| Example No. | Chemical Structure | SPR Response Units | Cell Viability (μM) H358 DLD-1 |
|---|---|---|---|
| 82 | 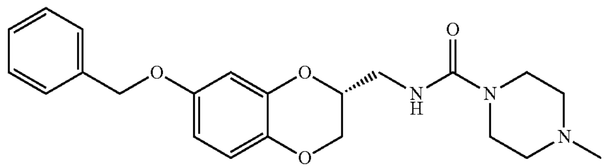 [SMILES: CN1CCN(C(=O)NC[C@@H]2COc3ccc(OCc4ccccc4)cc3O2)CC1] | 63 | |
| 83 | 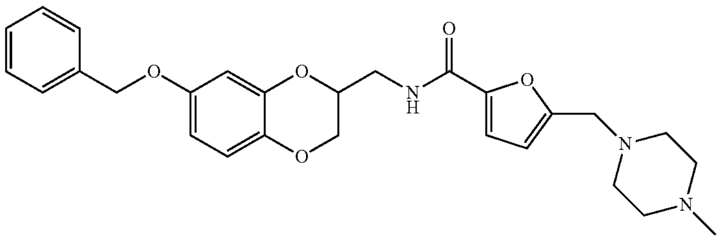 [SMILES: CN1CCN(Cc2ccc(C(=O)NCC3COc4ccc(OCc5ccccc5)cc4O3)o2)CC1] | 35 | |
| 85 | 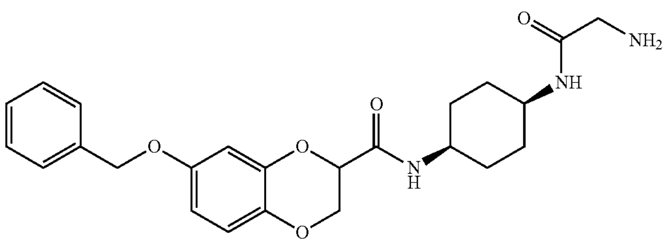 [SMILES: NCC(=O)N[C@H]1CC[C@@H](NC(=O)C2COc3ccc(OCc4ccccc4)cc3O2)CC1] | 64 | >100<br>10 |
| 86 | 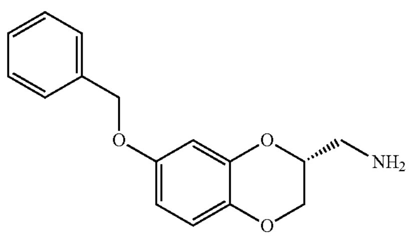 [SMILES: NC[C@@H]1COc2ccc(OCc3ccccc3)cc2O1] | 28 | |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in anyway.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

REFERENCES

Vetter I R, Wittinghofer A (2001) The guanine nucleotide-binding switch in three dimensions. Science 294: 1299-1304;

Downward J (2003) Targeting RAS signalling pathways in cancer therapy. Nat Rev Cancer 3: 11-22;

Marshall C J (1995) Specificity of receptor tyrosine kinase signalling: transient versus sustained extracellular signal-regulated kinase activation. Cell 80: 179-185;

Kolch W (2005) Coordinating ERK/MAPK signalling through scaffolds and inhibitors. Nat Rev Mol Cell Biol 6: 827-837;

Gonzale Garcia A, Pritchard C A, Paterson H F, Mavria G, Stamp G, Marshall C J (200 5)RaIGDS is required for tumor formation in a model of skin carcinogenesis. Cancer Cell 7: 219-226;

Rangarajan A, Hong S J, Gifford A, Weinberg R A (2004) Species- and cell type-specific requirements for cellular transformation. Cancer Cell 6: 171-183;

Adjei A A (2001) Blocking oncogenic Ras signalling for cancer therapy. J Natl Cancer Inst 93: 1062-1074;

Mendelsohn J, Baselga J (2000) The EGF receptor family as targets for cancer therapy. Oncogene 19: 6550-6565;

Johnson L, Mercer K, Greenbaum D, Bronson R T, Crowley D, Tuveson D A, Jacks T (2001) Somatic activation of the K-ras oncogene causes early onset lung cancer in mice. Nature 410: 1111-1116;

Chin L, Tam A, Pomerantz J, Wong M, Holash J, Bardeesy N, Shen Q, O'Hagan R, P antginis J, Zhou H, Horner I I J W, Cordon-Cardo C, Yancopoulos G D, DePinho R A (1999) Essential role for oncogenic Ras in tumour maintenance. Nature 400: 468-472;

Fisher G H, Wellen S L, Klimstra D, Lenczowski J M, Tichelaar J W, Lizak M J, Whitsett J A, Koretsky A, Varmus H E (2001) Induction and apoptotic regression of lung adenocarcinomas by regulation of a K-Ras transgene in the presence and absence of tumor suppressor genes. Genes Dev 15: 3249-3262;

Friday B B, Adjei A A (2005) K-ras as a target for cancer therapy. Biochim Biophys Acta 1756: 127-144;

Cattaneo A, Biocca S (1997) Intracellular Antibodies: Development and Applications. Springer: New York, USA;

Visintin M, Tse E, Axelson H, Rabbitts T H, Cattaneo A (1999) Selection of antibodies for intracellular function using a two-hybrid in vivo system. Proc Natl Acad Sci USA 96:11723-11728

Tse E, Lobato M N, Forster A, Tanaka T, Chung G T Y, Rabbitts T H (2002) Intracellula r antibody capture technology: application to selection of single chain Fv recognising the BCR-ABL oncogenic protein. J Mol Biol 317: 85-94;

Tanaka T, Rabbitts T H (2003) Intrabodies based on intracellular capture frameworks that bind the RAS protein with high affinity and impair oncogenic transformation. EMBO J., 22: 1025-1035;

Tanaka T, Lobato M N, Rabbitts T H (2003) Single domain intracellular antibodies: a minimal fragment for direct in vivo selection of antigen-specific intrabodies. J Mol Biol., 331:1109-1120;

Tanaka et al., (2007) Tumour prevention by a single antibody domain targeting the interaction of signal transduction proteins with RAS; EMBO J., 26, 3250-3259

Blundell T L, Sibanda B L, Montalvao R W, Brewerton S, Chelliah V, Worth C L, Harmer N J, Davies O, Burke D (2006) Structural biology and bioinformatics in drug design: opportunities and challenges for target identification and lead discovery. Philos Trans R Soc Lond B Biol Sci 361: 413-423

The invention claimed is:
1. A compound of formula I, or a salt or solvate thereof:

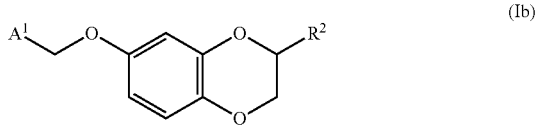

(Ib)

wherein,
A$^1$ is selected from C$_{3-11}$cycloalkyl optionally substituted by one or more R$^k$, C$_{6-11}$ aryl optionally substituted by one or more R$^k$, 3-15 membered heterocycloalkyl optionally substituted by one or more R$^k$, and 5-15 membered heteroaryl optionally substituted by one or more R$^k$;

R$^k$ is selected from hydrogen, hydroxyl, =O, halogen, CN, C$_{1-6}$ haloalkyl, C$_{1-6}$ haloalkoxy, C$_{1-6}$ alkyl, O—C$_{1-6}$ alkyl, C$_{3-6}$ cycloalkyl, 3-10 membered hetero-cycloalkyl, phenyl, benzyl, alkylheteroaryl, —C(=O)R$^d$, —C(=O)OR$^d$, —C(=O)NR$^c$R$^d$, —C(O)C(=O)R$^d$, —NR$^c$R$^d$, —NR$^c$C(=O)R$^d$, —NR$^c$C(=O)OR$^d$, —NR$^c$C(=O)NR$^c$R$^d$, —NR$^c$S(=O)$_2$R$^d$, —NR$^c$S(=O)$_2$NR$^c$R$^d$, —OR$^d$, —SR$^d$, —OC(=O)R$^d$, —OC(=O)NR$^c$R$^d$, —OC(=O)OR$^d$, —S(=O)$_2$R$^d$, —S(=O)R$^d$, —OS(=O)R$^d$, —OS(=O)$_2$R$^d$, —OS(=O)$_2$OR$^d$, —S(=O)NR$^c$R$^d$, —OS(=O)$_2$NR$^c$R$^d$, —S(=O)$_2$NR$^c$R$^d$; where said C$_{3-6}$ cycloalkyl, C$_{1-6}$ alkyl, 3-10 membered heterocycloalkyl, phenyl, benzyl, alkylheteroaryl, and O—C$_{1-6}$alkyl are optionally substituted with one or more groups selected from hydroxyl, halogen, =O, CN, C$_{1-6}$ haloalkyl, C$_{1-6}$ haloalkoxy, C$_{3-6}$ cycloalkyl, NR$^c$R$^d$, C$_{1-6}$ alkyl, O—C$_{1-6}$ alkyl, and phenyl;

R$^2$ is selected from —C(=O)NR$^c$R$^d$, —NR$^c$C(=O)R$^d$, —NR$^c$C(=O)OR$^d$, —NR$^c$C(=O)NR$^c$R$^d$, —NR$^c$S(=O)$_2$R$^d$, —NRS(=O)$_2$NR$^c$R$^d$; or a group of Formula III

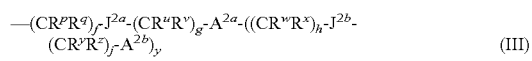

—(CR$^p$R$^q$)$_f$-J$^{2a}$-(CR$^u$R$^v$)$_g$-A$^{2a}$-((CR$^w$R$^x$)$_h$-J$^{2b}$-(CR$^y$R$^z$)$_j$-A$^{2b}$)$_y$        (III)

wherein
R$^p$, R$^q$, R$^u$ and R$^v$, are independently selected from hydrogen, C$_{1-6}$ alkyl, C(O)NR$^c$R$^d$, C$_{3-7}$cycloalkyl optionally substituted by one or more R$^b$, (C$_{1-6}$alkyl) phenyl optionally substituted by one or more R$^b$, phenyl optionally substituted by one or more R$^b$, (C$_{1-6}$ alkyl)C$_{3-7}$cycloalkyl optionally substituted by one or more R$^b$, 3-7 membered heterocycloalkyl optionally substituted by one or more R$^b$, 3-7 membered (C$_{1-6}$ alkyl)heterocycloalkyl optionally substituted by one or more R$^b$, 5-6 membered heteroaryl optionally substituted by one or more R$^b$, and 5-6 membered (C$_{1-6}$ alkyl)heteroaryl optionally substituted by one or more R$^b$;

R$^p$, R$^q$, R$^u$, R$^v$ are independently selected from hydrogen and C$_{1-6}$ alkyl;

f, g, h and j are independently selected from 0, 1, 2, 3 and 4; and y is selected from 0 and 1;

J$^{2a}$ is C(O)NR$^{s1}$, NR$^{s1}$C(O) and NR$^{s1}$; where R$^{s1}$ is selected from hydrogen, C$_{1-6}$ alkyl, C$_{3-7}$cycloalkyl optionally substituted by one or more R$^b$, (C$_{1-6}$alkyl) phenyl optionally substituted by one or more R$^b$, phenyl optionally substituted by one or more R$^b$, (C$_{1-6}$ alkyl)C$_{3-7}$cycloalkyl optionally substituted by one or more R$^b$, 3-7 membered heterocycloalkyl optionally substituted by one or more R$^b$, 3-7 membered (C$_{1-6}$ alkyl)heterocycloalkyl optionally substituted by one or more R$^b$, 5-6 membered heteroaryl optionally substituted by one or more R$^b$, and 5-6 membered (C$_{1-6}$alkyl) heteroaryl optionally substituted by one or more R$^b$;

J$^{2b}$ is selected from O, S, C(O), CH$_2$, C(O)NR$^{s2}$, NR$^{s2}$C (O) and NR$^{s2}$; where R$^{s2}$ is selected from hydrogen, C$_{1-6}$ alkyl, C$_{3-7}$cycloalkyl optionally substituted by one or more R$^b$, (C$_{1-6}$ alkyl)phenyl optionally substituted by one or more R$^b$, phenyl optionally substituted by one or more R$^b$, (C$_{1-6}$alkyl)C$_{3-7}$cycloalkyl optionally substituted by one or more R$^b$, 3-7 membered heterocycloalkyl optionally substituted by one or more R$^b$, 3-7 membered (C$_{1-6}$ alkyl)heterocycloalkyl optionally substituted by one or more R$^b$, 5-6 membered heteroaryl optionally substituted by one or more R$^b$, and 5-6 membered (C$_{1-6}$alkyl)heteroaryl optionally substituted by one or more R$^b$;

each R$^b$ is independently selected from hydroxyl, =O, halogen, C$_{1-6}$ alkyl, CN, C$_{1-6}$ haloalkyl, C$_{1-}$ haloalkoxy, $C_{3-6}$ cycloalkyl, $OR^d$, 3-10 membered heterocycloalkyl, wherein said $C_{1-6}$ alkyl, $C_{3-6}$ cycloalkyl and 3-10 membered heterocycloalkyl are optionally substituted with one or more groups selected from hydroxyl, halogen, CN, $NR^cR^d$, $C_{1-6}$ haloalkyl, $C_{3-6}$ cycloalkyl, $C_{1-6}$ alkyl, phenyl and O—$C_{1-6}$ alkyl;

$A^{2a}$ is selected from $C_{3-11}$ cycloalkyl optionally substituted by one or more $R^t$, 3-15 membered heterocycloalkyl optionally substituted by one or more $R^t$, $C_{6-11}$ aryl optionally substituted by one or more $R^t$, 5-15 membered heteroaryl optionally substituted by one or more $R^t$;

$A^{2b}$ is selected from $C_{3-11}$ cycloalkyl optionally substituted by one or more $R^t$, 3-15 membered heterocycloalkyl optionally substituted by one or more $R^t$, $C_{6-11}$ aryl optionally substituted by one or more $R^t$, 5-15 membered heteroaryl optionally substituted by one or more $R^t$; and $R^t$ is selected from hydroxyl, =O, halogen, CN, $C_{1-6}$ haloalkyl, $C_{1-6}$ haloalkoxy, $C_{1-6}$ alkyl, O—$C_{1-6}$ alkyl, $C_{3-6}$ cycloalkyl, 5-6 membered heteroaryl, 3-7 membered heterocycloalkyl, —C(=O)$R^d$, —C(=O)O$R^d$, —C(=O)N$R^cR^d$, —C(O)C(=O)$R^d$, —N$R^cR^d$, —N$R^c$C(=O)$R^d$, —N$R^c$C(=O)O$R^d$, —N$R^c$C(=O)N$R^cR^d$, —N$R^c$S(=O)$_2R^d$, —N$R^c$S(=O)$_2$N$R^cR^d$, —O$R^d$, —S$R^d$, —OC(=O)$R^d$, —OC(=O)N$R^cR^d$, —OC(=O)O$R^d$, —S(=O)$_2R^d$, —S(=O)$R^d$, —OS(=O)$R^d$, —OS(=O)$_2R^d$, —OS(=O)$_2$O$R^d$, —S(=O)N$R^cR^d$, —OS(=O)$_2$N$R^cR^d$, —S(=O)$_2$N$R^cR^d$; where said $C_{3-6}$ cycloalkyl, $C_{1-6}$ alkyl, 5-6 membered heteroaryl, 3-7 membered heterocycloalkyl, $C_{1-6}$ alkyl and O—$C_{1-6}$alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, C(O)N$R^cR^d$, N$R^cR^d$, $C_{1-6}$ alkyl, and O—$C_{1-6}$ alkyl; and wherein, each $R^c$ is independently selected from hydrogen, hydroxyl, halogen, CN, $C_{1-6}$ haloalkyl, $C_{3-6}$ cycloalkyl, $C_{1-6}$ alkyl and O—$C_{1-6}$ alkyl;

each $R^d$ is independently selected from hydrogen, hydroxyl, halogen, CN, $C_{1-6}$ haloalkyl, 3-7 membered heterocycloalkyl, $C_{3-6}$ cycloalkyl, $C_{1-6}$ alkyl, O—$C_{1-6}$ alkyl, C(=O)O($C_{1-6}$alkyl), 5-6 membered heteroaryl and phenyl, wherein said $C_{1-6}$ alkyl, O—$C_{1-6}$ alkyl, phenyl, 3-7 membered heterocycloalkyl, 5-6 membered heteroaryl and $C_30.6$ cycloalkyl are optionally substituted with one or more groups selected from hydroxyl, =O, halogen, CN, $NH_2$, NHMe, $NMe_2$, $C_{1-6}$ haloalkyl, $C_{3-6}$ cycloalkyl, $C_{6-11}$ aryl, $C_{1-6}$ alkyl and O—$C_{1-6}$ alkyl; or $R^c$ and $R^d$, when attached to the same atom, together with the atom to which they are attached form a 3-10 membered ring, optionally containing one or more for heteroatoms selected from O, N and S, and wherein said ring is optionally substituted with one or more $R^m$; and $R^m$ is selected from hydrogen, hydroxyl, =O, halogen, $C_{1-6}$ alkyl, CN, $C_{1-6}$ haloalkyl, $C_{1-6}$ haloalkoxy, $C_{3-6}$ cycloalkyl, $OR^d$, 3-10 membered heterocycloalkyl, 5-6 membered ($C_{1-6}$ alkyl)heterocycloalkyl 5-6 membered ($C_{1-6}$ alkyl)heteroaryl wherein said $C_{1-6}$ alkyl, $C_{3-6}$ cycloalkyl, 3-10 membered heterocycloalkyl, 5-6 membered ($C_{1-6}$ alkyl)heterocycloalkyl, and 5-6 membered ($C_{1-6}$ alkyl)heteroaryl are optionally substituted with one or more groups selected from hydroxyl, halogen, CN, $NH_2$, NHMe, $NMe_2$, $C_{1-6}$ haloalkyl, $C_{3-6}$ cycloalkyl, $C_{1-6}$ alkyl, phenyl, and O—$C_{1-6}$ alkyl.

2. A compound according to claim 1, or a salt or solvate thereof, wherein $A^1$ is selected from $C_{6-11}$ aryl optionally substituted by one or more $R^k$, 3-15 membered heterocycloalkyl optionally substituted by one or more $R^k$, and 5-15 membered heteroaryl optionally substituted by one or more $R^k$.

3. A compound according to claim 1, or a salt or solvate thereof, wherein $R^k$ is selected from hydrogen, hydroxyl, =O, halogen, CN, $C_{1-6}$ haloalkyl, $C_{1-6}$ haloalkoxy, $C_{1-6}$ alkyl, and O—$C_{1-6}$ alkyl; where said $C_{1-6}$ alkyl and O—$C_{1-6}$ alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^cR^d$, $C_{1-6}$ alkyl, O—$C_{1-6}$ alkyl, and phenyl.

4. A compound according to claim 1, or a salt or solvate thereof, wherein $A^1$ is

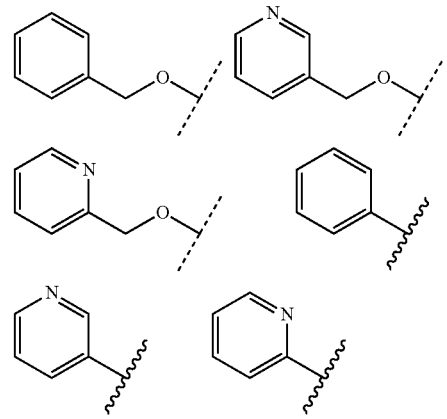

where the phenyl and pyridyl rings are optionally substituted with one or more groups selected from $C_{1-3}$ alkyl and halogen.

5. A compound according to claim 1, or a salt or solvate thereof, wherein $R^2$ is selected from —C(=O)N$R^cR^d$, —$N^c$C(=O)$R^d$ and a group of Formula III.

6. A compound according to claim 1, or a salt or solvate thereof, wherein $R^2$ is selected from a group of Formula III.

7. A compound according to claim 1, or a salt or solvate thereof, wherein $J^{2a}$ is selected from C(O)N$R^{s1}$ and N$R^{s1}$C(O).

8. A compound according to claim 1, or a salt or solvate thereof, wherein the compound is of sub-formula Ic:

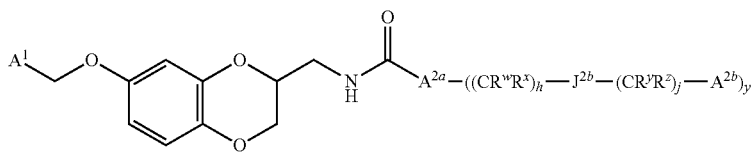

(Ic)

where $A^1$, $A^{2a}$, $R^w$, $R^x$, $J^{2b}$, $R^y$, $R^z$, $A^{2b}$, $h$, $j$ and $y$ are as defined in claim 1.

9. A compound according to claim 1, or a salt or solvate thereof, wherein $A^{2a}$ is selected from $C_{3-11}$ cycloalkyl optionally substituted by one or more $R^t$, 3-15 membered heterocycloalkyl optionally substituted by one or more $R^t$, $C_{6-11}$ aryl optionally substituted by one or more $R^t$, and 5-15 membered heteroaryl optionally substituted by one or more $R^t$.

10. A compound according to claim 1, or a salt or solvate thereof, wherein $A^{2a}$ is selected from phenyl optionally substituted by one or more $R^t$, tetrahydropyran optionally substituted by one or more $R^t$, piperazine optionally substituted by one or more $R^t$, piperidine optionally substituted by one or more $R^t$, furan optionally substituted by one or more $R^t$, and oxazole optionally substituted by one or more $R^t$.

11. A compound according to claim 1, or a salt or solvate thereof, wherein $y$ is 0.

12. A compound according to claim 1, or a salt or solvate thereof, wherein $y$ is 1.

13. A compound according to claim 1, or a salt or solvate thereof, wherein $J^{2b}$ is $CH_2$.

14. A compound according to claim 1, or a salt or solvate thereof, wherein $A^{2b}$ is selected from phenyl optionally substituted by one or more $R^t$, 5-6 membered heterocycloalkyl optionally substituted by one or more $R^t$, and a 5-6 membered heteroaryl optionally substituted by one or more $R^t$.

15. A compound according to claim 1, or a salt or solvate thereof, wherein $R^t$ is selected from hydroxyl, =O, halogen, $C_{1-6}$ alkyl, O—$C_{1-6}$ alkyl, $C_{3-6}$ cycloalkyl, 5-6 membered heteroaryl, 3-7 membered heterocycloalkyl, —C(=O)$R^d$, —C(=O)O$R^d$, —C(=O)NR$^c$R$^d$, —NR$^c$R$^d$, —NR$^c$C(=O)R$^d$, —NR$^c$C(=O)O$R^d$, and —NR$^c$C(=O)NR$^c$R$^d$; where said $C_{3-6}$ cycloalkyl, $C_{1-6}$ alkyl, 5-6 membered heteroaryl, 3-7 membered heterocycloalkyl, $C_{1-6}$ alkyl and O—$C_{1-6}$ alkyl are optionally substituted with one or more groups selected from hydroxyl, halogen, =O, CN, $C_{1-6}$ haloalkyl, $C_{1-6}$ haloalkoxy, $C_{3-6}$ cycloalkyl, C(O)NR$^c$R$^d$, NR$^c$R$^d$, $C_{1-6}$ alkyl, and O—$C_{1-6}$ alkyl.

16. A compound according to claim 1, or a salt or solvate thereof, wherein $R^2$ is selected from

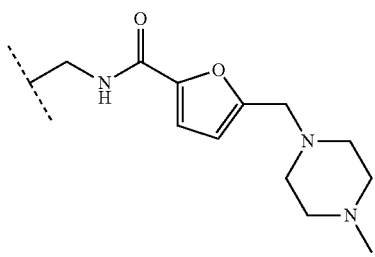

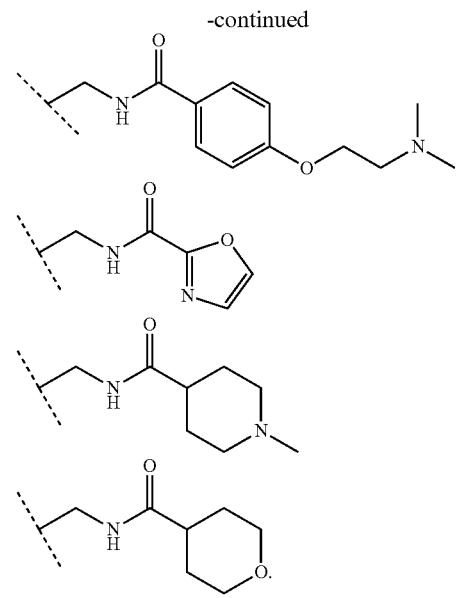

17. A compound, or a salt or solvate thereof, selected from:

5-(4-Methyl-piperazin-1-ylmethyl)-furan-2-carboxylic acid ((R)-7-benzyloxy-2,3-dihydro-benzo[1,4]dioxin-2-ylmethyl)-amide;

Oxazole-2-carboxylic acid ((R)-7-benzyloxy-2,3-dihydro-benzo[1,4]dioxin-2-ylmethyl)-amide;

Oxazole-2-carboxylic acid [(R)-7-(pyridin-3-ylmethoxy)-2,3-dihydro-benzo[1,4]dioxin-2-ylmethyl]-amide;

Oxazole-2-carboxylic acid [(R)-7-(1H-pyrazol-4-ylmethoxy)-2,3-dihydro-benzo[1,4]dioxin-2-ylmethyl]-amide;

Oxazole-2-carboxylic acid [(R)-7-(1-methyl-piperidin-4-ylmethoxy)-2,3-dihydro-benzo[1,4]dioxin-2-ylmethyl]-amide;

5-(4-Methyl-piperazin-1-ylmethyl)-furan-2-carboxylic acid [(R)-7-(4-methoxy-benzyloxy)-2,3-dihydro-benzo[1,4]dioxin-2-ylmethyl]-amide;

5-(4-Methyl-piperazin-1-ylmethyl)-furan-2-carboxylic acid ((R)-7-phenethyloxy-2,3-dihydro-benzo[1,4]dioxin-2-ylmethyl)-amide;

5-(4-Methyl-piperazin-1-ylmethyl)-furan-2-carboxylic acid [(R)-7-(4-chloro-benzyloxy)-2,3-dihydro-benzo[1,4]dioxin-2-ylmethyl]-amide;

5-(4-Methyl-piperazin-1-ylmethyl)-oxazole-2-carboxylic acid ((R)-7-benzyloxy-2,3-dihydro-benzo[1,4]dioxin-2-ylmethyl)-amide;

1-methyl-piperidine-4-carboxylic acid ((R)-7-benzyloxy-2,3-dihydro-benzo[1,4]dioxin-2-ylmethyl)-amide;

Tetrahydro-pyran-4-carboxylic acid ((R)-7-benzyloxy-2,3-dihydro-benzo[1,4]dioxin-2-ylmethyl)-amide;

N-((R)-7-Benzyloxy-2,3-dihydro-benzo[1,4]dioxin-2-ylmethyl)-3-dimethylamino-propionamide;

Oxazole-2-carboxylic acid ((R)-7-benzyloxy-2,3-dihydro-benzo[1,4]dioxin-2-ylmethyl)-[4-(3-dimethylamino-propoxy)-benzyl]-amide;
(4-{[((R)-7-Benzyloxy-2,3-dihydro-benzo[1,4]dioxin-2-ylmethyl)-(oxazole-2-carbonyl)-amino]-methyl}-benzyl)-carbamic acid tert-butyl ester;
Oxazole-2-carboxylic acid (4-aminomethyl-benzyl)-((R)-7-benzyloxy-2,3-dihydro-benzo[1,4]dioxin-2-ylmethyl)-amide;
Oxazole-2-carboxylic acid ((R)-7-benzyloxy-2,3-dihydro-benzo[1,4]dioxin-2-ylmethyl)-(1-benzyl-piperidin-4-ylmethyl)-amide;
((R)-7-Benzyloxy-2,3-dihydro-benzo[1,4]dioxin-2-ylmethyl)-(tetrahydro-pyran-4-ylmethyl)-amine;
Oxazole-2-carboxylic acid ((R)-7-benzyloxy-2,3-dihydro-benzo[1,4]dioxin-2-ylmethyl)-(1-benzyl-piperidin-4-yl)-amide;
5-(4-Methyl-piperazin-1-ylmethyl)-furan-2-carboxylic acid [(R)-7-(5-chloro-pyridin-3-ylmethoxy)-2,3-dihydro-benzo[1,4]dioxin-2-ylmethyl]-amide;
5-(4-Methyl-piperazin-1-ylmethyl)-furan-2-carboxylic acid ((R)-7-benzylamino-2,3-dihydro-benzo[1,4]dioxin-2-ylmethyl)-amide;
5-(4-Methyl-piperazin-1-ylmethyl)-furan-2-carboxylic acid [(R)-7-(5-chloro-pyridin-2-ylmethoxy)-2,3-dihydro-benzo[1,4]dioxin-2-ylmethyl]-amide;
1-{2-[((R)-7-Benzyloxy-2,3-dihydro-benzo[1,4]dioxin-2-ylmethyl)-amino]-2-phenyl-ethyl}-pyrrolidin-2-one;
((R)-7-Benzyloxy-2,3-dihydro-benzo[1,4]dioxin-2-ylmethyl)-indan-1-yl-amine;
C-((R)-7-Benzyloxy-2,3-dihydro-benzo[1,4]dioxin-2-yl)-methylamine;
2-[((R)-7-Benzyloxy-2,3-dihydro-benzo[1,4]dioxin-2-ylmethyl)-amino]-N-methyl-2-phenyl-acetamide;
2-[((R)-7-Benzyloxy-2,3-dihydro-benzo[1,4]dioxin-2-ylmethyl)-amino]-N-methyl-2-phenyl-acetamide;
7-Benzyloxy-2,3-dihydro-benzo[1,4]dioxine-2-carboxylic acid (1-methyl-piperidin-4-ylmethyl)-amide;
7-Benzyloxy-2,3-dihydro-benzo[1,4]dioxine-2-carboxylic acid (4-amino-cyclohexyl)-amide;
3-((R)-7-Benzyloxy-2,3-dihydro-benzo[1,4]dioxin-2-ylmethyl)-8-methyl-1,3,8-triaza-spiro[4.5]decane-2,4-dione;
7-Benzyloxy-2,3-dihydro-benzo[1,4]dioxine-2-carboxylic acid (1H-imidazol-2-yl)-amide;
3-((R)-7-Benzyloxy-2,3-dihydro-benzo[1,4]dioxin-2-ylmethyl)-1-pyridin-2-yl-imidazolidine-2,4-dione;
7-Benzyloxy-2,3-dihydro-benzo[1,4]dioxine-2-carboxylic acid [4-(2-amino-acetylamino)-cyclohexyl]-amide;
3-((R)-7-Benzyloxy-2,3-dihydro-benzo[1,4]dioxin-2-ylmethyl)-1-piperidin-4-yl-imidazolidine-2,4-dione;
((R)-7-Benzyloxy-2,3-dihydro-benzo[1,4]dioxin-2-ylmethyl)-(1-methyl-piperidin-4-ylmethyl)-amine;
7-Benzyloxy-2,3-dihydro-benzo[1,4]dioxine-2-carboxylic acid 3-(4-methyl-piperazin-1-ylmethyl)-benzylamide;
(7-Benzyloxy-2,3-dihydro-benzo[1,4]dioxin-2-yl)-(4-pyridin-4-ylmethyl-piperazin-1-yl)-methanone;
(7-Benzyloxy-2,3-dihydro-benzo[1,4]dioxin-2-yl)-[4-(tetrahydro-pyran-4-ylmethyl)-piperazin-1-yl]-methanone;
N-{4-[((R)-7-Benzyloxy-2,3-dihydro-benzo[1,4]dioxin-2-ylmethyl)-amino]-cyclohexyl}-2-dimethylamino-acetamide;
1-{2-[4-((R)-7-Benzyloxy-2,3-dihydro-benzo[1,4]dioxin-2-ylmethyl)-piperazin-1-yl]-ethyl}-1H-pyridin-2-one;
N-{4-[((R)-7-Benzyloxy-2,3-dihydro-benzo[1,4]dioxin-2-ylmethyl)-(2H-pyrazol-3-ylmethyl)-amino]-cyclohexyl}-2-dimethylamino-acetamide;
((R)-7-Benzyloxy-2,3-dihydro-benzo[1,4]dioxin-2-ylmethyl)-[3-(4-methyl-piperazin-1-yl)-benzyl]-amine;
1-(7-benzyloxy-2,3-dihydro-benzo[1,4]dioxin-2-ylmethyl)-3-(1-methyl-piperidin-4-yl)-urea;
4-methyl-piperazine-1-carboxylic acid ((R)-7-benzyloxy-2,3-dihydro-benzo[1,4]dioxin-2-ylmethyl)-amide;
3-(7-Benzyloxy-2,3-dihydro-benzo[1,4]dioxin-2-ylmethyl)-1-methyl-1-(1-methyl-piperidin-4-yl)-urea;
N-((R)-7-Benzyloxy-2,3-dihydro-benzo[1,4]dioxin-2-ylmethyl)-3-(4-methyl-piperazin-1-ylmethyl)-benzamide;
N-((R)-7-Benzyloxy-2,3-dihydro-benzo[1,4]dioxin-2-ylmethyl)-2-(1-methyl-piperidin-4-yl)-acetamide;
N-((R)-7-Benzyloxy-2,3-dihydro-benzo[1,4]dioxin-2-ylmethyl)-2-piperidin-4-yl-acetamide;
7-Benzyloxy-2,3-dihydro-benzo[1,4]dioxine-2-carboxylic acid 4-morpholin-4-ylmethyl-benzylamide;
7-Benzyloxy-2,3-dihydro-benzo[1,4]dioxine-2-carboxylic acid 3-morpholin-4-ylmethyl-benzylamide;
4-(4-{[(7-benzyloxy-2,3-dihydro-benzo[1,4]dioxine-2-carbonyl)-amino]-methyl}-benzyl)-piperazine-1-carboxylic acid tert-butyl ester;
7-benzyloxy-2,3-dihydro-benzo[1,4]dioxine-2-carboxylic acid 4-piperazin-1-ylmethyl-benzylamide;
7-Benzyloxy-2,3-dihydro-benzo[1,4]dioxine-2-carboxylic acid (pyridin-3-ylmethyl)-amide;
7-Benzyloxy-2,3-dihydro-benzo[1,4]dioxine-2-carboxylic acid (pyridin-4-ylmethyl)-amide;
N-((R)-7-Benzyloxy-2,3-dihydro-benzo[1,4]dioxin-2-ylmethyl)-2-pyridin-4-yl-acetamide;
7-Benzyloxy-2,3-dihydro-benzo[1,4]dioxine-2-carboxylic acid (morpholin-3-ylmethyl)-amide;
N-((R)-7-Benzyloxy-2,3-dihydro-benzo[1,4]dioxin-2-ylmethyl)-2-pyridin-3-yl-acetamide;
7-Benzyloxy-2,3-dihydro-benzo[1,4]dioxine-2-carboxylic acid (2-oxo-1,2-dihydro-pyridin-4-ylmethyl)-amide;
7-Benzyloxy-2,3-dihydro-benzo[1,4]dioxine-2-carboxylic acid (2-oxo-piperidin-4-ylmethyl)-amide;
7-Benzyloxy-2,3-dihydro-benzo[1,4]dioxine-2-carboxylic acid (2-fluoro-pyridin-4-ylmethyl)-amide;
N-((R)-7-Benzyloxy-2,3-dihydro-benzo[1,4]dioxin-2-ylmethyl)-2-(3,5-dimethyl-1H-pyrazol-4-yl)-acetamide;
7-Benzyloxy-2,3-dihydro-benzo[1,4]dioxine-2-carboxylic acid (1H-pyrazol-4-ylmethyl)-amide;
Piperidine-4-carboxylic acid ((R)-7-benzyloxy-2,3-dihydro-benzo[1,4]dioxin-2-ylmethyl)-amide;
((R)-7-Benzyloxy-2,3-dihydro-benzo[1,4]dioxin-2-ylmethyl)-piperidin-4-yl-amine;
((R)-7-Benzyloxy-2,3-dihydro-benzo[1,4]dioxin-2-ylmethyl)-morpholin-3-ylmethyl-amine;
1-Carbamoylmethyl-piperidine-4-carboxylic acid ((R)-7-benzyloxy-2,3-dihydro-benzo[1,4]dioxin-2-ylmethyl)-amide;
1-{4-[((R)-7-Benzyloxy-2,3-dihydro-benzo[1,4]dioxin-2-ylmethyl)-amino]-piperidin-1-yl}-ethanone;
5-{[((R)-7-Benzyloxy-2,3-dihydro-benzo[1,4]dioxin-2-ylmethyl)-amino]-methyl}-piperidin-2-one;
((R)-7-Benzyloxy-2,3-dihydro-benzo[1,4]dioxin-2-ylmethyl)-piperidin-3-ylmethyl-amine;

1-Methyl-piperidine-4-carboxylic acid [(R)-7-(3,4-difluoro-benzyloxy)-2,3-dihydro-benzo[1,4]dioxin-2-yl-methyl]-amide;
1-Methyl-piperidine-4-carboxylic acid [(R)-7-(3-methyl-benzyloxy)-2,3-dihydro-benzo[1,4]dioxin-2-ylmethyl]-amide;
1-Methyl-piperidine-4-carboxylic acid [(R)-7-(4-methyl-benzyloxy)-2,3-dihydro-benzo[1,4]dioxin-2-ylmethyl]-amide;
1-Methyl-piperidine-4-carboxylic acid [(R)-7-(3-chloro-benzyloxy)-2,3-dihydro-benzo[1,4]dioxin-2-ylmethyl]-amide;
1-Methyl-piperidine-4-carboxylic acid [(R)-7-(4-chloro-benzyloxy)-2,3-dihydro-benzo[1,4]dioxin-2-ylmethyl]-amide;
1-Methyl-piperidine-4-carboxylic acid [(R)-7-(4-fluoro-benzyloxy)-2,3-dihydro-benzo[1,4]dioxin-2-ylmethyl]-amide;
1-Methyl-piperidine-4-carboxylic acid [(R)-7-(2-methyl-benzyloxy)-2,3-dihydro-benzo[1,4]dioxin-2-ylmethyl]-amide; and
1-Furan-2-ylmethyl-piperidine-4-carboxylic acid ((R)-7-benzyloxy-2,3-dihydro-benzo[1,4]dioxin-2-ylmethyl)-amide.

18. A pharmaceutical composition comprising a compound according to claim 1 or a pharmaceutically acceptable salt or solvate thereof, and one or more pharmaceutically acceptable excipients.

19. A combination comprising a compound according to claim 1 and a further therapeutically active agent.

20. A compound according to claim 1, or a salt or solvate thereof, wherein $A^1$ is phenyl optionally substituted by one or more $R^k$.

* * * * *